US012398352B2

(12) United States Patent
Fearnot et al.

(10) Patent No.: US 12,398,352 B2
(45) Date of Patent: Aug. 26, 2025

(54) DIFFERENTIAL PRESSURE MATERIAL PROCESSING SYSTEMS, APPARATUS, METHODS, AND PRODUCTS

(71) Applicants: Cook Medical Technologies LLC, Bloomington, IN (US); Muffin Incorporated, West Lafayette, IN (US)

(72) Inventors: Neal Fearnot, West Lafayette, IN (US); Sarah Robbins, Lafayette, IN (US); Marc Buhrmester, Dayton, IN (US); Joshua Krieger, Topsfield, MA (US); Gabriel Converse, Lafayette, IN (US)

(73) Assignees: Cook Medical Technologies LLC, Bloomington, IN (US); Muffin Incorporated, West Lafayette, IN (US)

( * ) Notice: Subject to any disclaimer, the term of this patent is extended or adjusted under 35 U.S.C. 154(b) by 1144 days.

(21) Appl. No.: 17/291,757

(22) PCT Filed: Nov. 8, 2019

(86) PCT No.: PCT/US2019/060429
§ 371 (c)(1),
(2) Date: May 6, 2021

(87) PCT Pub. No.: WO2020/097436
PCT Pub. Date: May 14, 2020

(65) Prior Publication Data
US 2022/0010251 A1    Jan. 13, 2022

Related U.S. Application Data

(60) Provisional application No. 62/757,783, filed on Nov. 9, 2018.

(51) Int. Cl.
*C12M 3/00*     (2006.01)
*C12M 1/00*     (2006.01)
*C12M 1/34*     (2006.01)

(52) U.S. Cl.
CPC ............ *C12M 21/08* (2013.01); *C12M 23/44* (2013.01); *C12M 23/46* (2013.01); *C12M 29/00* (2013.01); *C12M 41/40* (2013.01)

(58) Field of Classification Search
CPC ............................. C12M 21/08; C12M 35/04
See application file for complete search history.

(56) References Cited

U.S. PATENT DOCUMENTS

| 4,804,628 A | 2/1989 | Cracauer et al. |
| 6,048,723 A * | 4/2000 | Banes ................... C12M 35/04 |
| | | 435/305.4 |

(Continued)

FOREIGN PATENT DOCUMENTS

WO    2004009757 A1    1/2004

OTHER PUBLICATIONS

Australian Examination Report No. 1 for standard patent application, Application No. 2019377857, dated Aug. 4, 2022.

(Continued)

*Primary Examiner* — Jonathan M Hurst
(74) *Attorney, Agent, or Firm* — MacMillan, Sobanski & Todd, LLC

(57) ABSTRACT

Differential pressure material processing systems, apparatus, methods, and products are described. An example embodiment of a differential pressure material processing system includes a tank, a holding member, and a sheet of tissue disposed within the holding member. The holding member defines a first holding member chamber and a second holding member chamber. The first holding member chamber has a first pressure when a fluid is disposed within the first holding member chamber. The second holding member chamber has a second pressure when a fluid is disposed within the second holding member chamber. The second pressure is different than the first pressure.

15 Claims, 38 Drawing Sheets

(56) References Cited

U.S. PATENT DOCUMENTS

| 6,060,306 | A | * | 5/2000 | Flatt | ................. | C12M 23/34 |
|---|---|---|---|---|---|---|
| | | | | | | 435/297.2 |
| 8,507,266 | B2 | | 8/2013 | Welter et al. | | |
| 2004/0191906 | A1 | * | 9/2004 | Holzer | ................. | C12M 35/04 |
| | | | | | | 435/383 |

OTHER PUBLICATIONS

PCT Search Report and Written Opinion, Application No. PCT/US2019/060429, dated Mar. 25, 2020.
Australian Examination report No. 2, Application No. 2019377857, dated Jan. 19, 2023.

\* cited by examiner

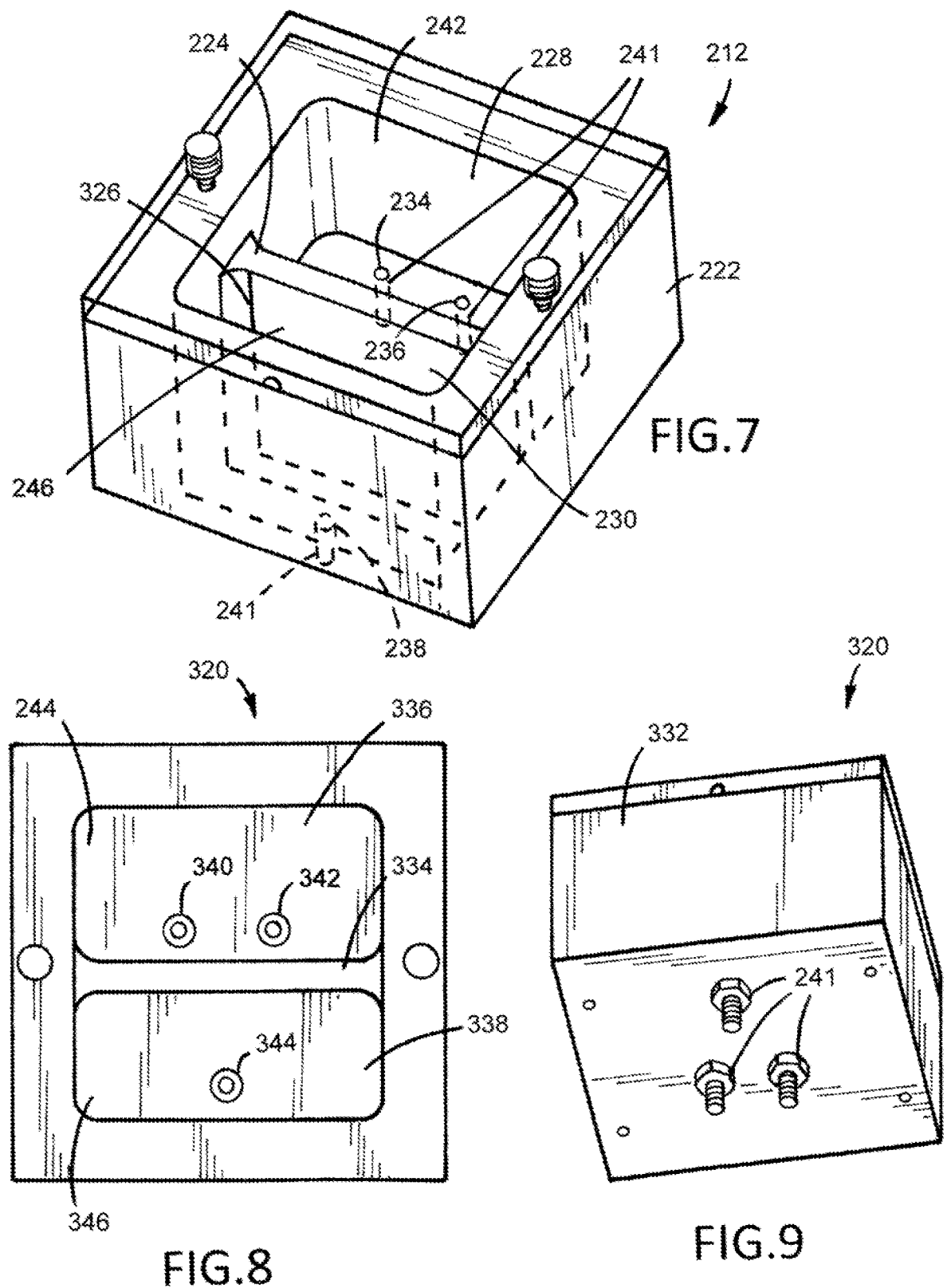

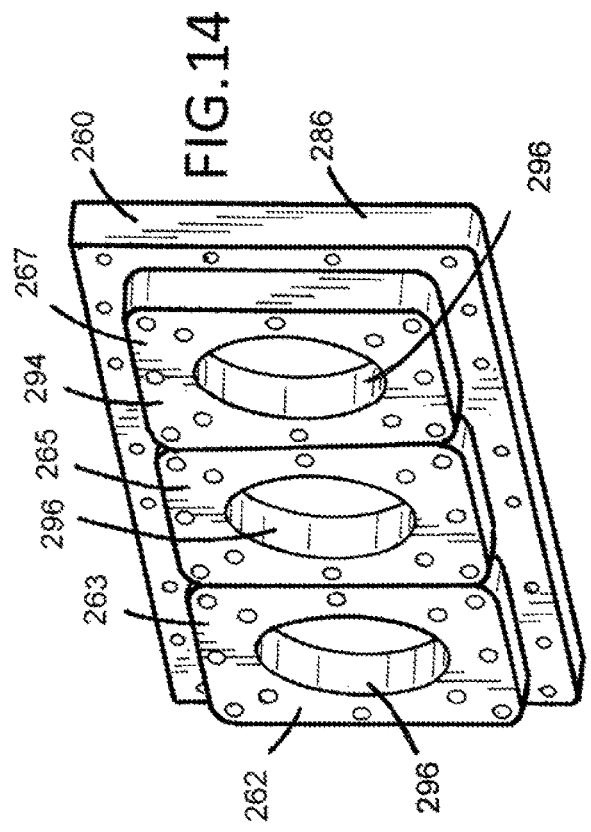
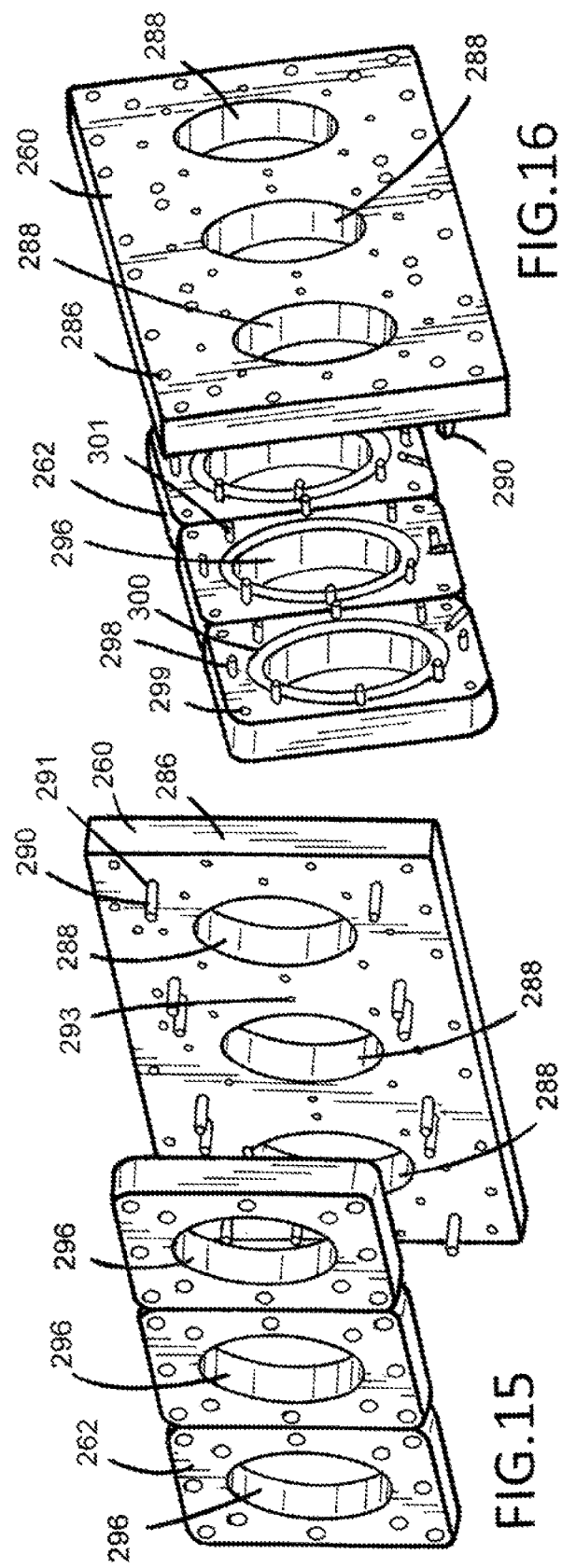

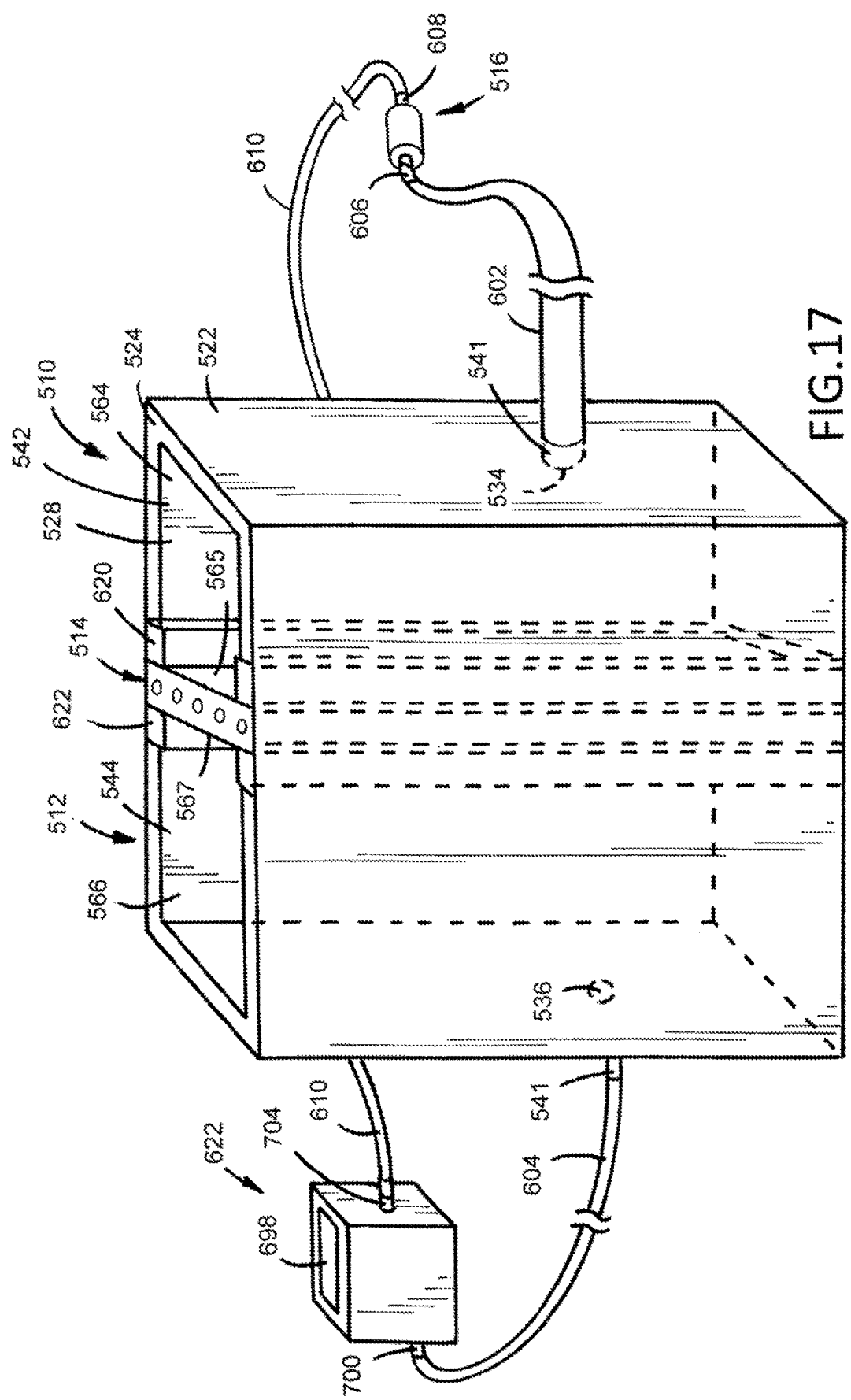

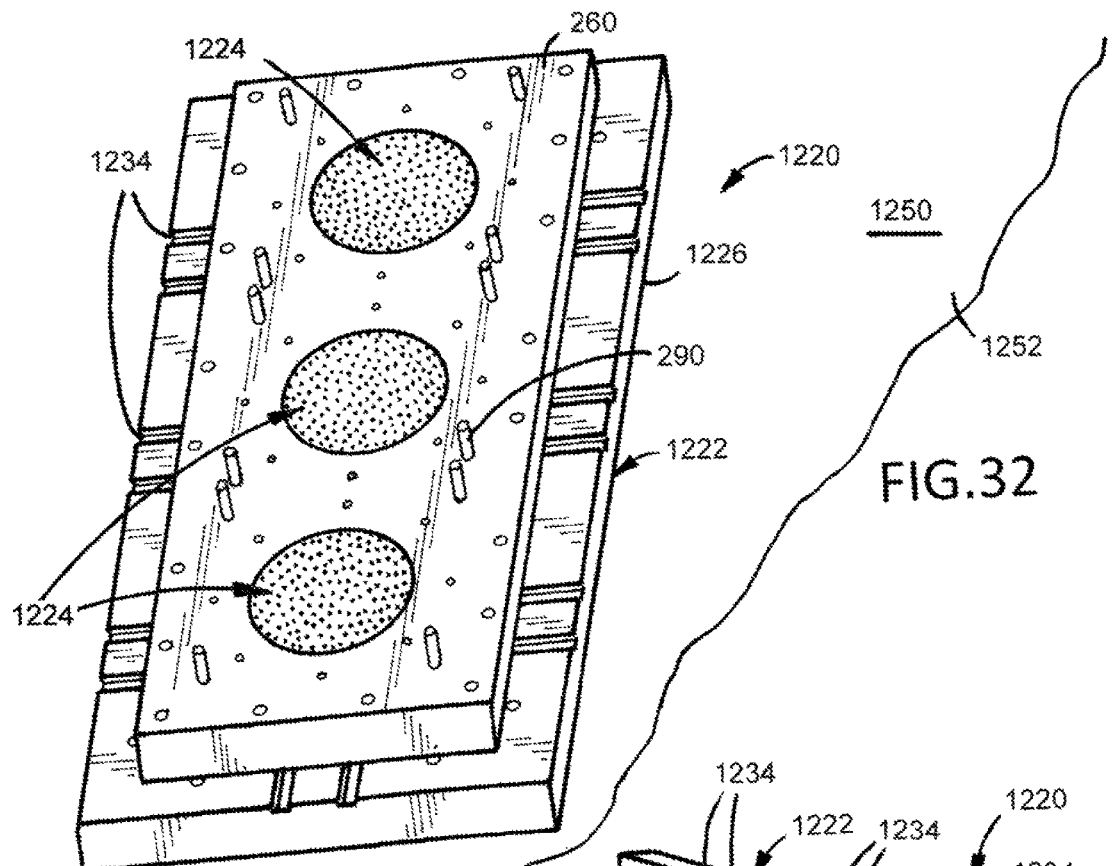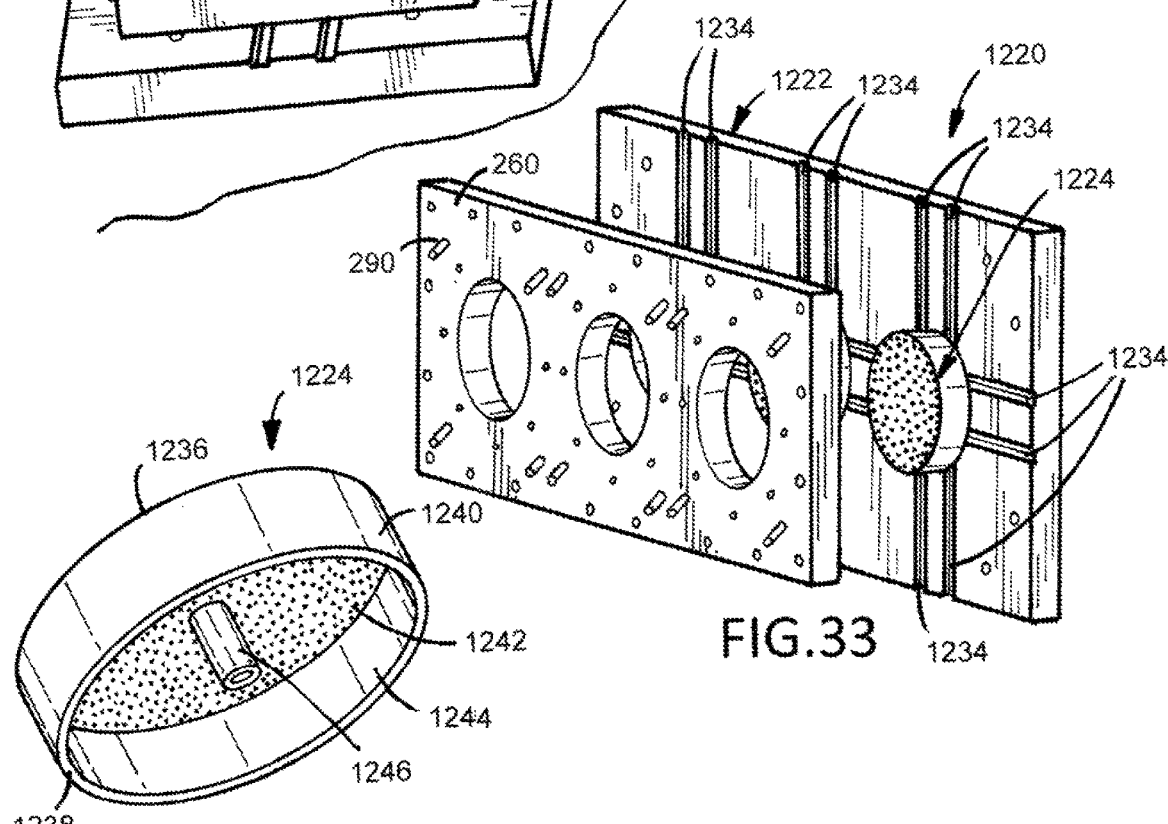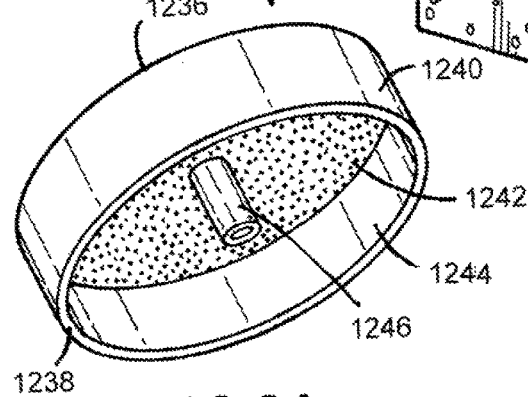

DIFFERENTIAL PRESSURE MATERIAL PROCESSING SYSTEMS, APPARATUS, METHODS, AND PRODUCTS

CROSS-REFERENCE TO RELATED APPLICATION

This application claims the benefit of U.S. Provisional Application No. 62/757,783, filed on Nov. 9, 2018. The entire disclosure of this related application is hereby incorporated by reference into this disclosure.

FIELD

The disclosure relates generally to the field of material processing for manufacturing and/or assembly environments. More particularly, the disclosure relates to differential pressure material processing systems, apparatus, methods, and products. Specific examples described herein relate to differential pressure tissue fixation useful in the manufacture of medical devices.

BACKGROUND

Generally, tissue fixation for medical products is utilized to preserve the properties of the tissue, such as mechanical properties, through cross-linking during chemical fixation, for example, and to render the tissue relatively inert for use in implantation. Currently, differential pressure processing systems are used to fix heart valves that include a tubular wall and valve leaflets. These systems allow fluid to flow through the tubular wall and past the valve during the fixation process, which presents significant drawbacks for processing other types of tissue. For example, current systems are passive and fail to maintain control of the forces exerted on the tissue over time or a constant differential pressure across the tissue, which may leak or diffuse fluid during processing as a result of the inherent permeability of the tissue. In addition, current systems fail to provide a mechanism for processing sheets of tissue and for attaching a sheet of tissue to the system without causing deformation during attachment. Highly distensible and low thickness tissues pose unique challenges related to attachment of the tissue to a system for processing. Specifically, due to the very low forces required to cause deformation of these tissues, large deformations can be imparted onto the tissue during attachment, which can impact the mechanical behavior of the tissue after processing. Tissues with highly consistent mechanical properties are desired for medical device manufacturing. Deformations imparted during attachment, uniform or not, can alter the internal stress and strain state and change the collagen configuration of the tissue during processing, often in an unpredictable or unknown manner, resulting in a less constituent material after processing.

Therefore, a need exists for new and useful differential pressure material processing systems, apparatus, methods, and products.

SUMMARY OF SELECTED EXAMPLE EMBODIMENTS

Various differential pressure material processing systems, apparatus, methods, and products are described herein.

An example differential pressure material processing system for processing tissue using a fluid comprises a tank and a holding member. The tank defines a first portion and a second portion. The holding member includes a loading member and a clamping member releasably attached to the loading member. The holding member defines a first holding member chamber in fluid communication with the first portion of the tank, a second holding member chamber in fluid communication with the second portion of the tank, and a passageway in fluid communication with the first holding member chamber and the second holding member chamber. The fluid has a first pressure when disposed within the first portion of the tank and the first holding member chamber. The fluid has a second pressure when disposed within the second portion of the tank and the second holding member chamber. The second pressure is different than the first pressure. The tissue is disposed between the loading member and the clamping member such that a portion of the tissue spans an entire cross-section of the passageway to obstruct the passageway defined by the holding member.

An example method of loading a sheet of tissue comprises: positioning a sheet of tissue on a loading member such that a portion of the sheet of tissue is separated from the loading member by a fluid layer disposed between the portion of the sheet of tissue and the loading member; adjusting the position of the sheet of tissue; positioning a clamping member on the loading member; and releasably attaching the clamping member to the loading member such that the sheet of tissue is disposed between the clamping member and the loading member and contacts the loading member.

An example method of processing tissue comprises: adjusting the position of a first tank relative to a second tank and a holding member along a vertical axis, the holding member has tissue disposed between a loading member and a clamping member; connecting the first tank to a pump such that the first portion of the first tank is in fluid communication with the pump; connecting the second tank to the pump such that the first portion of the second tank is in fluid communication with the pump; connecting the first tank to a holding member such that the first portion of the first tank is in fluid communication with the holding member; connecting the second tank to the holding member such that the first portion of the second tank is in fluid communication with the holding member; connecting the first tank to a reservoir such that the first tank is in fluid communication with the reservoir; connecting the second tank to the reservoir such that the second tank is in fluid communication with the reservoir; connecting the pump to the reservoir such that the pump is in fluid communication with the reservoir; introducing fluid into the tank; opening a vent on the loading member; opening a vent on the clamping member; activating the pump; introducing fluid into reservoir while the pump is in an on state; closing the vent on the loading member; closing the vent on the clamping member; maintaining the pump in the on state for a period of time such that a differential pressure is applied to the tissue; deactivating the pump; draining the holding member; disassembling the holding member; removing the clamping member; removing the tissue from the loading member; placing the tissue in a fluid for a period of time.

Additional understanding of the example differential pressure material processing systems, apparatus, methods, and products can be obtained by review of the detailed description, below, and the appended drawings.

BRIEF DESCRIPTION OF THE DRAWINGS

FIG. 7 is a perspective view of the first tank of the system illustrated in FIG. 6.

FIG. 8 is a top view of the second tank of the system illustrated in FIG. 6.

FIG. 9 is a perspective view of the second tank illustrated in FIG. 8.

FIG. 14 is a perspective view of the loading member and the clamping member of the system illustrated in FIG. 6.

FIG. 15 is an exploded perspective view of the loading member and the clamping member illustrated in FIG. 14.

FIG. 16 is another exploded perspective view of the loading member and the clamping member illustrated in FIG. 14.

FIG. 17 is a perspective view of another example differential pressure material processing system.

FIG. 32 illustrates an example loading member disposed on an example loading tool.

FIG. 33 is an exploded view of the loading member and loading tool illustrated in FIG. 32.

FIG. 34 is a perspective view of the cap of the loading tool illustrated in FIG. 32.

DETAILED DESCRIPTION

Figure 1:
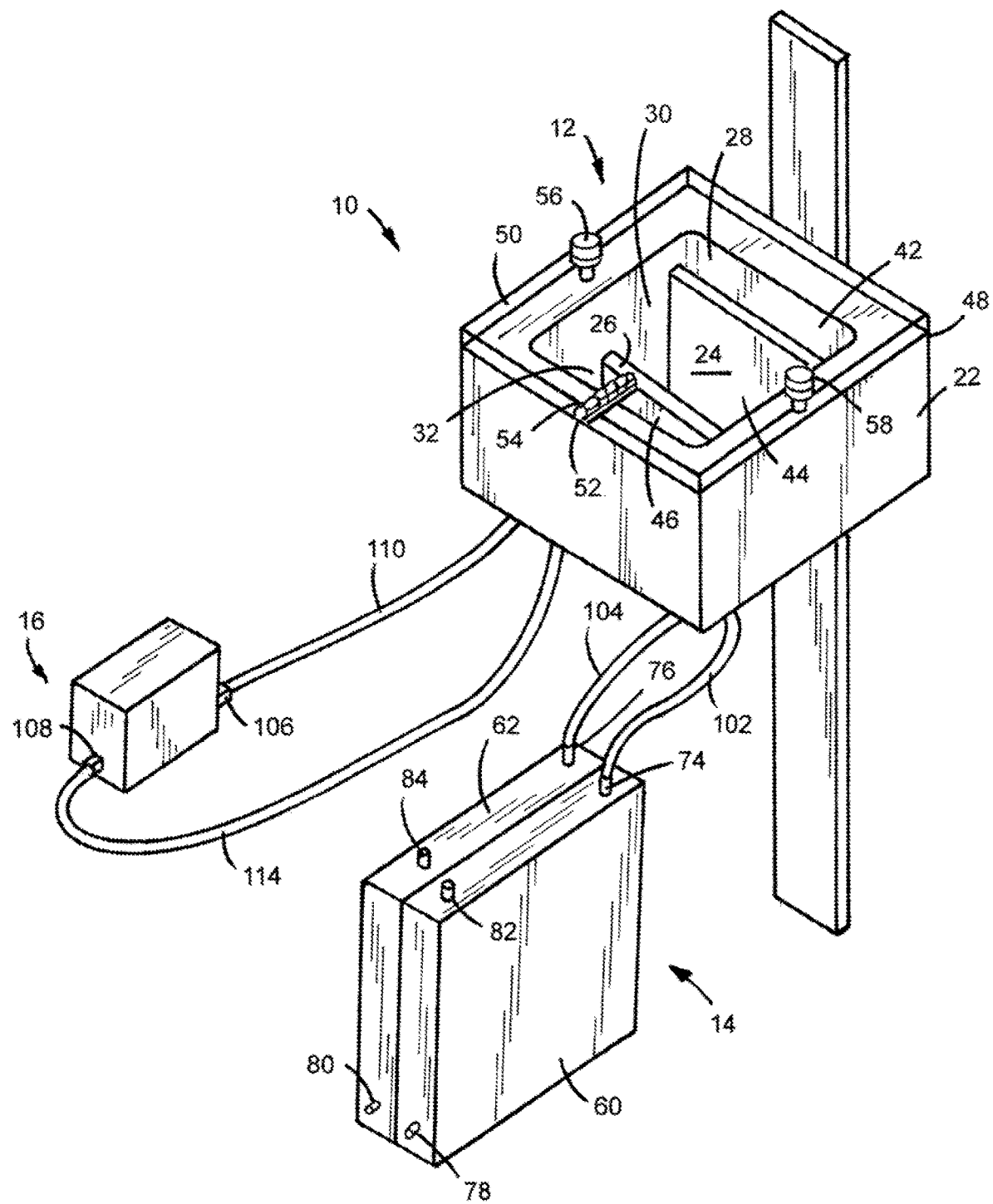
FIG. 1 is a perspective view of an example differential pressure material processing system.
Figure 2:
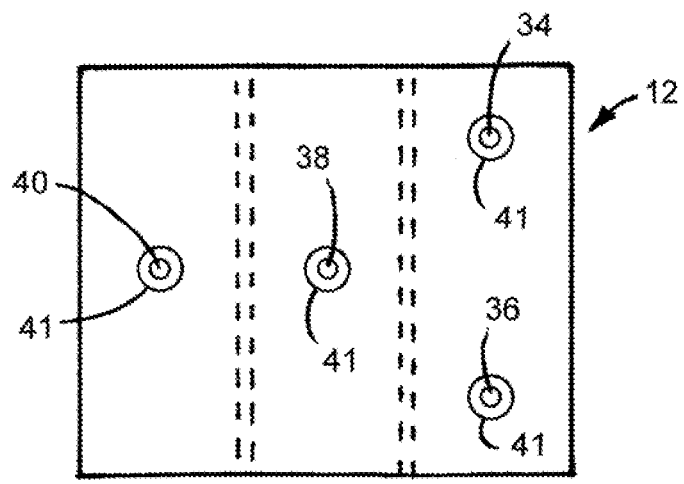
FIG. 2 is a bottom view of the tank of the system illustrated in FIG. 1.
Figure 3:
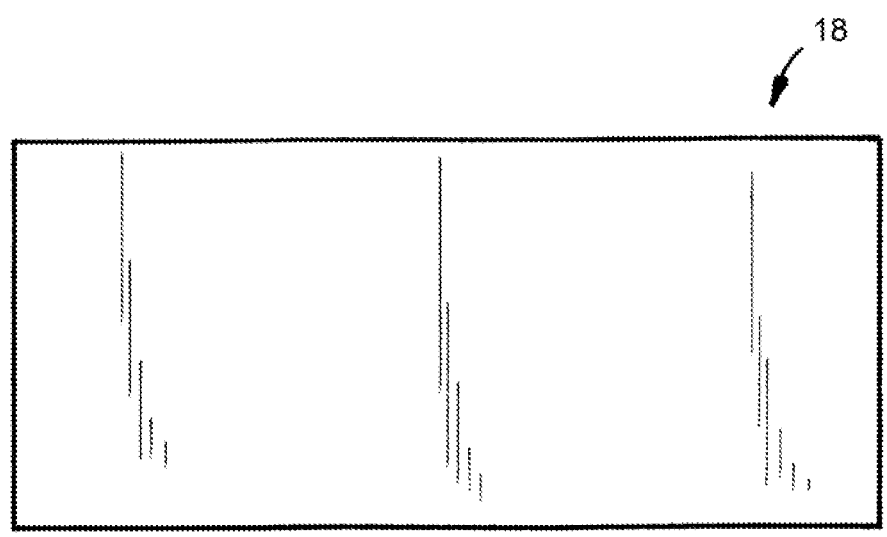
FIG. 3 is a front view of a sheet of tissue that can be positioned within the holding member of the system illustrated in FIG. 1.

The following detailed description and the appended drawings describe and illustrate various example embodiments of differential pressure material processing systems, apparatus, methods, and products. The description and illustration of these examples are provided to enable one skilled in the art to make and use a differential pressure material processing system, an apparatus, to practice a method of using a differential pressure material processing system, and to create a product. They are not intended to limit the scope of the claims in any manner.

FIGS. 1, 2, 3, 4, and 5 illustrate a first example differential pressure material processing system 10 that can be used to process tissue using a fluid. The differential pressure material processing system 10 includes a tank 12, a holding member 14, a pump 16, and a sheet of tissue 18 disposed within the holding member 14.

The tank 12 has a main body 22 that defines a first non-permeable wall 24, a second non-permeable wall 26, a first recess 28, a second recess 30, a third recess 32, a first passageway 34 in communication with the first recess 28, a second passageway 36 in communication with the first recess 28, a third passageway 38 in communication with the second recess 30, and a fourth passageway 40 in communication with the third recess 32. The first recess 28 defines a first portion of the tank 12. When fluid is disposed within the first recess 28 to a level at which the fluid has a height greater than the height of the first non-permeable wall 24 and the fluid flows into the second recess 30 the fluid has a first pressure creating a high-pressure portion 42 of the tank 12. The second recess 30 defines a second portion of the tank 12. When fluid is disposed within the second recess 30 to level at which the fluid has a height greater than the height of the second non-permeable wall 26 and the fluid flows into the third recess 32 the fluid has a second pressure that is less than the first pressure creating a low-pressure portion 44 of the tank 12. The third recess 32 defines a tank reservoir 46 that is in fluid communication with the inlet port 108 of the pump 16, as described in more detail herein. The third recess 32 defines a third portion of the tank 12. Each of the first passageway 34 and the second passageway 36 extends through the main body 22 and provides access between the first recess 28 and an environment exterior to the first recess 28. The third passageway 38 extends through the main body 22 and provides access between the second recess 30 and an environment exterior to the second recess 30. The fourth passageway 40 extends through the main body 22 and provides access between the third recess 32 and an environment exterior to the third recess 32. An attachment member 41 is attached to the tank 12 within each of the passageways 34, 36, 38, and 40 and provides a mechanism to attach the tank 12 to another component, such as the holding member 14 and/or pump 16, as described in more detail herein.

When a fluid is disposed within the recesses 28, 30, 32 defined by the tank 12, the pressure differential of the fluid within the first and second recesses 28, 30 can be controlled by manipulating the height of the first and second impermeable walls 24, 26. This can be accomplished by calculating a desired pressure differential and configuring the first and second impermeable walls 24, 26 accordingly. For example, the height of an impermeable wall included in a tank can be manipulated such that modifications to the pressure differential can be imparted on the system by increasing or decreasing the height of an impermeable wall. This can be accomplished by forming an impermeable wall of multiple sections and adding or removing sections and/or by forming a portion of an impermeable wall as a telescoping member.

In the illustrated embodiment, the tank 12 includes a cap 48 that is releasably attached to the main body 22 of the tank 12. The cap 48 has a main body 50 that defines a vent 52. A vent 52 can comprise any suitable structure capable of providing fluid communication between the recesses defined by the tank 12 and an environment exterior to the tank 12. In the illustrated embodiment, the vent 52 comprises a recess 54 that extends from a first edge of the cap 48 into the main body 12 and toward an opposing edge of the cap 48. However, alternative embodiments can include any suitable vent or can omit the inclusion of a cap. Optionally, in embodiments that include a vent, a vent can be in fluid communication with a filter system and/or a filter could be disposed within the vent to accomplish a closed, or substantially closed, system that can prevent contaminants or particulate from entering the system and provide a mechanism to filter chemical fumes.

A cap can be releasably attached to a main body of a tank using any suitable technique or method of attachment and selection of a suitable technique or method of attachment between a cap and a tank can be based on various considerations, including the material that forms the cap and/or tank. Examples of techniques and methods of attachment considered suitable between a cap and a tank include using threaded connections, snap fit attachments, using one or more connectors, one or more mating slots and projections, one or more sealed unions, tapered attachments, adhesives, and any other technique or method of attachment considered suitable for a particular embodiment. In the illustrated embodiment, the cap 48 is attached to the main body 22 of the tank 12 using two threaded screws 56, 58. Alternatively, a cap can be positioned on a tank and not be releasably attached to the tank. For example, one or more guide members (e.g., guide pins, guide holes) can be used to position a cap on a tank.

While the tank 12 has been illustrated as including a first non-permeable wall 24 and a second non-permeable wall 26, a tank can include any suitable number of walls that have any suitable permeability and selection of a suitable number of walls to include in a tank of a differential pressure material processing system and of a suitable permeability for each wall can be based on various considerations, including the intended use of the tank. Examples of numbers of walls considered suitable to include in a tank include one, at least one, two, a plurality, three, four, five, more than five, and any other number considered suitable for a particular embodiment. In embodiments in which a wall is permeable, the wall can have any suitable degree of permeability and can be based on the desired differential pressure intended to be achieved.

The holding member 14 includes a loading member 60, a clamping member 62 releasably attached to the loading member 60, and defines a first holding member chamber 64, a second holding member chamber 66, a plurality of passageways 68, 70, 72 in communication with the first holding member chamber 64 and second holding member chamber 66, a first input port 74, a second input port 76, a first drain 78, a second drain 80, a first vent 82, and a second vent 84.

In the illustrated embodiment, the loading member 60 has a main body 86 that defines the first holding member chamber 64, a first portion 88 of each passageway of the plurality of passageways 68, 70, 72, the first input port 74, the first drain 78, the first vent 82, a first guide member 90, and a support member 92 spanning each passageway of the plurality of passageways 68, 70, 72. In the illustrated embodiment, the support member 92 is perforated.

In the illustrated embodiment, the clamping member 62 has a main body 94 that defines the second holding member chamber 66, a second portion 96 of each passageway of the plurality of passageways 68, 70, 72, the second input port 76, the second drain 80, the second vent 84, a second guide member 98, and a plurality of sealing members 100. The first portion 88 of each passageway of the plurality of passageways 68, 70, 72 and the second portion 96 of each passageway of the plurality of passageways 68, 70, 72 cooperatively define each passageway of the plurality of passageways 68, 70, 72 of the holding member 14. A sealing member of the plurality of sealing members 100 surrounds each portion of the passageway of the plurality of passageways 68, 70, 72 defined by the clamping member 62 and provides a mechanism to seal the tissue 18 between the loading member 60 and the clamping member 62 (e.g., prevent leakage around the sealing member 100) and maintain the position of the tissue 18 during use.

The first input port 74 provides access between the first holding member chamber 64 and an environment exterior to the first holding member chamber 64 and includes an attachment member 75 to provide attachment to an elongate tubular member, as described in more detail herein. The second input port 76 provides access between the second holding member chamber 66 and an environment exterior to the second holding member chamber 66 and includes an attachment member 77 to provide attachment to an elongate tubular member, as described in more detail herein. The first drain 78 provides access between the first holding member chamber 64 and an environment exterior to the first holding member chamber 64 and includes a valve 79 that is moveable between an open configuration and a closed configuration to allow the first holding member 64 to be drained, as described in more detail herein. The second drain 80 provides access between the second holding member chamber 66 and an environment exterior to the second holding member chamber 66 and includes a valve 81 that is moveable between an open configuration and a closed configuration to allow the second holding member 66 to be drained, as described in more detail herein. The first vent 82 provides access between the first holding member chamber 64 and an environment exterior to the first holding member chamber 64 and includes a valve 83 moveable between an open configuration and a closed configuration. The second vent 84 provides access between the second holding member chamber 66 and an environment exterior to the second holding member chamber 66 and includes a valve 85 moveable between an open configuration and a closed configuration.

An attachment member included in a differential pressure material processing system can include any suitable feature, device, or component capable of providing attachment between two components and selection of a suitable attachment member can be based on various considerations, including the type of attachment desired between two components. Examples of suitable attachment members include any suitable connector and/or adapter, threaded connectors, conical connectors (e.g., cones, sockets), connectors with barbed ends, combinations of the attachment members described herein, adhesives, and any other connector and/or adapter considered suitable for a particular embodiment. In the illustrated embodiment, each of the attachment members comprises a connector with a barbed end that is sized and configured to be received within a passageway defined by an elongate tubular member, as described in more detail herein. A valve included in a differential pressure material processing system can include any suitable feature, device, or component capable of moving between an open configuration and a closed configuration and selection of a suitable valve can be based on various considerations, including the material forming a feature, device, or component to which a valve is attached. Examples of suitable valves include butterfly valves, gate valves, globe valves, ball valves, three-way valves, stopcocks, and any other valve considered suitable for a particular embodiment. In the illustrated embodiment, each of the valves comprises a ball valve.

Figure 4:
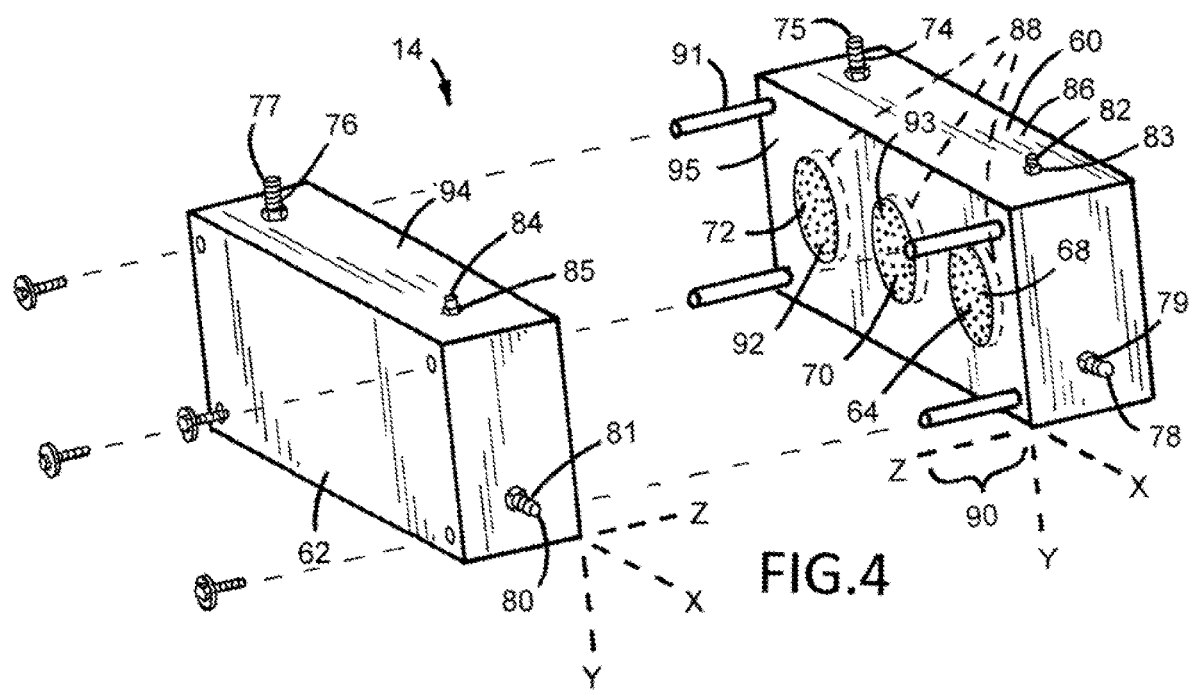
FIG. 4 is an exploded perspective view of the holding member of the system illustrated in FIG. 1.
Figure 5:
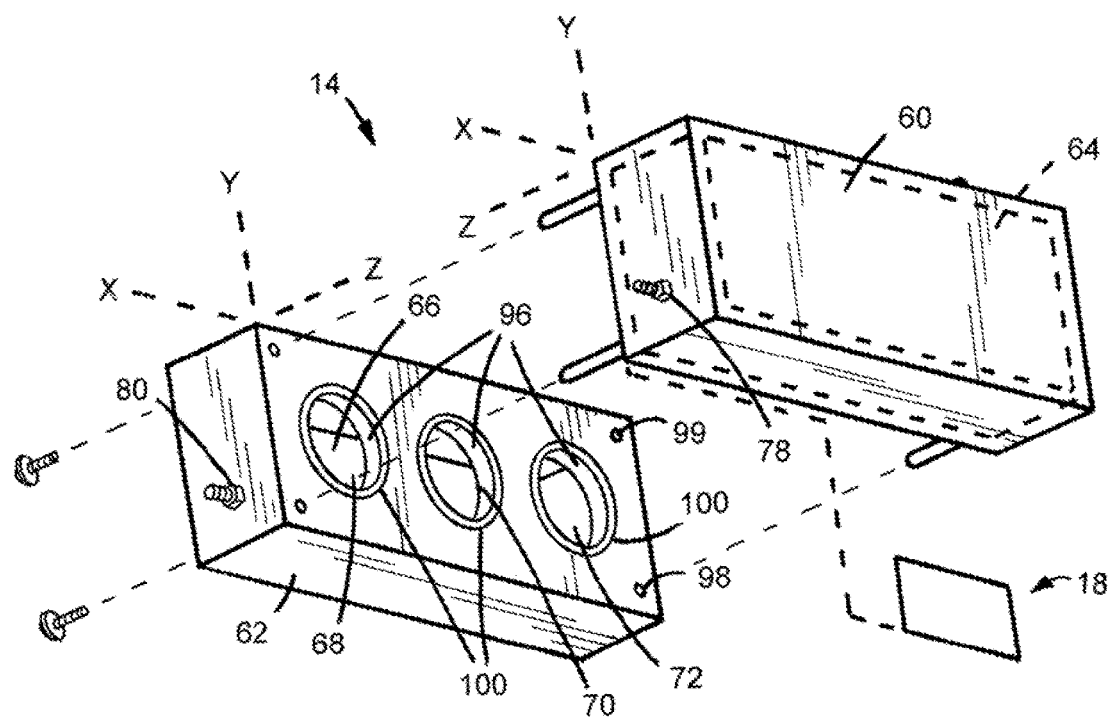
FIG. 5 is an exploded perspective view of the holding member and sheet of tissue of the system illustrated in FIG. 1.
Figure 6:
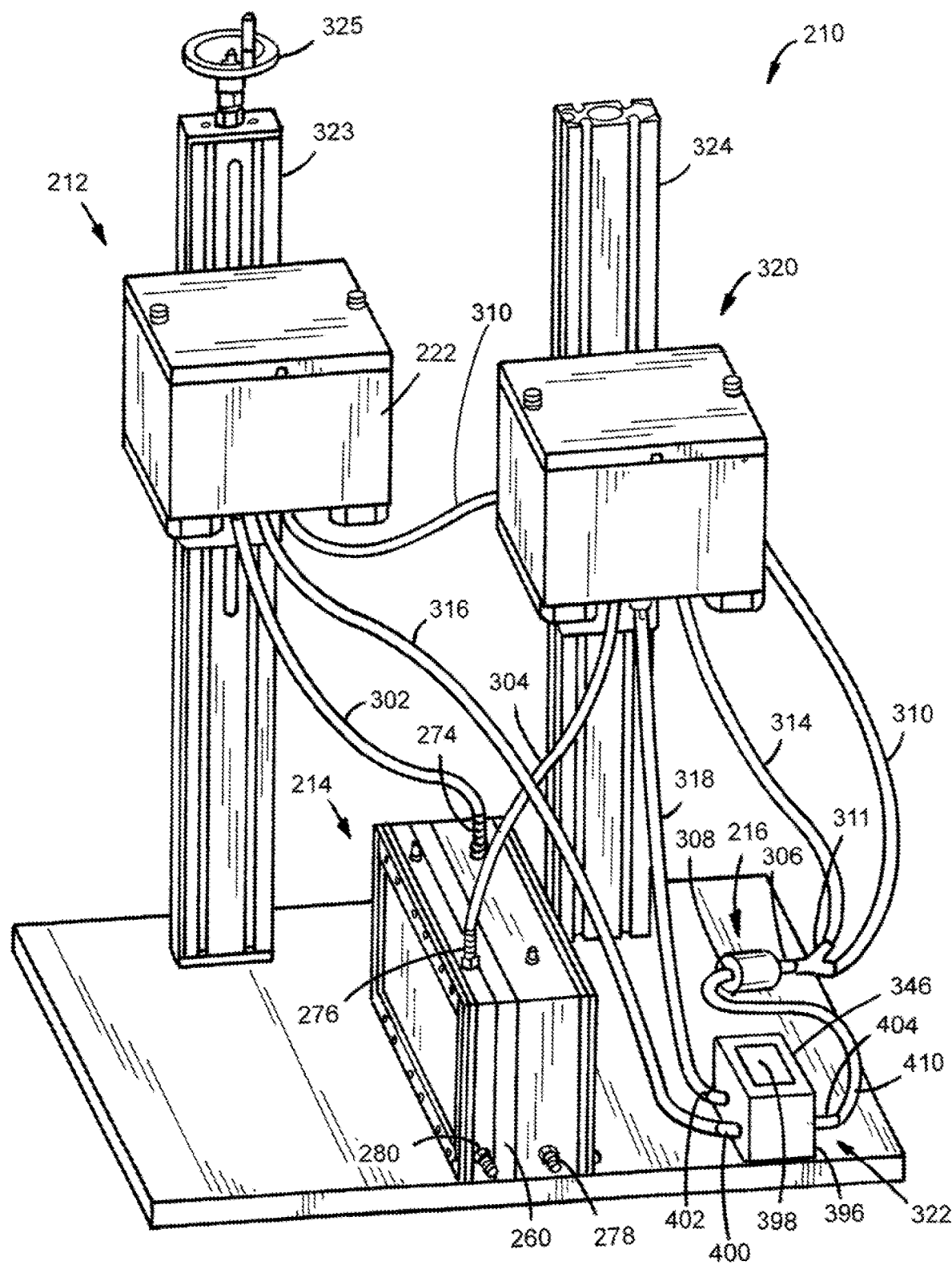
FIG. 6 is a perspective view of another example differential pressure material processing system.

A first guide member and a second guide member included on a holding member can include any suitable feature, device, or component capable of maintaining the position of a loading member relative to a clamping member along an x-axis and a y-axis, as shown in FIGS. 4 and 5, while the clamping member is being attached to the loading member. For example, a loading member can include a first guide member and the clamping member can include a second guide member that mates with the first guide member to prevent movement of the loading member relative to the clamping member along the x-axis and the y-axis during releasable attachment of the clamping member to the loading member. It is considered advantageous to include a first guide member and a second guide member to reduce, or eliminate, any unintentional deformation and/or stress imparted on tissue positioned between a loading member and a clamping member. Selection of suitable first and second guide members to include on a holding member can be based on various considerations including the intended use of the holding member. Examples of suitable guide members include a plurality of guide pins and a plurality of guide holes, a first track that is received by a second track, use of one or more magnets, combinations of the guide members described herein, and any other guide member considered suitable for a particular embodiment. In the illustrated embodiment, the first guide member 90 comprises a plurality of guide pins 91 and the second guide member 98 comprises a plurality of guide holes 99. A guide pin of the plurality of guide pins 91 is disposed within a guide hole of the plurality of guide holes 99 when the holding member 14 is assembled. Each guide hole of the plurality of guide holes 99 is sized and configured to receive a guide pin of the plurality of guide pins 91.

A support member included on a loading member can comprise any suitable feature, device, or component capable of providing support to tissue intended to be disposed on the member and/or permeability across the material such that a first portion of a passageway defined by a loading member is in fluid communication with a second portion of a passageway defined by a clamping member when tissue is not disposed between the loading member and the clamping member. For example, a support member can be formed by defining a plurality of openings within a material that forms a loading member, attaching a material that defines a plurality of openings to a loading member, or using any other suitable technique or method. A support member included in a differential pressure material processing system can have any suitable rigidity. For example, a support member can have a rigidity that does not deform under the differential pressures applied during processing. In the illustrated embodiment, the support member 92 comprises a plurality of openings 93 defined in the material that forms the loading member 60 such that the remainder of the material that defines the loading member 60 creates a continuous, uninterrupted, surface 95 for positioning tissue, as described in more detail herein. In alternative embodiments, surface 95 of a loading member could be curved and a clamping member could define a mating surface to assist with positioning tissue on a loading member in a resting state, as described in more detail herein.

A sealing member 100 can comprise any suitable feature, device, or component capable of sealing tissue between a loading member and a clamping member when the loading member is releasably attached to the clamping member. Selection of a suitable sealing member to include in a holding member can be based on various considerations, including the intended use of the holding member. Examples of suitable sealing members include forming a portion of a loading member or clamping member as a raised projection, forming a recess in a loading member and/or a clamping member and positioning a gasket (e.g., O-ring) within the recess, and any other sealing member considered suitable for a particular embodiment. In the illustrated embodiment, the sealing member comprises an O-ring disposed within a recess defined by the clamping member 62. While a sealing member of the plurality of sealing members 100 has been illustrated as surrounding each portion of the passageway of the plurality of passageways 68, 70, 72 defined by the clamping member 62, alternative embodiments can include a plurality of sealing members such that a sealing member of the plurality of sealing members surrounds each portion of a passageway of a plurality of passageways defined by a loading member. Alternatively, a holding member can include a first plurality of sealing members on a clamping member, as described herein, and a second plurality of sealing members on a loading member, as described herein, that are positioned such that a sealing member of the clamping member mates with a sealing member of the loading member, or such that a sealing member of the clamping member does not contact a sealing member of the loading member, when the clamping member is releasably attached to the loading member.

A loading member and a clamping member can be releasably attached to one another using any suitable technique or method of attachment and selection of a suitable technique or method of attachment between a loading member, or portions of a loading member, and a clamping member, or portions of a clamping member, can be based on various considerations, including the material that forms the loading member and/or the clamping member. Examples of techniques and methods of attachment considered suitable between a loading member, or portions of a loading member, and a clamping member, or portions of a clamping member, include using threaded connections, snap fit attachments, using one or more connectors, one or more mating slots and projections, one or more sealed unions, tapered attachments, external clamps, pneumatic clamping mechanisms, adhesives, and any other technique or method of attachment considered suitable for a particular embodiment. In the illustrated embodiment, the loading member 60 is releasably attached to the clamping member 62 using four threaded screws.

While the holding member 14 has been illustrated as defining a plurality of passageways 68, 70, 72, a holding member can define any suitable number of passageways having any suitable diameter and selection of a suitable number of passageways to define on a holding member and of a suitable diameter for each passageway can be based on various considerations, including the intended use of a holding member and/or the total number of sheets of material intended to be processed by the differential pressure material processing system. Examples of numbers of passageways considered suitable for a holding member to define include one, at least one, two, a plurality, three, four, five, more than five, and any other number considered suitable for a particular embodiment. Examples of diameters considered suitable for each passageway defined by a holding member, or one or more passageways defined by a holding member, include diameters equal to, greater than, less than, or about 50 millimeters, 60 millimeters, 63 millimeters, 70 millimeters, between about 50 millimeters and about 70 millimeters, diameters that are less than the length, width, and/or diameter of a sheet of tissue intended to be disposed between a loading member and a clamping member, diameters that define a passageway that has an area that is less than the area of a sheet of tissue intended to be disposed between a loading member and a clamping member, and any other diameter considered suitable for a particular embodiment.

In the illustrated embodiment, the first recess 28 is in fluid communication with the first holding member chamber 64 such that the high-pressure portion 42 is in fluid communication with the first holding member chamber 64 and the second recess 30 is in fluid communication with the second holding member chamber 66 such that the low-pressure portion 44 is in fluid communication with the second holding member chamber 66. The fluid within the first holding member chamber 64 has a first pressure and the fluid within the second holding member chamber 66 has a second pressure that is different than the first pressure. In the illustrated embodiment, the first pressure is greater than the second pressure. Any suitable technique or method of accomplishing fluid communication between a recess and a holding member chamber can be utilized and selection of a suitable technique or method can be based on various considerations, including the type of tissue intended to be positioned within a holding member. Examples of techniques and methods considered suitable include using one or more tubular members, manifolds, forming the various features as a single, integrated, unit, and any other technique or method considered suitable for a particular embodiment. In the illustrated embodiment, the first recess 28 is in fluid communication with the first holding member chamber 64 using a first elongate tubular member 102 and the second recess 30 is in fluid communication with to the second holding member chamber 64 using a second elongate tubular member 104. The first elongate tubular member 102 has a first end in fluid communication with the first passageway 34 and a second end in fluid communication with the first input port 74 of the holding member 14. The second elongate tubular member 104 has a first end in fluid communication with the third passageway 38 and a second end in fluid communication with the second input port 76 of the holding member 14.

The pump 16 includes an outlet port 106, an inlet port 108, and has an on state and an off state. The outlet port 106 is in fluid communication with the first recess 28 such that the high-pressure portion 42 is in fluid communication with the pump 16 and the inlet port 108 is in fluid communication with the tank reservoir 46. Any suitable technique or method of connecting a recess to a pump can be utilized and selection of a suitable technique or method can be based on various considerations, including the type of tissue intended to be positioned within a holding member. Examples of techniques and methods considered suitable include using one or more tubular members, manifolds, forming the various features as a single, integrated unit, and any other technique or method considered suitable for a particular embodiment. In the illustrated embodiment, the outlet port 106 is in fluid communication with the first recess 28 using a third elongate tubular member 110 and the inlet port 108 is in fluid communication with the third recess 32 using a fourth elongate tubular member 114. The third elongate tubular member 110 has a first end in fluid communication with the outlet port 106 of the pump 16 and a second end in fluid communication with the second passageway 36 defined by the main body 22 of the tank 12. The fourth elongate tubular member 114 has a first end in fluid communication with the inlet port 108 and a second end in fluid communication with the fourth passageway 40 defined by the main body 22 of the tank 12.

Any suitable pump can be included in a differential pressure material processing system and selection of a suitable pump to include in a differential pressure material processing system can be based on various considerations, including the intended use of the system. Examples of pumps considered suitable to include in a differential pressure material processing system include peristaltic pumps, sealed pumps, and any other pump considered suitable for a particular embodiment.

The tissue 18 is disposed within the holding member 14 between the loading member 60 and the clamping member 62 such that each passageway of the plurality of passageways 68, 70, 72, is obstructed by a portion of the tissue 18 that spans the entire cross section of the passageway defined by the loading member 60 and a clamping member 62. Depending on the type of processing being completed on the tissue, the tissue 18 can be disposed within the holding member 14 between the loading member 60 and the clamping member 62 such that each passageway of the plurality of passageways 68, 70, 72, is obstructed by a portion of the tissue 18 that spans the entire cross section of the passageway defined by the loading member 60 and a clamping member 62 prior to the application of differential pressure (e.g., when the pump 16 is in the off state). Alternatively, or in combination with being positioned prior to the application of differential pressure, the tissue 18 can be disposed within the holding member 14 between the loading member 60 and the clamping member 62 such that each passageway of the plurality of passageways 68, 70, 72, is obstructed by a portion of the tissue 18 that spans the entire cross section of the passageway defined by the loading member 60 and a clamping member 62 during the application of differential pressure (e.g., when the pump 16 is in the on state). Alternatively, or in combination with being positioned prior to and/or during the application of differential pressure, the tissue 18 can be disposed within the holding member 14 between the loading member 60 and the clamping member 62 such that each passageway of the plurality of passageways 68, 70, 72, is obstructed by a portion of the tissue 18 that spans the entire cross section of the passageway defined by the loading member 60 and a clamping member 62 subsequent to the application of differential pressure (e.g., when the pump 16 is in the off state). In the illustrated embodiment, the tissue 18 comprises a single piece, or sheet, of tissue 120.

While the differential pressure material processing system 10 has been illustrated as including a sheet of tissue 18, the material processed using a differential pressure material processing system, such as those described herein, can comprise any suitable material. Selection of a suitable material to process using a differential pressure material processing system can be based on various considerations, including the intended use of the material subsequent to processing. Examples of suitable materials to process using a differential pressure material processing system include natural materials, allogeneic materials, xenogeneic materials, synthetic materials, and combinations of natural and synthetic materials. Examples of suitable natural materials include extracellular matrix (ECM) materials, such as small intestine submucosa (SIS), and other bioremodelable materials, such as bovine pericardium. Other examples of suitable ECM materials that can be used include stomach submucosa, liver basement membrane, urinary bladder submucosa, tissue mucosa, and dura mater. Other examples of suitable natural materials include renal capsule matrix, abdominal fascia, parenchyma, such as abdominal parenchyma, connective tissue, pulmonary or lung ligament, tissue laminates, and natural valve leaflets with or without adjacent vessel wall. Pleura is also considered a suitable natural material, including visceral pleura. Examples of suitable synthetic materials include polymeric materials, such as expanded polytetrafluoroethylene, polyurethane, polyurethane urea, polycarbonate, and polyesters.

While the differential pressure material processing system 10 has been illustrated as including a single sheet of tissue 18, a differential pressure material processing system can include any suitable number of sheets of material and selection of a suitable number of sheets of material to include in a system can be based on various considerations, including the type of processing being performed on the material. Examples of numbers of sheets of material considered suitable to include in a differential pressure material processing system include zero, one, at least one, two, a plurality, three, four, five, six, seven, eight, nine, ten, more than ten, and any other number considered suitable for a particular embodiment. For example, a differential pressure material processing system, such as those described herein, can omit the inclusion of a tissue, or material, such that the tissue, or material, is provided separately.

To complete processing of the tissue 18, such as fixation, a fluid is pumped into the tank 12 until the level of fluid reaches the top of the each of the first and second non-permeable walls 24, 26, the fluid travels into both the first holding member chamber 64 and the second holding member chamber 66, and is applied to the tissue 18. The recesses 28, 30 defined by the tank 12 maintain a constant, or substantially constant, head height and pressure differential across the tissue 18 when the fluid is constantly pumped into the tank 12 resulting in the tissue being processed under differential pressure. This is considered advantageous at least because it provides a mechanism for accounting for any tissue permeability, which would allow fluid to travel through the tissue from a first holding member chamber to a second holding member chamber.

Any suitable differential pressure can be applied to tissue being processed in a differential pressure material processing system, such as those described herein, and selection of a suitable differential pressure to apply to a tissue can be based on various considerations, including the type of tissue being processed and/or the process being completed on the tissue. Examples of suitable differential pressures considered suitable to apply to tissue being processed using a differential pressure material processing system, such as those described herein, include differential pressures that are equal to, less than, greater than, or about 0.25 millimeters of mercury, 0.5 millimeters of mercury, 1 millimeter of mercury, 1.5 millimeters of mercury, 1.75 millimeters of mercury, 5 millimeters of mercury, 10 millimeters of mercury, 20 millimeters of mercury, differential pressures that are greater than 1.75 millimeters of mercury, differential pressures that are between about 0.25 millimeters of mercury and about 20 millimeters of mercury, between about 0.25 millimeters of mercury and about 10 millimeters of mercury, between about 0.25 millimeters of mercury and about 5 millimeters of mercury, between about 0.25 millimeters of mercury and about 2 millimeters of mercury, between about 0.25 millimeters of mercury and about 1.75 millimeters of mercury, between about 0.25 millimeters of mercury and about 1.0 millimeters of mercury, between about 0.25 millimeters of mercury and about 0.5 millimeters of mercury, between about 0.25 millimeters of mercury and about 0.5 millimeters of mercury for visceral pleura tissue, and any other differential pressure considered suitable for a particular embodiment. In embodiments in which a higher differential pressure is applied to tissue (e.g., 10 millimeters of mercury), greater residual permanent deformation can be imparted into the tissue relative to embodiments in which a lower differential pressure (e.g., 1 millimeter of mercury) is applied to the tissue. In addition, in some embodiments, the application of differential pressure to tissue (e.g., 1 millimeter of mercury) results in more consistent mechanical behavior under biaxial loading relative to tissue that is not processed under differential pressure.

Any suitable fluid can be used to process tissue using a differential pressure material processing system, such as those described herein, and selection of a suitable fluid for use with a differential pressure material processing system can be based on various considerations, including the intended use of the tissue subsequent to processing. Examples of suitable fluids for use with a differential pressure material processing system include chemical fixatives, such as aldehydes, e.g., formaldehyde, glutaraldehyde, and formalin, and carbodiimides, such as ethyl dimethylaminopropyl carbodiimide, dicyclohexylcarbodiimide, solutions, tanning agents, tanning agents in a buffering solution, and any other fluid considered suitable for a particular embodiment. The differential pressure material processing systems described herein can be used to perform any suitable process on the tissue, such as fixation and/or sterilization.

FIGS. 6, 7, 8, 9, 10, 11, 12, 13, 14, 15, and 16 illustrate another example differential pressure material processing system 210. The differential pressure material processing system 210 is similar to the differential pressure material processing system 10 illustrated in FIGS. 1, 2, 3, 4, and 5 and described above, except as detailed below. The differential pressure material processing system 210 includes a first tank 212, a second tank 320, a holding member 214, a pump 216, a plurality of sheets of tissue 218 disposed within the holding member 214, and a reservoir 322.

In the illustrated embodiment, each of the first tank 212 and the second tank 320 is moveable vertically to adjust the differential pressure applied to the plurality of sheets of tissue 218 disposed within the holding member 214, as described in more detail herein. The first tank 212 is disposed relatively higher than the second tank 320 along a vertical axis. The first tank 212 is releasably attached to a first support post 323 and the second tank 320 is releasably attached to a second support post 324. Movement of a tank 212, 320 along a support post 323, 324 can be accomplished using any suitable technique or method. For example, in the illustrated embodiment, a crank 325 can be used to adjust the height of a tank along a support post. While support posts 232, 324 have been illustrated, a tank can alternatively be attached to any suitable structure capable of maintaining the position of the tank relative to a holding member during use. For example, a tank can be mounted to a wall or other vertical structure.

The first tank 212 has a main body 222 that defines a first non-permeable wall 224, a first recess 228, a second recess 230, a first passageway 234 in communication with the first recess 228, a second passageway 236 in communication with the first recess 228, and a third passageway 238 in communication with the second recess 230. The first recess 228 defines a first portion of the first tank 212. When fluid is disposed within the first recess 228 to a level at which the fluid has a height greater than the height of the first non-permeable wall 224 and the fluid flows into the second recess 230 the fluid has a first pressure creating a high-pressure portion 242 of the tank 212. The second recess 230 defines a tank reservoir 326 that is in fluid communication with the reservoir 322, as described in more detail herein. The second recess 230 defines a second portion of the first tank 212. Each of the first passageway 234 and the second passageway 236 extends through the main body 222 and provides access between the first recess 228 and an environment exterior to the first recess 228. The third passageway 238 extends through the main body 222 and provides access between the second recess 230 and an environment exterior to the second recess 230.

The second tank 320 has a main body 332 that defines a first non-permeable wall 334, a first recess 336, a second recess 338, a first passageway 340 in communication with the first recess 336, a second passageway 342 in communication with the first recess 336, and a third passageway 344 in communication with the second recess 338. The first recess 336 defines a first portion of the second tank 320. When fluid is disposed within the first recess 336 to a level at which the fluid has a height greater than the height of the first non-permeable wall 334 and the fluid flows into the second recess 338 the fluid has a second pressure that is less than the first pressure creating a low-pressure portion 244 of the tank 320. In the illustrated embodiment, the second tank 320 defines a low-pressure portion 244 as a result of its position relative to the first tank 212. The second recess 338 defines a tank reservoir 346 that is in fluid communication with the reservoir 322, as described in more detail herein. The second recess 338 defines a second portion of the second tank 320. Each of the first passageway 340 and the second passageway 342 extends through the main body 332 and provides access between the first recess 336 and an environment exterior to the first recess 336. The third passageway 344 extends through the main body 332 and provides access between the second recess 338 and an environment exterior to the second recess 338. An attachment member 241 is attached to the tanks 212, 320 within each of the passageways 234, 236, 238, 340, 342, and 344 to provide a mechanism to attach the tanks 212, 320 to another component, such as the holding member 214, pump 216, and/or reservoir 322, as described in more detail herein.

In the illustrated embodiment, the holding member 214, as shown in FIGS. 12, 13, 14, 15, and 16 includes a loading member 260, a clamping member 262 releasably attached to the loading member 260, a plurality of gaskets 350, a first spacer 352, a second spacer 354, a first face plate 356, a second face plate 358, a first reinforcing bracket 360, a second reinforcing bracket 362, and defines a first holding member chamber 264, a second holding member chamber 266, a plurality of passageways 268, 270, 272 in communication with the first holding member chamber 264 and second holding member chamber 266, a first input port 274, a second input port 276, a first drain 278, a second drain 280, a first vent 282, and a second vent 284.

The loading member 260 has a main body 286 that defines a first portion of the first holding member chamber 264, a first portion 288 of each passageway of the plurality of passageways 268, 270, 272 and a first guide member 290. The clamping member 262 comprises a first member 263, a second member 265, and a third member 267. Each of the first member 263, the second member 265, and the third member 267 has a main body 294 that defines a portion of the second holding member chamber 266, a second portion 296 of a passageway of the plurality of passageways 268, 270, 272, a second guide member 298, and a sealing member 300. The first portion 288 of each passageway of the plurality of passageways 268, 270, 272 and the second portion 296 of each passageway of the plurality of passageways 268, 270, 272 cooperatively define each passageway of the plurality of passageways 268, 270, 272 of the holding member 214. A sealing member of the plurality of sealing members 300 surrounds each portion of the passageway of the plurality of passageways 268, 270, 272 defined by the clamping member 262 and provides a mechanism to seal the tissue 218 between the loading member 260 and the clamping member 262 (e.g., prevent leakage around the sealing member 300) and maintain the position of the tissue 218 during use.

In the illustrated embodiment, the first guide member 290 comprises a plurality of guide pins 291 and a plurality of guide holes 293 and the second guide member 298 comprises a plurality of guide holes 299 and a plurality of guide pins 301. A guide pin of the plurality of guide pins 291 is disposed within a guide hole of the plurality of guide holes 299 and a guide pin of the plurality of guide pins 301 is disposed within a guide hole of the plurality of guide holes 293 when the clamping member 262 is releasably attached to the loading member 260. Each guide hole of the plurality of guide holes 293 is sized and configured to receive a guide pin of the plurality of guide pins 301 and each guide hole of the plurality of guide holes 299 is sized and configured to receive a guide pin of the plurality of guide pins 291.

The first spacer 352 is releasably attached to the loading member 260 and has a main body 364 that defines a passageway 366, a second portion of the first holding member chamber 264, the first input port 274, the first drain 278, and the first vent 282. The second spacer 354 is releasably attached to the loading member 260 and has a main body 368 that defines a passageway 370, a second portion of the second holding member chamber 266, the second input port 276, the second drain 280, and the second vent 284. A first gasket 372 of the plurality of gaskets 350 is disposed between the loading member 260 and the first spacer 352 and a second gasket 373 of the plurality of gaskets 350 is disposed between the loading member 260 and the second spacer 354.

The first face plate 356 is releasably attached to the first spacer 352 and has a main body 376 that defines a wall 378. The second face plate 358 is releasably attached to the second spacer 354 and has a main body 380 that defines a wall 382. Each of the first face plate 356 and the second face plate 358 is formed of a transparent material to allow for visualization of the tissue during processing. However, alternative embodiments can include a face plate that is formed of an opaque material. A third gasket 392 of the plurality of gaskets 350 is disposed between the first spacer 352 and the first face plate 356 and a fourth gasket 394 of the plurality of gaskets 350 is disposed between the second spacer 354 and the second face plate 358. The loading member 260, the first spacer 352, and the first face plate 356 cooperatively define the first holding member chamber 264. The clamping member 262, the second spacer 354, and the second face plate 358 cooperatively define the second holding member chamber 266. The first reinforcing bracket 360 is releasably attached to the first face plate 356 and has a main body 384 that defines a passageway 386. The first reinforcing bracket 360 provides a mechanism for distributing the load on the first face plate 356 to prevent leaks (e.g., leaks through the gasket 392). The second reinforcing bracket 362 is releasably attached to the second face plate 358 and has a main body 388 that defines a passageway 390. The second reinforcing bracket 362 provides a mechanism for distributing the load on the second face plate 358 to prevent leaks (e.g., leaks through the gasket 394).

A loading member, a clamping member, a plurality of gaskets, a first spacer, a second spacer, a first face plate, a second face plate, a first reinforcing bracket, and a second reinforcing bracket can be releasably attached to one another using any suitable technique or method of attachment. Selection of a suitable technique or method of attachment between one or more components of a holding member can be based on various considerations, including the material that forms a component. Examples of techniques and methods of attachment considered suitable include using threaded connections, snap fit attachments, using one or more connectors, one or more mating slots and projections, one or more sealed unions, tapered attachments, clamps, pneumatic clamps, adhesives, and any other technique or method of attachment considered suitable for a particular embodiment. In the illustrated embodiment, the loading member 260, the plurality of gaskets 350, the first spacer 352, the second spacer 354, the first face plate 356, the second face plate 358, the first reinforcing bracket 360, and the second reinforcing bracket 362 are attached to one another using threaded screws. Alternatively, one or more of a loading member, a clamping member, a plurality of gaskets, a first spacer, a second spacer, a first face plate, a second face plate, a first reinforcing bracket, and/or a second reinforcing bracket can be permanently fixed to one another.

In the illustrated embodiment, the first recess 228 defined by the first tank 212 is in fluid communication with the first holding member chamber 264 such that the high-pressure portion 242 is in fluid communication with the first holding member chamber 264 and the first recess 336 defined by the second tank 320 is in fluid communication with the second holding member chamber 266 such that the low-pressure portion 244 is in fluid communication with the second holding member chamber 266. In the illustrated embodiment, the first recess 228 defined by the first tank 212 is in fluid communication with the first holding member chamber 264 using a first elongate tubular member 302 and the first recess 336 defined by the second tank 320 is in fluid communication with to the second holding member chamber 266 using a second elongate tubular member 304. The first elongate tubular member 302 has a first end in fluid communication with the first passageway 234 defined by the first tank 212 and a second end in fluid communication with the first input port 274 of the holding member 214. The second elongate tubular member 304 has a first end in fluid communication with the first passageway 340 defined by the second tank 320 and a second end in fluid communication with the second input port 276 of the holding member 214.

When a fluid is disposed within the recesses 228, 230, 336, 338 defined by the tanks 212, 320 the pressure differential between the fluid within the first holding member chamber 264 and the second holding member chamber 266 can be controlled by manipulating the relative height between the first tank 212 and the second tank 320. This can be accomplished by calculating a desired pressure differential and configuring the relative heights of the first and second tanks 212, 320. Alternatively, if the type of tissue disposed between a loading member and a clamping member of a differential pressure material processing system has a permeability that degrades over time, the differential pressure material processing systems described herein provide a mechanism for adjusting the differential pressure applied to the tissue (e.g., such that a constant, substantially constant, or varied, differential pressure is applied to the tissue during processing).

The reservoir 322 has a main body 396 that defines a recess 398, a first input port 400, a second input port 402, and an outlet port 404. The first input port 400 is in fluid communication with the second recess 230 defined by the first tank 212 such that the tank reservoir 246 is in fluid communication with the recess 398 defined by the reservoir 346. The second input port 402 is in fluid communication with the second recess 338 defined by the second tank 320 such that the tank reservoir 346 is in fluid communication with the recess 398 defined by the reservoir 346. The output port 404 is connected to the pump 216 such that the recess 398 defined by the reservoir 246 is in fluid communication with the pump 216.

In the illustrated embodiment, the pump 216 includes an outlet port 306, an inlet port 308, and has an on state and an off state. The outlet port 306 is in fluid communication with the first recess 228 defined by the first tank 212 and the first recess 336 defined by the second tank 320 such that the high-pressure portion 242 is in fluid communication with the pump 216 and the low-pressure portion 244 is in fluid communication with the pump 216. The inlet port 308 is in fluid communication with the reservoir 346.

In the illustrated embodiment, the outlet port 306 is in fluid communication with the first recess 228 defined by the first tank 212 using a manifold 311 and a third elongate tubular member 310. The manifold 311 has a first end in fluid communication with the outlet port 306 of the pump 316. The third elongate tubular member 310 has a first end in fluid communication with a second end of the manifold 311 and a second end in fluid communication with the second passageway 236 defined by the main body 222 of the first tank 212. The outlet port 306 is in fluid communication with the first recess 336 defined by the second tank 320 using the manifold 311 and a fourth elongate tubular member 314 that has a first end in fluid communication with a third end of the manifold 311 and a second end in fluid communication with the second passageway 342 defined by the main body 332 of the second tank 320. The recess 398 defined by the reservoir 322 is in fluid communication with the second recess 230 defined by the first tank 212 using a fifth elongate tubular member 316 that has a first end in fluid communication with the first input port 400 and a second end in fluid communication with the third passageway 238 defined by the main body 222 of the first tank 212. The recess 398 defined by the reservoir 322 is in fluid communication with the second recess 338 defined by the second tank 320 using a sixth elongate tubular member 318 that has a first end in fluid communication with the second input port 402 and a second end in fluid communication with the third passageway 344 defined by the main body 332 of the second tank 320. The recess 398 defined by the reservoir 322 is in fluid communication with the inlet port 308 of the pump 216 using a ninth elongate tubular member 410 that has a first end in fluid communication with the outlet port 404 and a second end in fluid communication with the inlet port 308 of the pump 216.

While the outlet port 306 has been illustrated as being in fluid communication with the first recess 228 defined by the first tank 212 and the first recess 336 defined by the second tank 320 such that the high-pressure portion 242 is in fluid communication with the pump 216 and the low-pressure portion 244 is in fluid communication with the pump 216, an alternative embodiment can include a pump that is only in fluid communication with a first recess defined by a first tank that is positioned higher than a second tank along a vertical axis. In other alternative embodiments, a pump and/or a reservoir can be omitted from a differential pressure material processing system in embodiments in which the tissue being processed in impermeable, or substantially impermeable.

Figure 10:
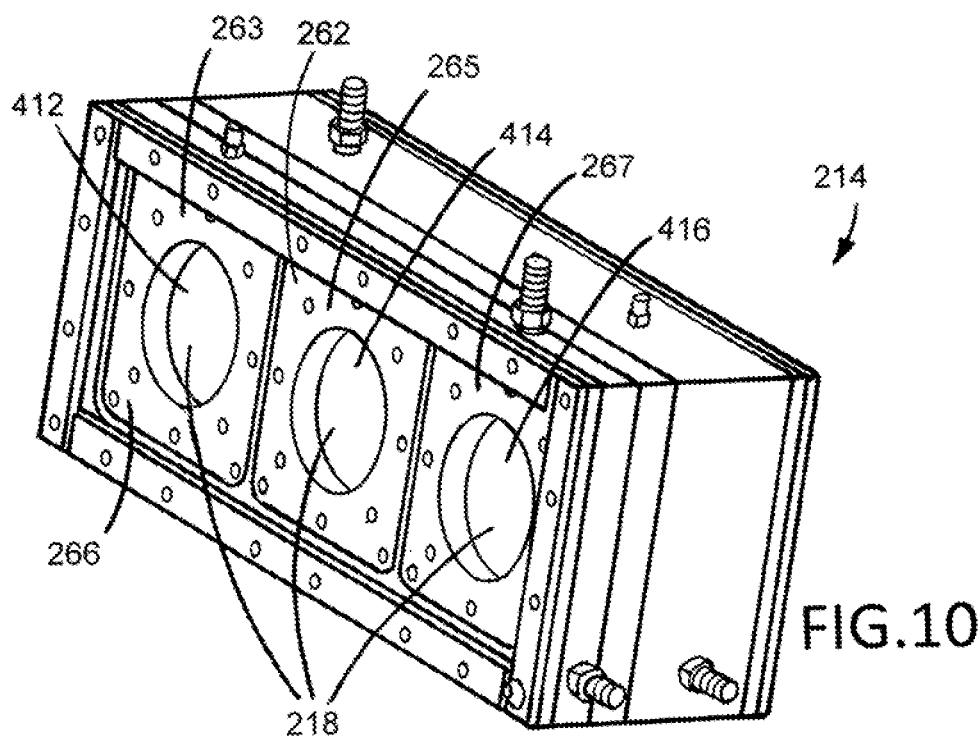
FIG. 10 is a perspective view of the holding member of the system illustrated in FIG. 6.
Figure 11:
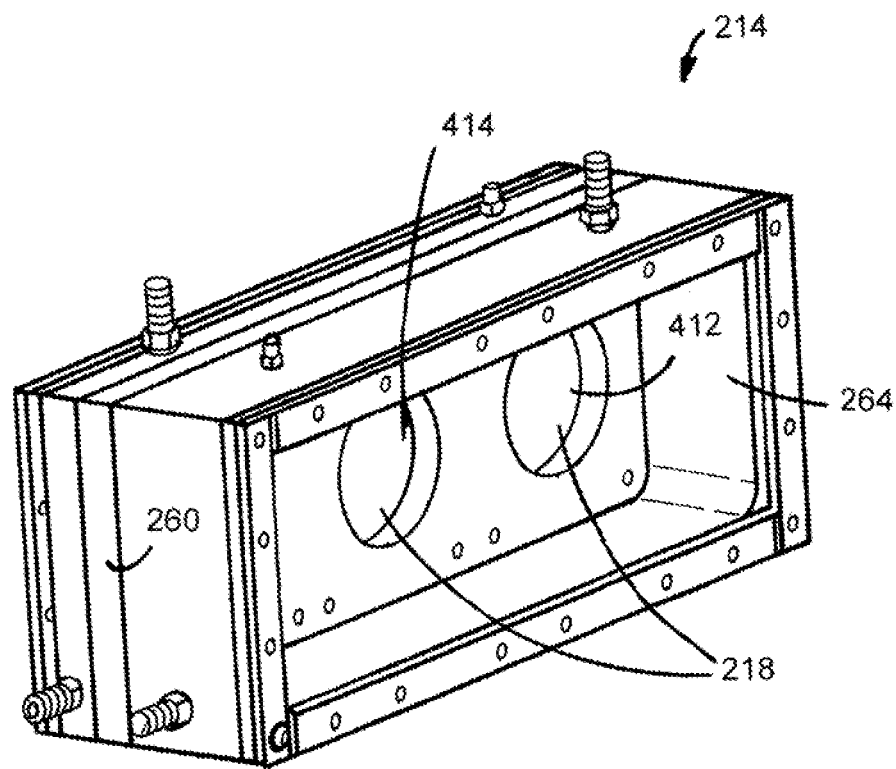
FIG. 11 is another perspective view of the holding member illustrated in FIG. 10.
Figure 12:
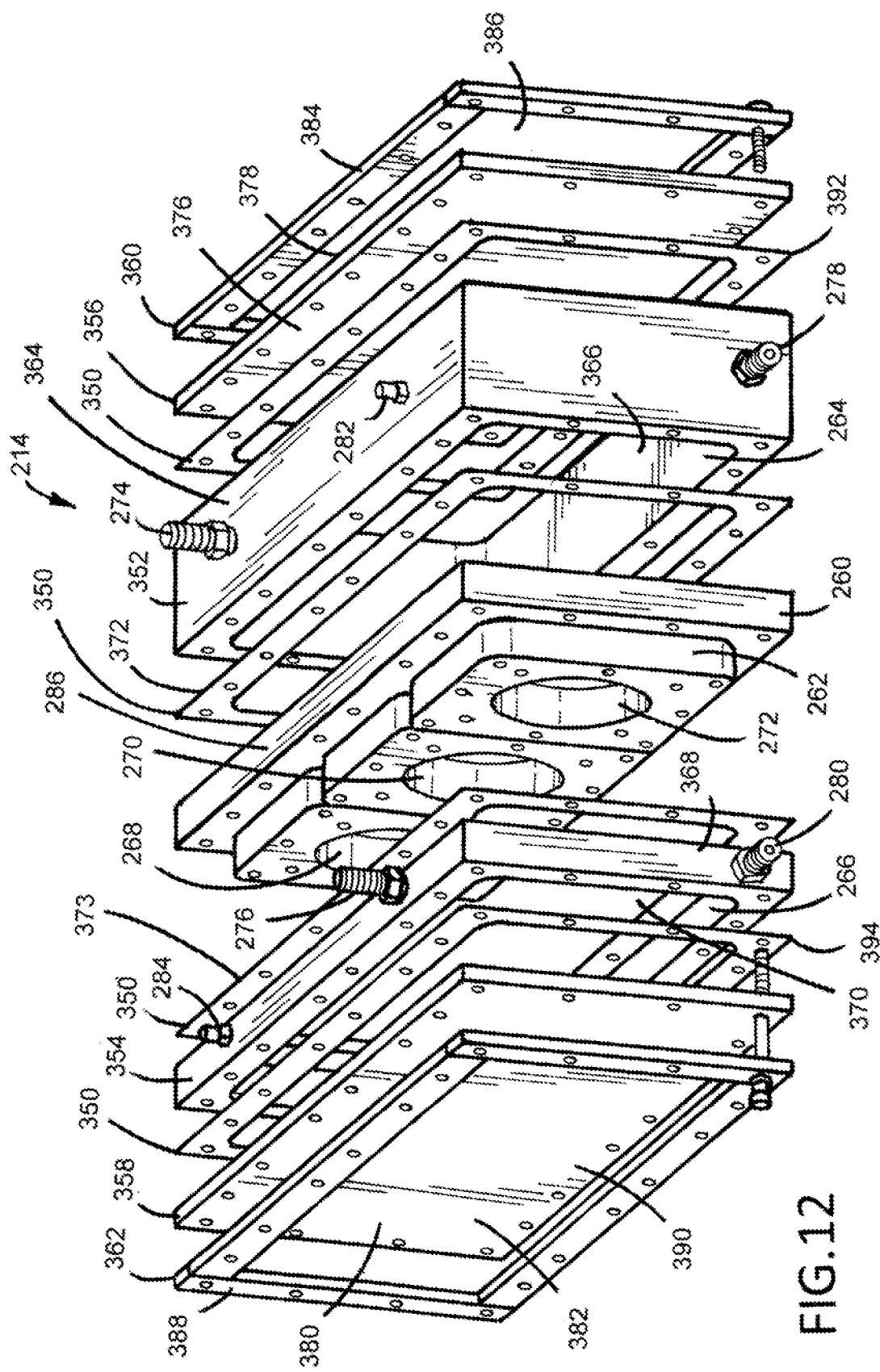
FIG. 12 is an exploded perspective view of the holding member illustrated in FIG. 10.
Figure 13:
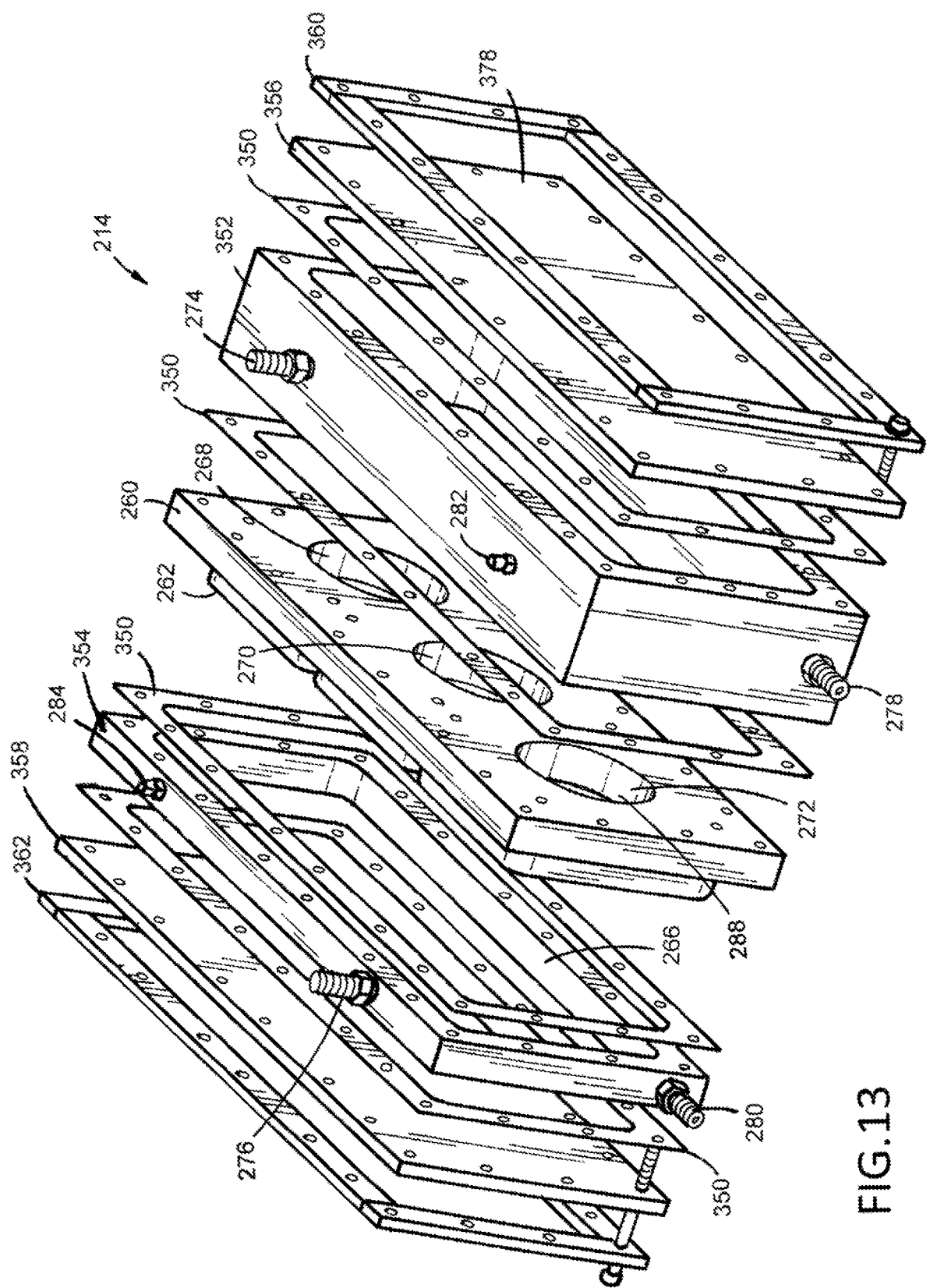
FIG. 13 is another exploded perspective view of the holding member illustrated in FIG. 10.

In the illustrated embodiment, as shown in FIGS. 10 and 11, a first sheet of tissue 412 of the plurality of sheets of tissue 218, a second sheet of tissue 414 of the plurality of sheets of tissue 218, and a third sheet of tissue 416 of the plurality of sheets of tissue 218 are disposed within the holding member 214 between the loading member 260 and the clamping member 262. The first sheet of tissue 412 is disposed between the first member 263 of the clamping member 262 and the loading member 260 such that the first passageway 268 is obstructed by a portion of the first sheet of tissue 412 that spans the entire cross section of the passageway 268 defined by the loading member 260 and the first member 263. The second sheet of tissue 414 is disposed between the second member 265 of the clamping member 262 and the loading member 260 such that the second passageway 270 is obstructed by a portion of the second sheet of tissue 414 that spans the entire cross section of the passageway 270 defined by the loading member 260 and the second member 265. The third sheet of tissue 416 is disposed between the third member 267 of the clamping member 262 and the loading member 260 such that the third passageway 272 is obstructed by a portion of the third sheet of tissue 416 that spans the entire cross section of the passageway 272 defined by the loading member 260 and the third member 267. The sheets of tissue 412, 414, 416 can be positioned in these configurations at any suitable time. For example, prior to, during, and/or subsequent to the application of differential pressure (e.g., when the pump 216 is in the on state and the off state). Each sheet of tissue of the plurality of sheets of tissue 218 spans a passageway defined by the holding member 260 such that the entire sealing member 300 surrounding the passageway defined by the clamping member 262 fully engages the tissue when the loading member 260 and the clamping member 262 are releasable attached to one another.

To complete processing of the tissue 218, such as fixation, a fluid is pumped into the first tank 212 and the second tank 320. The fluid is pumped into the first tank 212 until the level of fluid reaches the top of the first non-permeable wall 224 and travels into the second recess 230, the fluid travels from the first recess 228 into the first holding member chamber 264, and is applied to the plurality of sheets of tissue 218. The fluid is pumped into the second tank 320 until the level of fluid reaches the top of the first non-permeable wall 334 and travels into the second recess 338, the fluid travels from the first recess 336 into the second holding member chamber 266, and is applied to the plurality of sheets of tissue 218. The position of the tanks 212, 320 (e.g., recesses 228, 230, 336, 338 defined by the tanks 212, 320) relative to the holding member 214 maintain a constant, or substantially constant, head height and pressure differential across the plurality of sheets of tissue 218 when the fluid is constantly pumped into the tanks 212, 320 resulting in the plurality of sheets of tissue 218 being processed under differential pressure. This is considered advantageous at least because it provides a mechanism for accounting for any tissue permeability, which would allow fluid to travel through the tissue from a first holding member chamber to a second holding member chamber. In the illustrated embodiment, the holding member 214 is not directionally dependent since it omits the inclusion of a support member, such as support member 92. Therefore, in an alternative embodiment, the high-pressure portion of a tank can be in fluid communication with a second holding member chamber and a low-pressure portion of a tank can be in fluid communication with a first holding member chamber.

While a single holding member 214 has been illustrated as being included in the differential pressure material processing system 210, any suitable number of holding members can be included in a differential pressure material processing system and attached to the various components as described herein and selection of a suitable number of holding members to include in a differential pressure material processing system can be based on various considerations, including the number of sheets of tissue intended to be processed using the differential pressure material processing system. Examples of numbers of holding members considered suitable to include in a differential pressure material processing system include one, at least one, two, a plurality, three, four, five, more than five, and any other number considered suitable for a particular embodiment. For example, a plurality of holding members can be used concurrently in a differential pressure material processing system to provide processing of a plurality of sheets of tissue. In embodiments in which a plurality of holding members are being used concurrently, each holding member can optionally be connected to a valved manifold such that differential pressure can be applied to individual holding members as desired.

Figure 18:
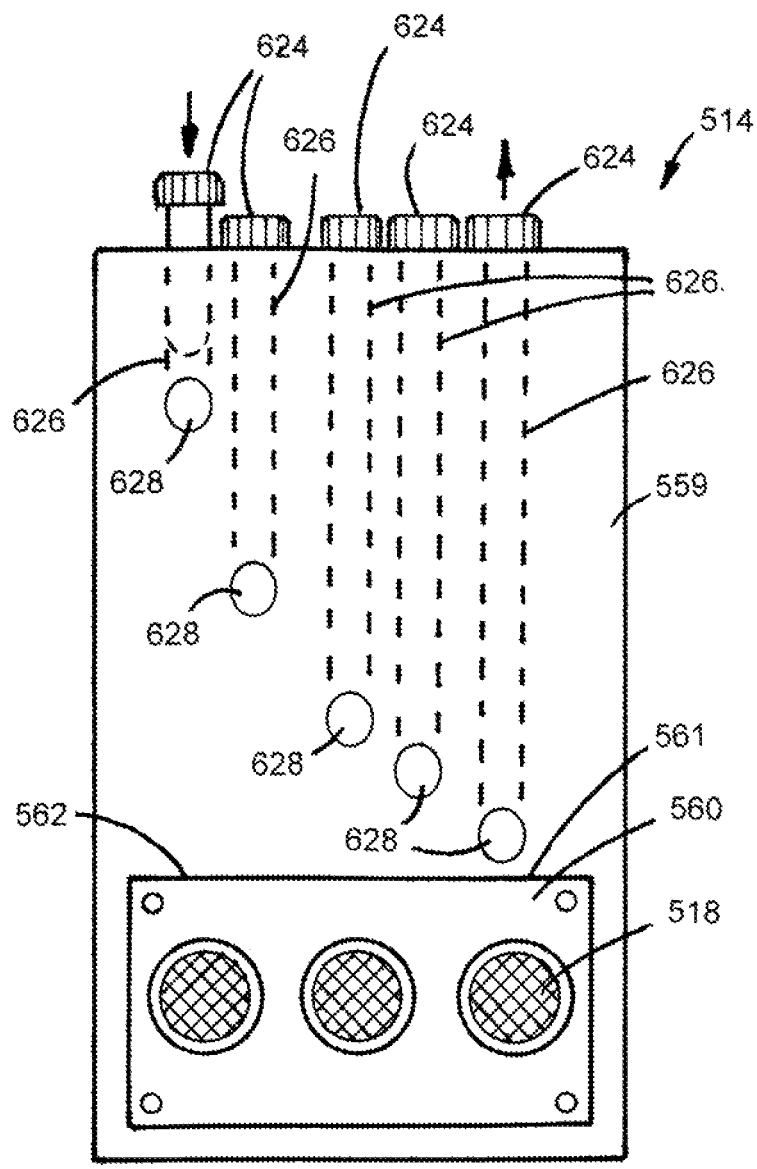
FIG. 18 is a front view of the holding member of the system illustrated in FIG. 17.
Figure 19:
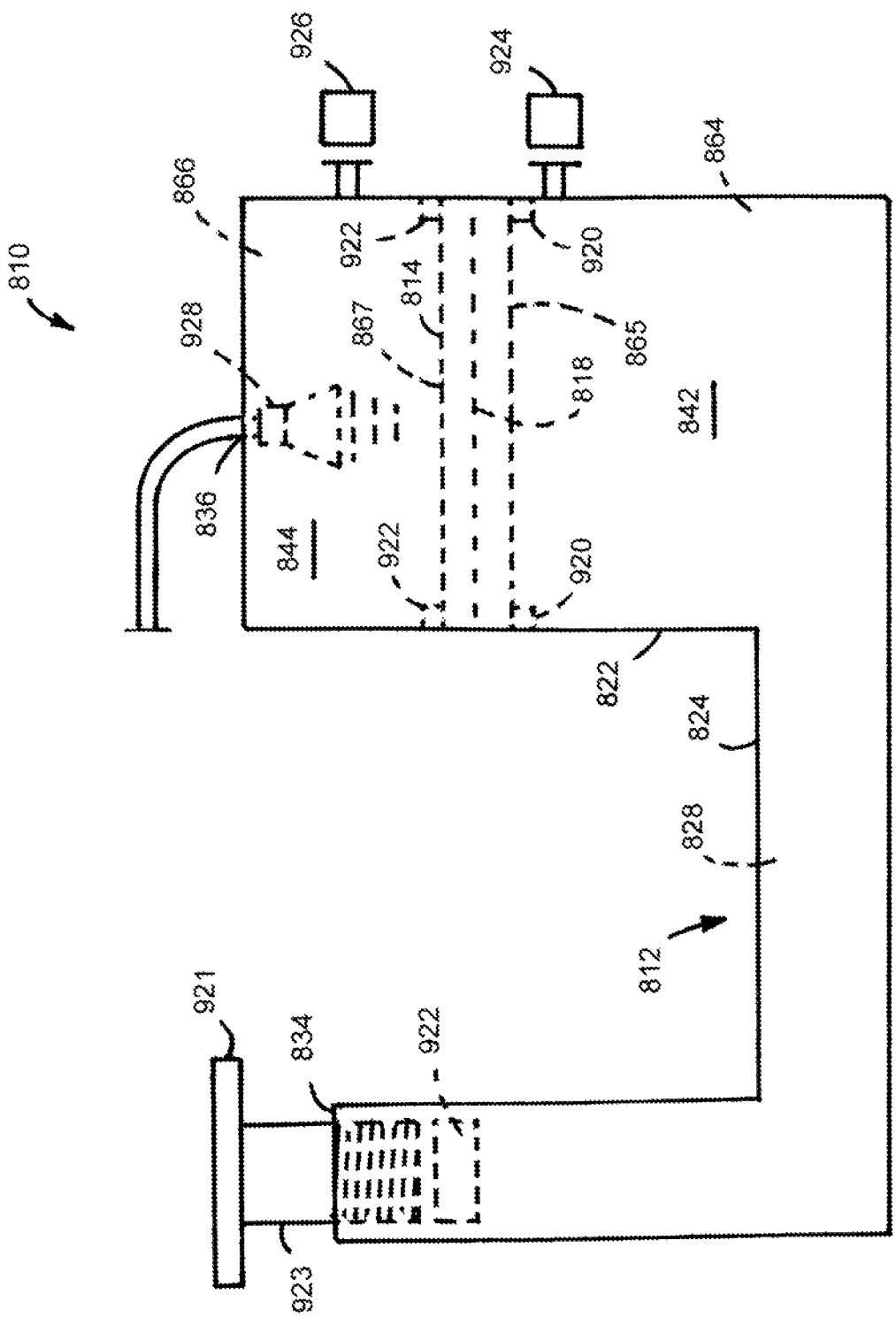
FIG. 19 is a perspective view of another example differential pressure material processing system.
Figure 20:
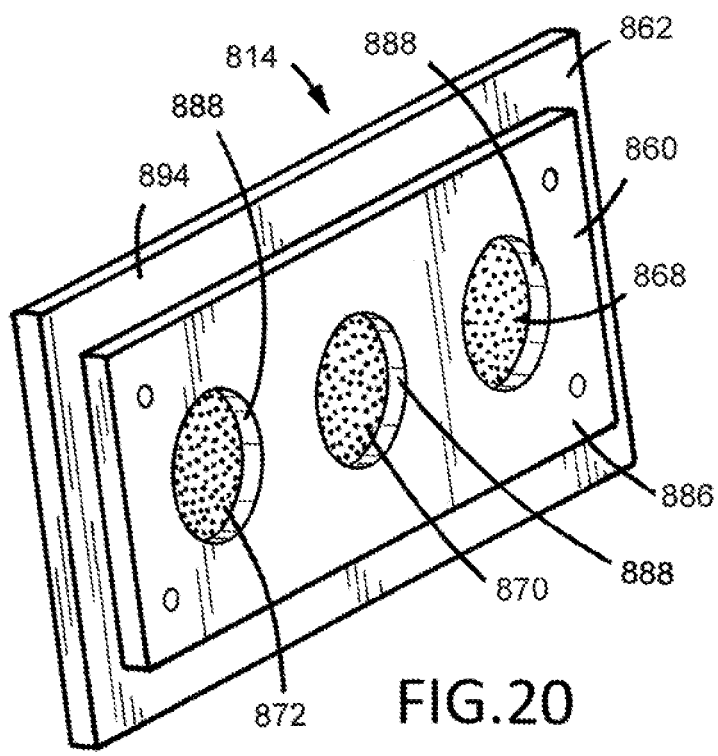
FIG. 20 is a perspective view of the holding member of the system illustrated in FIG. 19.
Figure 21:
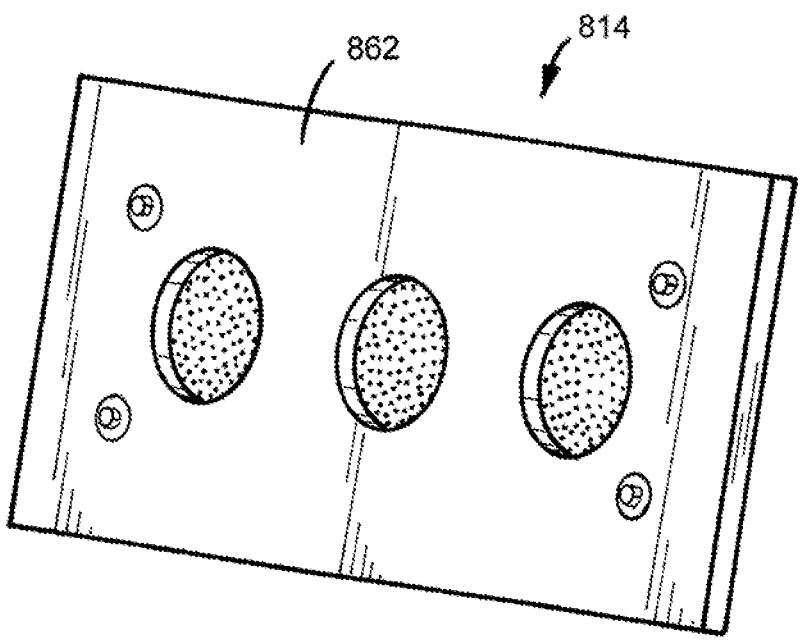
FIG. 21 is another perspective view of the holding member illustrated in FIG. 20.
Figure 22:
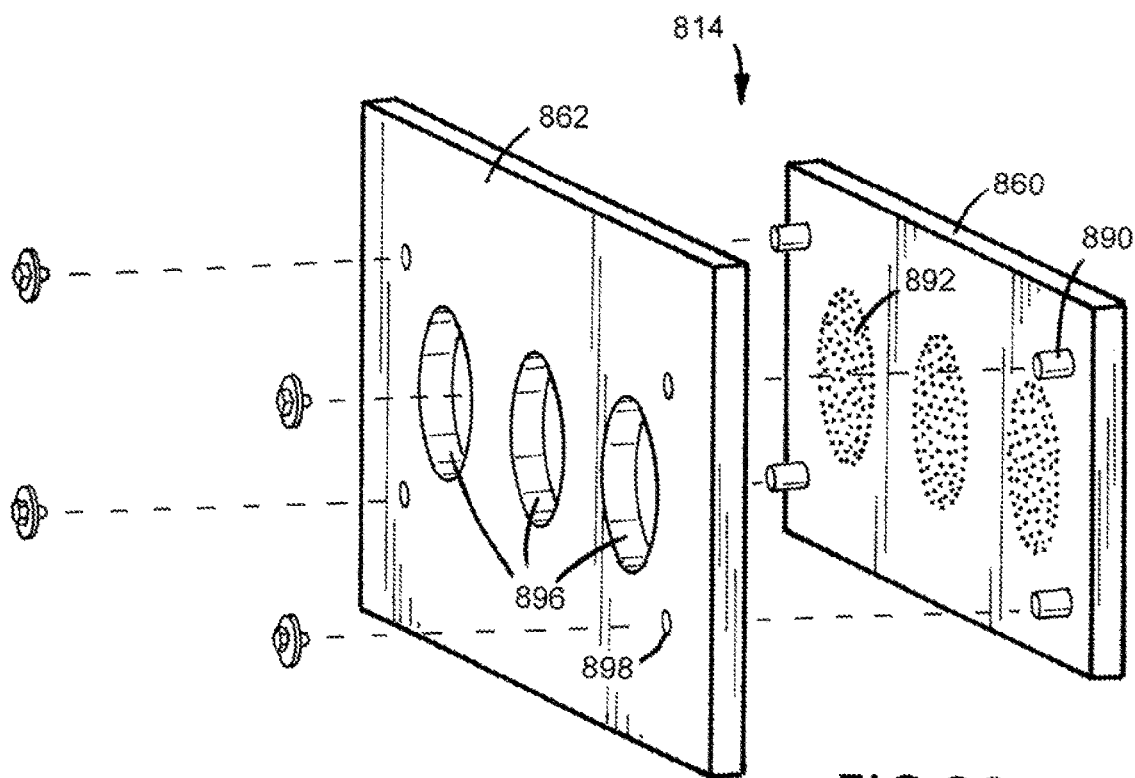
FIG. 22 is an exploded perspective view of the holding member illustrated in FIG. 20.
Figure 23:
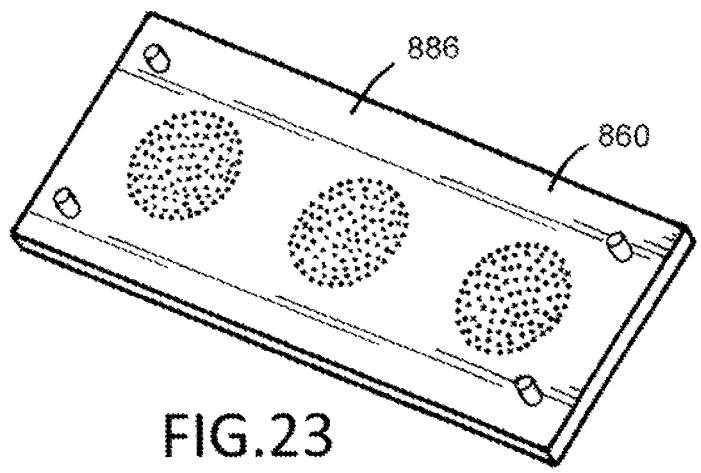
FIG. 23 is a perspective view of the loading member of the system illustrated in FIG. 19.
Figure 24:
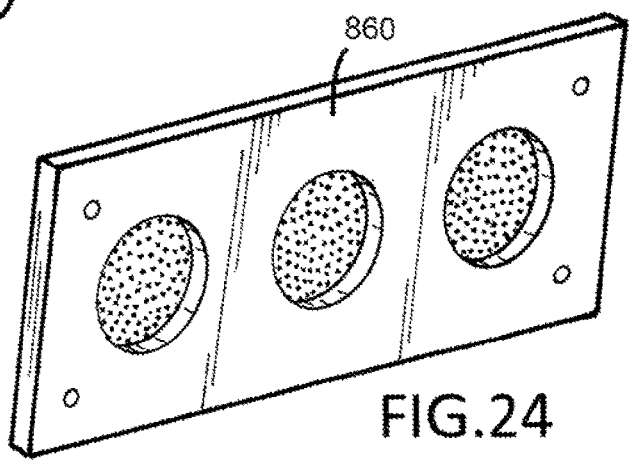
FIG. 24 is another perspective view of the loading member illustrated in FIG. 23.
Figure 25:
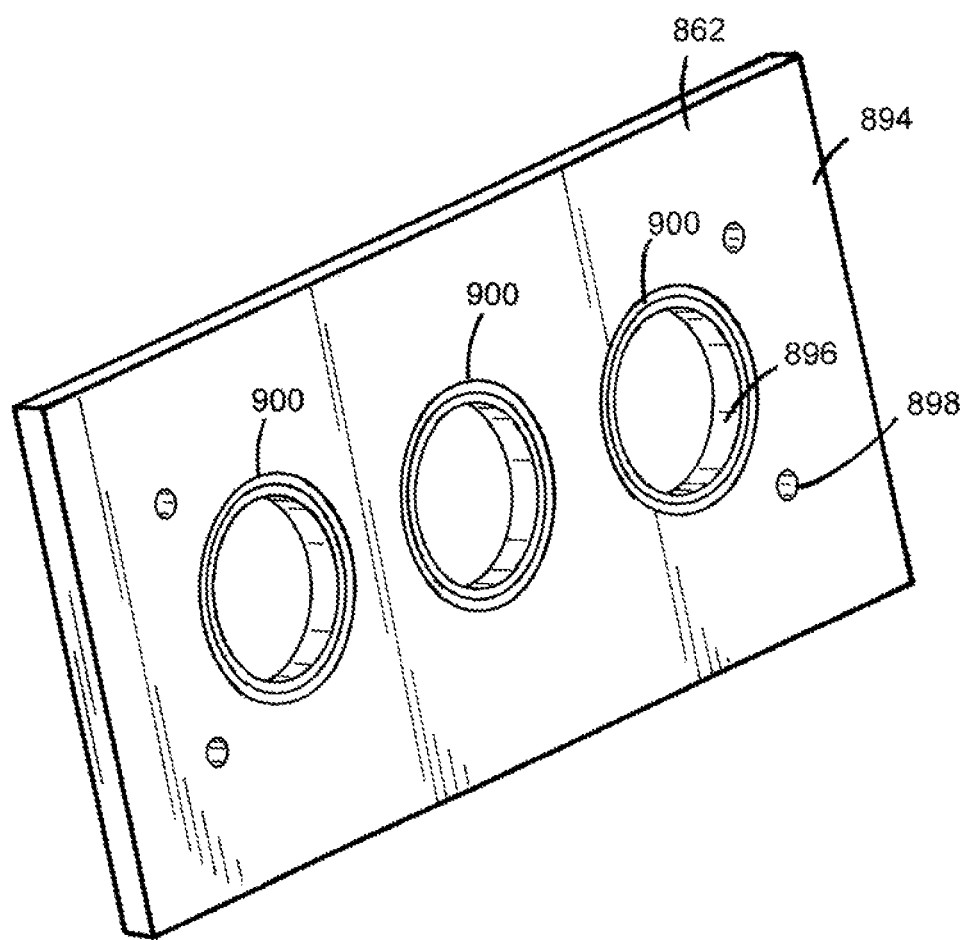
FIG. 25 is a perspective view of the clamping member of the system illustrated in FIG. 19.

FIGS. 17 and 18 illustrate another example differential pressure material processing system 510. The differential pressure material processing system 510 is similar to the differential pressure material processing system 10 illustrated in FIGS. 1, 2, 3, 4, and 5 and described above, except as detailed below. The differential pressure material processing system 510 includes a tank 512, a holding member 514 disposed within the tank 512, a pump 516, a sheet of tissue 518 disposed within the holding member 514, and a reservoir 622.

In the illustrated embodiment, the tank 512 has a main body 522 that defines a wall 524, a recess 528, a first passageway 534 in communication with the recess 528, a second passageway 536 in communication with the recess 528, a first track 620, and a second track 622. Each of the first passageway 534 and the second passageway 536 extends through the main body 522 and provides access between the recess 528 and an environment exterior to the recess 528. Each of the first track 620 and the second track 622 is a u-shaped member defined within the recess 528. The first track 620 is separated from the second track 622 a distance that is equal to, or slightly larger than, the thickness of the holding member 514. Optionally, one or more gaskets can be included along one, or both the tracks to provide additional sealing between the track and a holding member during use. Alternatively, a first track and a second track can be separate members that are attached to a tank. An attachment member 541 is attached to the tank 512 within each of the passageways 534, 536, to provide a mechanism to attach the tank 512 to another component, such as the pump 516 and/or reservoir 622, as described in more detail herein.

In the illustrated embodiment, the holding member 514 is releasably disposed within the tank 512 and includes a loading member 560, a clamping member 562 releasably attached to the loading member 560, and a cartridge 559. The cartridge 559 defines a passageway 561, a plurality of blind passageways 626, a plurality of through passageways 628, and includes a plurality of pistons 624. Each blind passageway of the plurality of blind passageways 626 is in communication with a through passageway of the plurality of through passageways 628. Each through passageway of the plurality of through passageways 628 has an open configuration and a closed configuration. A piston of the plurality of pistons 624 is disposed within a blind passageway 626 and is moveable between a first position and a second position such that when the piston is in the first position the associated through passageway is in the open configuration and when the piston is in the second position the associated through passageway is in the closed configuration. The position of each through passageway of the plurality of through passageways 628 varies along the height of the holding member 514 such that the differential pressure between the first holding member chamber 564 and the second holding member chamber 566, as described in more detail herein, can be manipulated during use. In the open configuration, each passageway of the plurality of through passageways 628 is in fluid communication with the first holding member chamber 564 and the second holding member chamber 566.

A piston included in a holding member 514 can be moveable between a first position and a second position using any suitable technique or method and selection of a suitable technique or method can be based on various consideration, including the material forming a holding member. Examples of techniques and methods considered suitable to move a piston between first and second configurations include threaded connections between a cartridge and a piston such that the piston can be moved manually or can be automated, the inclusion of linear drive pistons that can be moved manually or can be automated, and any other technique or method considered suitable for a particular embodiment.

The passageway 561 defined by the cartridge 559 is sized and configured to receive a loading member 560 and a clamping member 562. While an example loading member 560 and clamping member 562 have been illustrated as being disposed within passageway 561, any suitable loading member and/or clamping member can be included in a holding member, such as those described herein. In the illustrated embodiment, the loading member 560 and the clamping member 562 are similar to the loading member 260 and clamping member 262 illustrated and described with respect to FIGS. 6, 7, 8, 9, 10, 11, 12, 13, 14, 15, and 16, except that they omit the inclusion of a first input port, a second input port, a first drain, a second drain, a first vent, a second vent, a first face plate, a second face plate, a first reinforcing member, a second reinforcing member, a third gasket, and a fourth gasket. Alternatively, a holding member, such as the holding member 814 illustrated and described with respect to FIGS. 19, 20, 21, 22, 23, 24, and 25 could be utilized with differential pressure material processing system 510.

When the holding member 514 is disposed within the recess 528 defined by the tank 512 between the first track 620 and the second track 622, a first holding member chamber 564 is defined on a first side 565 of the holding member 514 and a second holding member chamber 566 is defined on a second side 567 of the holding member 514. The first holding member chamber 564 defines a first portion of the tank 512. When fluid is disposed within the first holding member chamber 564 to a level at which the fluid has a height greater than the height of a through passageway of the plurality of through passageways 628 that is in the open configuration and the fluid flows into the second holding member chamber 566 the fluid has a first pressure creating a high-pressure portion 542 of the tank 512. The second holding member chamber 566 defines a second portion of the tank 512. When fluid is disposed within the second holding member chamber 566 to a level at which the fluid has a height greater than the height of the second passageway 536 and the fluid flows into the reservoir 622 the fluid has a second pressure that is less than the first pressure creating a low-pressure portion 544 of the tank 512.

When a fluid is disposed within the recess 528 defined by the tank 512, the pressure differential of the fluid within the first holding member chamber 564 and the second holding member chamber 566 can be controlled by manipulating the through passageway of the plurality of through passageways 628 that is in the open configuration and/or the location of the second passageway 536 along the height of the tank 512. For example, the pressure on the high-pressure portion 542 can be varied by manipulating the through passageway of the plurality of through passageways 628 that is in the open configuration and/or the pressure on the low-pressure portion 544 can be varied by varying the location of the second passageway 536 of the tank 512 along the height of the tank 512. In an alternative embodiment, multiple passageways could be defined by a tank and in fluid communication with a low-pressure portion of a tank to provide additional mechanisms for controlling the pressure of a second holding member chamber, multiple through passageways could be positioned in an open configuration to manipulate the pressure of a first holding member chamber, and/or the height of a cartridge can be adjusted to manipulate the pressure between a first holding member chamber and a second holding member chamber.

In the illustrated embodiment, the high-pressure portion 542 is in fluid communication with the pump 516 using a first elongate tubular member 602 that has a first end in fluid communication with the first passageway 534 and a second end in fluid communication with the outlet port 606 of the pump 516. The low-pressure portion 544 is in fluid communication with the recess 698 defined by the reservoir 622 using a second elongate tubular member 604 that has a first end in fluid communication with the second passageway 536 and a second end in fluid communication with the input port 700 of the reservoir 622. The recess 698 defined by the reservoir 622 is in fluid communication with the pump 516 using a third elongate tubular member 610 that has a first end in fluid communication with the outlet port 704 of the reservoir 622 and a second end in fluid communication with the input port 608 of the pump 516. In alternative embodiments, a pump could be directly connected to a second portion of a tank (e.g., low-pressure portion of the tank) such that a reservoir can be omitted from a system. In these alternative embodiments, the pump can be configured such that its pumping rate is balanced with the rate of fluid leakage across the tissue and/or through the one or more through passageways.

Alternative to the inclusion of a plurality of blind passageways, a plurality of through passageways, and a plurality of pistons, a holding member can include other features, devices, or components to accomplish manipulation of the pressure differential between a first holding member chamber and a second holding member chamber. Selection of suitable features, devices, and/or components to include on a holding member to assist with manipulation of the pressure differential between a first holding member chamber and a second holding member chamber can be based on various considerations, including the structural arrangement of a holding member and/or tank. For example, alternative to the inclusion of a plurality of blind passageways, a plurality of through passageways, and a plurality of pistons, or in addition to these features and components, a holding member can include a cartridge that comprises a plurality of plates that can be stacked between a first track and a second track to assist with the manipulation of the pressure differential.

FIGS. 19, 20, 21, 22, 23, 24, and 25 illustrate another example differential pressure material processing system 810. The differential pressure material processing system 810 is similar to the differential pressure material processing system 10 illustrated in FIGS. 1, 2, 3, 4, and 5 and described above, except as detailed below. The differential pressure material processing system 810 includes a tank 812, a holding member 814 disposed within the tank 812, a sheet of tissue 818 disposed within the holding member 814, an actuator 921, a plunger 922, a first pressure transducer 924, a second pressure transducer 926, and an ultrasound transducer 928.

In the illustrated embodiment, the tank 812 has a main body 822 that defines a wall 824, a recess 828, a first opening 834 in communication with the recess 828, a second opening 836 in communication with the recess 828, a first track 920, and a second track 922. Each of the first opening 834 and the second opening 836 extends through the main body 822 and provides access between the recess 828 and an environment exterior to the recess 828. Depending on the pressure desired on a low-pressure portion of the tank 812, a second opening can be configured such that it contacts any device disposed through the opening (e.g., the opening is sealed, or substantially sealed, to create a closed system), or such that the opening does not contact a device disposed through the opening and the system is not closed. Each of the first track 920 and the second track 922 is a rectangular member that defines a passageway. Each of the first track 920 and the second track 922 is disposed within the recess 828 and is similar to the tracks 620, 622 described above with respect to FIGS. 17 and 18. The first track 920 is separated from the second track 922 a distance that is equal to, or slightly larger than, the thickness of the holding member 814. In the illustrated embodiment, the first track 920 is fixed to the tank 812 and the second track 922 is releasably attached to the tank 812 such that the holding member 814 can be positioned within the tank 812, as described in more detail herein. The second track 922 can be releasably attached using any suitable technique or method of attachment, such as those described herein.

In the illustrated embodiment, the holding member 814 includes a loading member 860, a clamping member 862 releasably attached to the loading member 860, and defines a plurality of passageways 868, 870, 872. In the illustrated embodiment, the loading member 860 has a main body 886 that defines a first portion 888 of each passageway of the plurality of passageways 868, 870, 872, a first guide member 890, and a support member 892 (e.g., perforated member) spanning each portion of a passageway of the plurality of passageways 868, 870, 872 defined by the loading member 860. In the illustrated embodiment, the clamping member 862 has a main body 894 that defines a second portion 896 of each passageway of the plurality of passageways 868, 870, 872, a second guide member 898, and a plurality of sealing members 900.

When the holding member 814 is disposed within the recess 828 defined by the tank 812 between the first track 920 and the second track 922, a first holding member chamber 864 is defined on a first side 865 of the holding member 814 and a second holding member chamber 866 is defined on a second side 867 of the holding member 814. The first holding member chamber 864 defines a first portion of the tank 812. When fluid is disposed within the first holding member chamber 864 and pressure is applied using the actuator 921, as described in more detail herein, the fluid has a first pressure creating a high-pressure portion 842 of the tank 812. The second holding member chamber 866 defines a second portion of the tank 812. When fluid is disposed within the second holding member chamber 866 within the second holding member chamber 866 above the holding member 814 the fluid has a second pressure that is less than the first pressure creating a low-pressure portion 844 of the tank 812.

The actuator 921 is disposed through the first opening 834 defined by the tank 812 and is moveable within the first opening 834 between a first position and a second position. The plunger 922 is disposed between the actuator 921 and the holding member 814 and is moveable within the high-pressure portion 842 between a first position and a second position. The plunger 922 is in the first position when the actuator 921 is in the first position and the plunger 922 is in the second position when the actuator 921 is in the second position. Any suitable actuator can be included in a differential pressure material processing system and selection of a suitable actuator can be based on various considerations, including the pressures intended to be applied to tissue being processed. Examples of actuators suitable for inclusion in a differential pressure material processing system include linear actuators, rotatable actuators, manually operated actuators, automated actuators, combinations of the actuators described herein, and any other actuator considered suitable for a particular embodiment. In the illustrated embodiment, the actuator 921 comprises a rotatable actuator 923 that is manually operated.

When a fluid is disposed within the recess 828 defined by the tank 812, the pressure of the fluid within the first holding member chamber 864 can be controlled by manipulating the position of the actuator 921 between its first and second positions and the pressure of the fluid within the second holding member chamber 866 can be controlled by manipulating the position of the holding member 812 within the recess 854 defined by the tank 812 and/or the level of fluid disposed above the holding member 814.

The first pressure transducer 924 is in communication with the high-pressure portion 842 and the second pressure transducer 926 is in communication with the low-pressure portion 844. The inclusion of first and second pressure transducers 924, 926 provides a mechanism for providing real-time data relating to the differential pressure being applied to tissue 818 disposed within the holding member 814 and allows for a user to adjust the pressure being applied to the tissue 818 accordingly. The ultrasound transducer 928 is disposed within the recess 828 and provides a mechanism for characterizing the tissue 818 in real time and monitoring the properties of the tissue 818 during processing. In the illustrated embodiment, the ultrasound transducer 928 is disposed within the second holding member chamber 866. Any differential pressure material processing system described herein can include one or more pressure transducers in communication with a high-pressure portion of a tank, a low-pressure portion of a tank, a first holding member chamber, and/or a second holding member chamber. In addition, any differential pressure material processing system described herein can include one or more ultrasound transducers in communication with a high-pressure portion of a tank, a low-pressure portion of a tank, a first holding member chamber, and/or a second holding member chamber. Any suitable pressure transducer and/or ultrasound transducer can be included in a differential pressure material processing system and selection of a suitable pressure transducer and ultrasound transducer can be based on various considerations, including the amount of differential pressure being applied to a tissue and/or the type of tissue being processed. Examples of suitable pressure transducers considered suitable to include in a differential pressure material processing system include those that are within the sensitivity range of the differential pressure being applied to tissue, and any other pressure transducer considered suitable for a particular embodiment. Alternatively, a manometer in communication with a first holding member chamber and a second holding member can be used. Examples of suitable ultrasound transducers considered suitable to include in a differential pressure material processing system include linear arrays, phased arrays, single element transducers with frequency ranges between about 20 kHz and about 100 MHz, a matrix of transducers, high-frequency transducers, multiple-frequency transducers, movable transducers, transducers disposed parallel, and/or perpendicular to, a tissue being processed, combinations of those described herein, and any other transducer considered suitable for a particular embodiment. For example, an array of transducers could be utilized to create a full x-y patterning of tissue characteristics. Alternative to, or in combination with use of an ultrasound transducer, optical measuring devices and/or laser measuring devices could be utilized to characterize tissue being processed.

A tank and a holding member, or portions of a tank and holding member, or any other portion of a differential pressure material processing system, of the embodiments described herein can be formed of any suitable material and using any suitable method of manufacture. Selection of a suitable material and method of manufacture can be based on various considerations, including the intended use of the tank and/or holding member. Examples of materials considered suitable to form a tank and/or holding member of the embodiments described herein include biocompatible materials, materials that can be made biocompatible, metals, such as 316 stainless and 304 stainless, corrosion resistant materials, plastics, polymers, polyethylene, such as high-density polyethylene (HDPE), polypropylene, polycarbonates, silicone, Delrin, transparent materials, opaque materials, and any other material considered suitable for a particular embodiment.

Various methods of treatment are described herein. While the methods described herein are shown and described as a series of acts, it is to be understood and appreciated that the methods are not limited by the order of acts, as some acts may in accordance with these methods, occur in the order shown and/or described, in different orders, and/or concurrently with other acts described herein.

Figure 26:
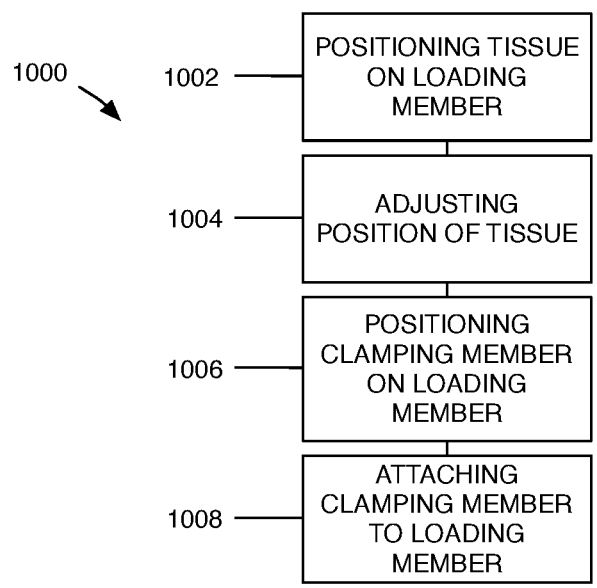
FIG. 26 is a schematic illustration of an example method of loading tissue into a holding member.

FIG. 26 is a schematic illustration of an example method 1000 of loading tissue into a holding member.

A step 1002 comprises positioning a sheet of tissue on a loading member such that a portion of the tissue is separated from the loading member by a fluid layer disposed between the tissue and the loading member. Another step 1004 comprises adjusting the position of the tissue. Another step 1006 comprises positioning a clamping member on the loading member. Another step 1008 comprises releasably attaching the clamping member to the loading member.

Step 1002 can be accomplished using any suitable loading member and selection of a suitable loading member can be based on various considerations, including the material that forms a loading member. Examples of loading members considered suitable to complete a method of loading tissue into a holding member include loading member 60, loading member 260, loading member 560, loading member 860, loading member 1760, and any other loading member considered suitable for a particular embodiment.

Step 1002 can be accomplished such that the tissue is positioned on the loading member in a resting state. The phrase "resting state" means the tissue is in a state in which the only non-naturally occurring forces being applied to the tissue occur from the tissue's contact with the fluid layer and the loading member when the tissue is positioned on the fluid layer and the loading member, occur from the tissue's contact with the fluid layer when the tissue is positioned on the fluid layer, or occur from the tissue's contact with the loading member when the tissue is positioned on the loading member. A resting state may include a state in which a sheet of tissue includes wrinkles and/or folds, a state in which a sheet of tissue is planar (e.g., a planar resting state) in which a surface of the tissue (e.g., top surface, bottom surface) is parallel, or substantially parallel, to a surface of a loading member (e.g., a surface of the loading member on which the tissue is intended to be disposed), a resting state in which a surface of the tissue is similar, or substantially similar, to a surface of a loading member (e.g., a curved surface of the loading member on which the tissue is intended to be disposed), and any other state considered suitable for a particular embodiment. Depending on the material forming a loading member (e.g., low-friction materials, such as Teflon), in alternative embodiments step 1002 can comprise positioning a sheet of tissue on a loading member such that the tissue contacts the loading member.

Step 1002 can be accomplished using any suitable technique or method of positioning tissue on a loading member and selection of a suitable technique or method can be based on various considerations, including the structural arrangement of a loading member. Examples of techniques and methods considered suitable include using the hands of an individual, using automated robotics systems, convention tools, such as hand tools, and any other technique or method considered suitable for a particular embodiment.

Figure 27:
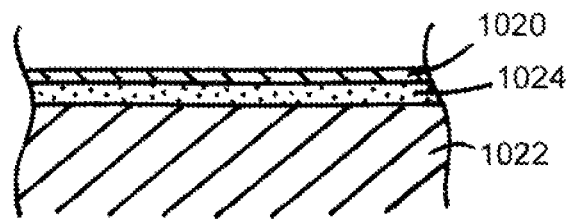
FIG. 27 is a partial sectional view of a sheet of tissue positioned on a loading member.

A fluid layer disposed between tissue and a loading member can include any suitable fluid positioned between the tissue and the loading member using any suitable technique or method. Selection of a suitable fluid and technique or method to position the fluid layer between tissue and a loading member can be based on various considerations, including the type of tissue being positioned within a holding member. Examples of fluids considered suitable to position between tissue and a loading member include lubricious coatings, such as those that are applied to the loading member prior to step 1002, saline, phosphate buffered saline, lactated ringers, fluids described herein, such as fixation solutions, water, neutral oils, and any other fluid considered suitable for a particular embodiment. Examples of suitable techniques and methods of positioning a fluid layer between tissue and a loading member include applying a fluid layer prior to, during, and/or subsequent to, step 1002, activating a pump prior to and/or during step 1002 such that a fluid layer is positioned between tissue and a loading member (e.g., travels through a loading member and/or loading tool and onto a perforated surface), applying fluid to the loading member using an applicator, placing a loading member and/or other component within a fluid bath such that a top surface of the loading member and/or other component is disposed at, near, or below, the level of the fluid within the bath, and any other technique or method considered suitable for a particular embodiment. An optional step that can be completed prior to step 1002 comprises applying a fluid to the loading member to create a fluid layer. FIG. 27 illustrates a sheet of tissue 1020 positioned on a loading member 1022 such that the tissue 1020 is in its resting state and a portion of the tissue 1020 is separated from the loading member 1022 by a fluid layer 1024 disposed between the tissue 1020 and the loading member 1022.

While step 1002 has been described as being accomplished by positioning a sheet of tissue, tissue having any suitable configuration can be positioned on a loading member in a method of loading tissue into a holding member. While step 1002 has been described as being accomplished such that a portion of the tissue is separated from the loading member by a fluid layer disposed between the tissue and the loading member, any suitable amount of tissue can be separated from a loading member by a fluid layer disposed between the tissue and the loading member. Examples of suitable amounts of tissue include an entire sheet of tissue, a majority of a sheet of tissue, more than half of a sheet of tissue, more than one quarter of a sheet of tissue, less than one quarter of a sheet of tissue, and any other amount of tissue considered suitable for a particular embodiment.

Step 1004 can be accomplished using any suitable technique or method of adjusting a position of the tissue and selection of a suitable technique or method can be based on various considerations, including the type of tissue being positioned within a holding member. Examples of techniques and methods considered suitable include using forceps, the hands of an individual, conventional tools, robotic systems, and any other technique or method considered suitable for a particular embodiment. Step 1004 is accomplished to remove any wrinkles in the tissue and/or to position the tissue such that it lays flat on the loading member and/or any other component.

Step 1006 can be accomplished using any suitable technique or method of positioning a clamping member on a loading member and selection of a suitable technique or method can be based on various considerations, including the structural arrangement of a clamping member and/or loading member. Examples of techniques and methods considered suitable include using the hands of an individual, using automated robotics systems, convention tools, such as hand tools, and any other technique or method considered suitable for a particular embodiment. It is considered advantageous to complete step 1006 such that the position of a loading member relative to a clamping member is maintained along an x-axis and a y-axis to reduce, or eliminate, any unintentional deformation and/or stress imparted on tissue positioned between a loading member and a clamping member during positioning of a clamping member relative a loading member and/or attachment of a clamping member to a loading member.

Step 1008 can be accomplished using any suitable technique or method of releasably attaching a clamping member to a loading member and selection of a suitable technique or method can be based on various considerations, including the structural arrangement of a clamping member and/or loading member. Examples of techniques and methods considered suitable include using threaded connections, snap fit attachments, using one or more connectors, one or more mating slots and projections, one or more sealed unions, tapered attachments, external clamps, pneumatic clamping mechanisms, adhesives, and any other technique or method of attachment considered suitable for a particular embodiment.

Figure 28:
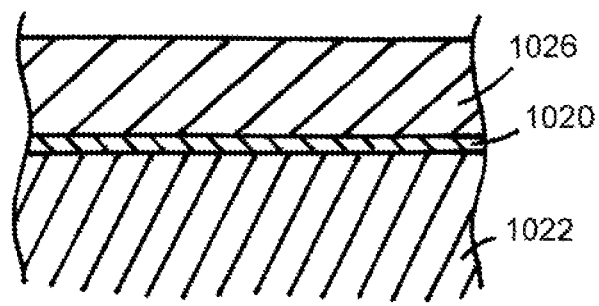
FIG. 28 is a partial sectional view of a sheet of tissue positioned between a clamping member and a loading member.

Step 1008 can be accomplished such that the tissue is in the clamped state. The phrase "clamped state" means the tissue is in a state in which forces are applied on the tissue by the clamping member and the loading member such that the portion of the tissue contacts the clamping member and the loading member. For example, a clamped state can include contact between a sealing member of a clamping member and the tissue such that the sealing member seals the tissue between the clamping member and the loading member to prevent leakage around the sealing member and maintain the position of the tissue during use. FIG. 28 illustrates a sheet of tissue 1020 positioned on a loading member 1022 such that the tissue 1020 is in its clamped state and a portion of the tissue 1020 contacts the clamping member 1026 and the loading member 1022.

While various steps, alternative steps, and optional steps have been described above with respect to the example method 1000, these steps, alternative steps, and optional steps can be included in, accomplished concurrently with, and/or accomplished in the alternative to, the method, steps, alternative steps, and/or optional steps described herein with respect to example method 1100, and/or example method 1200.

Figure 29:
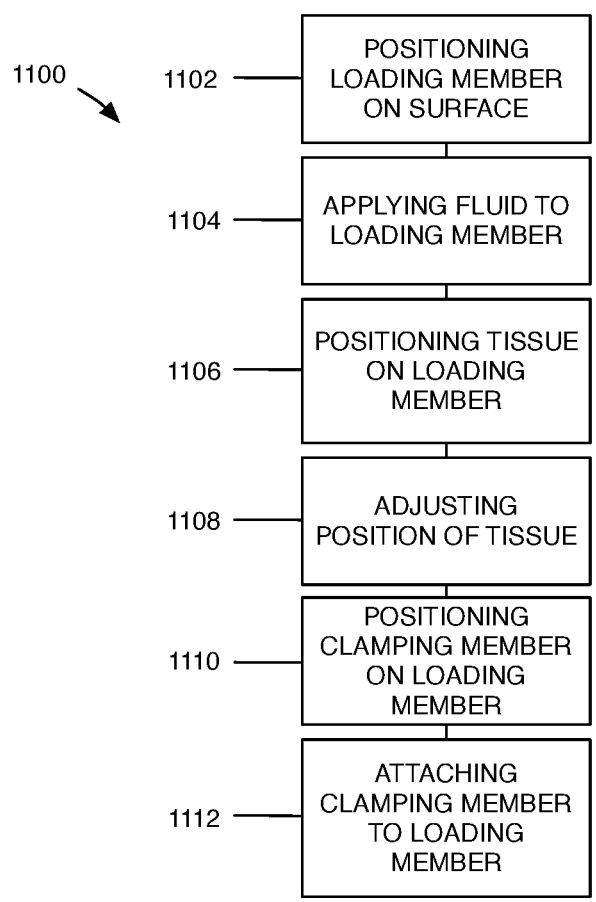
FIG. 29 is a schematic illustration of another example method of loading tissue into a holding member.

FIG. 29 is a schematic illustration of another example method 1100 of loading tissue into a holding member.

A step 1102 comprises positioning a loading member on flat surface with a guide member of the loading member directed away from the surface. Another step 1104 comprises applying a fluid to the loading member. Another step 1106 comprises positioning a sheet of tissue on a loading member such that the tissue is in its resting state and a portion of the tissue is separated from the loading member by a fluid layer disposed between the tissue and the loading member. Another step 1108 comprises adjusting the position of the tissue. Another step 1110 comprises positioning a clamping member on the loading member. Another step 1112 comprises releasably attaching the clamping member to the loading member such that the tissue is in the clamped state.

Step 1102 can be accomplished using any suitable loading member and selection of a suitable loading member can be based on various considerations, including the material that forms a loading member. Examples of loading members considered suitable to complete a method of loading tissue into a holding member include loading member 60, loading member 860, loading member 1760, and any other loading member considered suitable for a particular embodiment. A loading member can be positioned on any suitable surface, such as the surface of a table. In embodiments in which holding member 1760 is being used to complete method 1100, step 1102 can comprise positioning a loading member on a flat surface with a guide member of the loading member directed away from the surface such that the support member moves from the first position to the second position.

Figure 30:
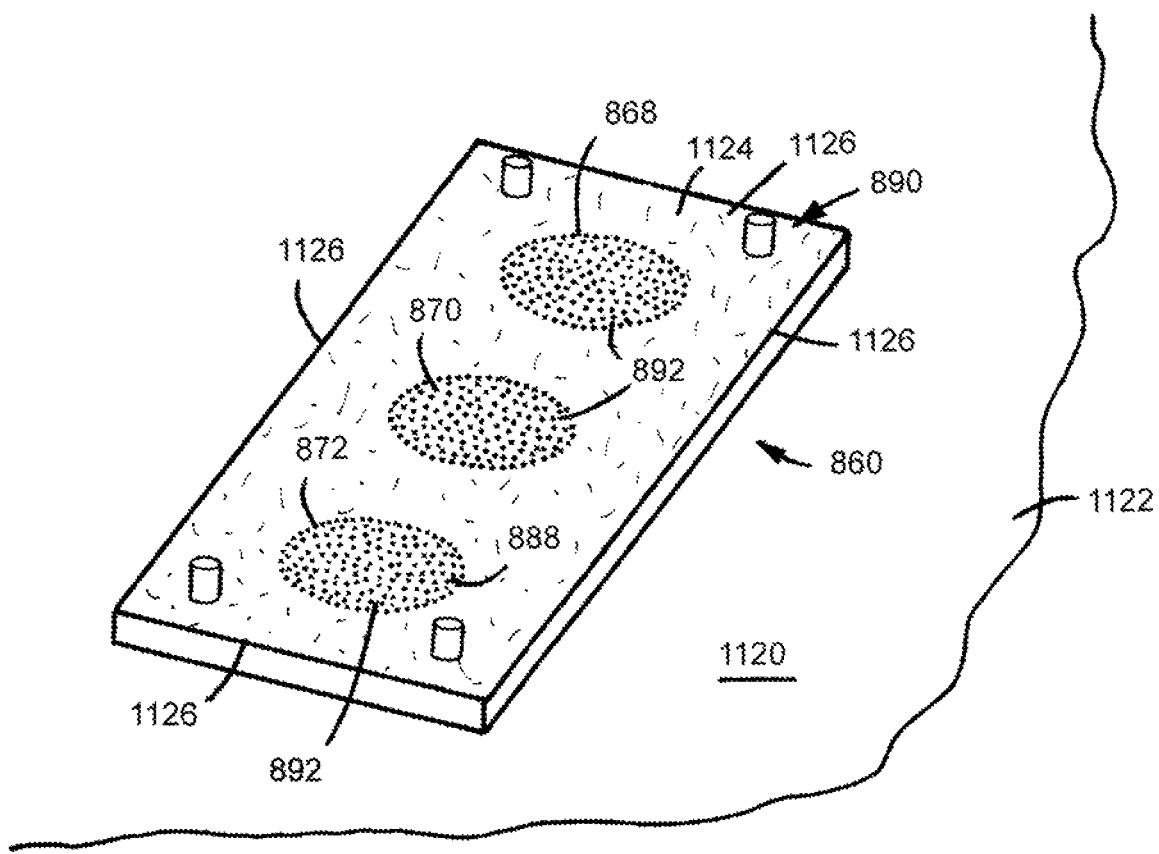
FIG. 30 illustrates a loading member positioned on a surface of a table.

Step 1104 can be accomplished using any suitable technique or method of applying any suitable fluid to a loading member and a fluid can be applied to any suitable portion of a loading member. Examples of techniques and methods of applying a fluid to a loading member considered suitable include applying a fluid layer prior to, during, and/or subsequent to, step 1102, activating a pump prior to and/or during step 1102 such that a fluid layer is positioned between tissue and a loading member, applying fluid to the loading member using an applicator, placing a loading member and/or other component within a fluid bath such that a top surface of the loading member and/or other component is disposed at, near, or below, the level of the fluid within the bath, and/or any other technique or method considered suitable for a particular embodiment. Examples of fluids considered suitable to apply to loading member include lubricious coatings, saline, phosphate buffered saline, those described herein, and any other fluid considered suitable for a particular embodiment. Examples of suitable portions of a loading member to apply a fluid include between a passageway and an edge defined by a loading member, on a support member of the loading member, on a perforated surface of the loading member, combinations of the portions described herein, and/or any other portion of a loading member considered suitable for a particular embodiment. FIG. 30 illustrates loading member 860 positioned on a surface 1120 of a table 1122 with the first guide member 890 directed away from the surface 1120. A phosphate buffered saline 1124 has been applied to the loading member 860 between the first portion 888 of each passageway of the plurality of passageways 868, 870, 872 and the edges 1126 of the loading member 860 and on the support member 892 spanning each passageway of the plurality of passageways 868, 870, 872. Optionally, step 1104 can be omitted from method 1100 in embodiments in which a fluid (e.g., lubricious coating) has already been applied to a loading member or in embodiments in which a loading member is formed of a non-stick material.

Step 1106 can be accomplished by positioning a single sheet of tissue over each portion of a passageway defined by a loading member or by positioning separate sheets of tissue over each portion of a passageway defined by a loading member. Depending on the number of sheets of tissue being positioned on a loading member, this step can alternatively be accomplished by positioning multiple sheets of tissue on a loading member sequentially to one another or concurrently with one another. Each sheet could be precut such that when disposed on a loading member the sheets do not overlap.

Step 1108 can be accomplished as described above with respect to step 1004. Step 1108 can be accomplished such that all wrinkles are removed from the tissue and/or the tissue is centered on each portion of a passageway defined by the loading member or on one portion of a passageway defined by the loading member. An optional step comprises trimming the tissue in embodiments in which the tissue obstructs or contacts any guide member and/or obstructs or contacts any openings and/or passageways used to releasably attach a loading member to a clamping member. Another optional step comprises applying fluid to the tissue subsequent to being positioned on a loading member (e.g., in embodiments in which multiple sheets of tissue are being positioned on a loading member). Another optional step comprises confirming that the tissue is large enough to contact the sealing member of a holding member (e.g., sealing member of clamping member) such that the tissue will seal the passageway defined by the holding member when the loading member and clamping member are attached to one another.

Step 1110 can be accomplished as described above with respect to step 1006.

Step 1112 can be accomplished as described above with respect to step 1008.

Depending on the structural arrangement of a clamping member (e.g., clamping member 262), an optional step comprises repeating step 1110 and step 1112 to accomplish attachment between each member of a clamping member and a loading member.

In embodiments in which holding member 1714 is being used to complete method 1100, an optional step comprises moving each support member of the plurality of support members from the second position to the first position. This optional step can be accomplished by removing the loading member 1760 from the flat surface.

While various steps, alternative steps, and optional steps have been described above with respect to the example method 1100, these steps, alternative steps, and optional steps can be included in, accomplished concurrently with, and/or accomplished in the alternative to, the method, steps, alternative steps, and/or optional steps described herein with respect to example method 1000, and/or example method 1200.

Figure 31:
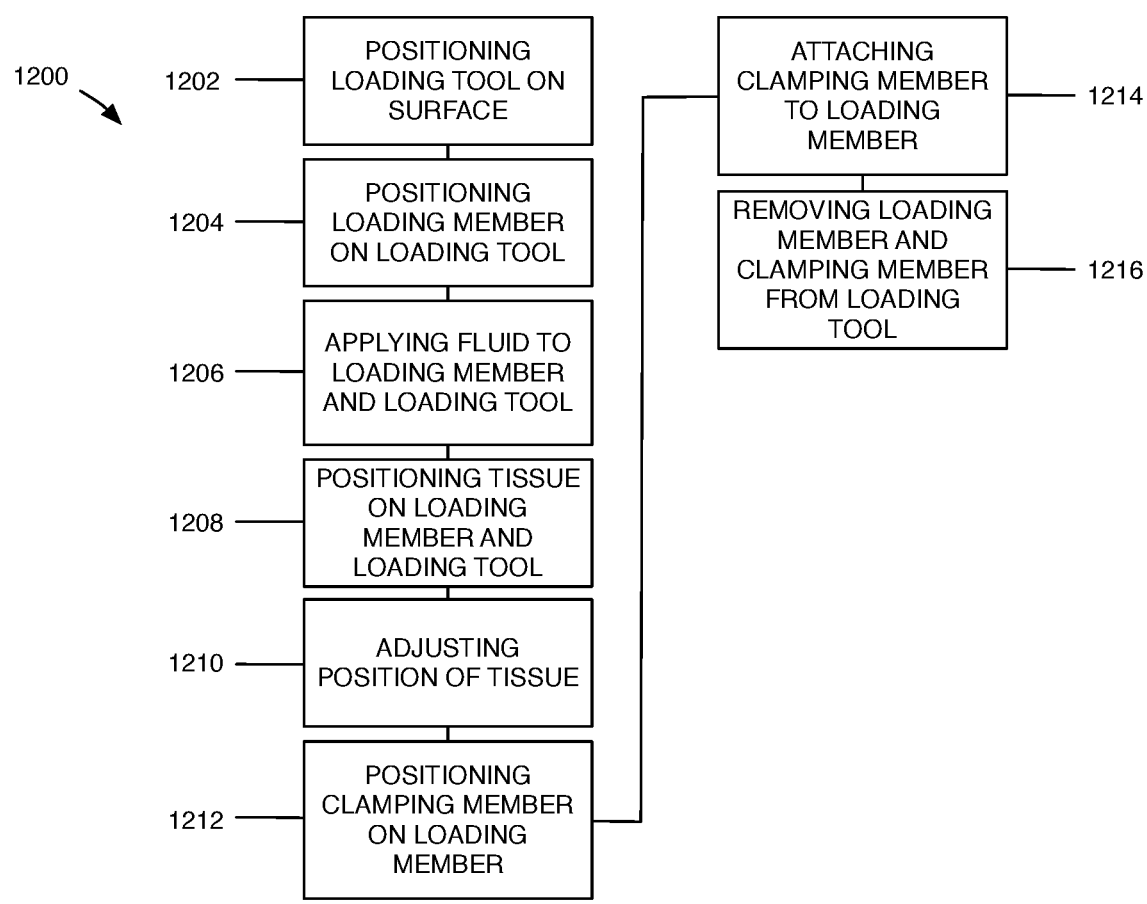
FIG. 31 is a schematic illustration of another example method of loading tissue into a holding member.

FIG. 31 is a schematic illustration of another example method 1200 of loading tissue into a holding member.

A step 1202 comprises positioning a loading tool on flat surface. Another step 1204 comprises positioning a loading member on the loading tool with a guide member of the loading member directed away from the loading tool. Another step 1206 comprises applying a fluid to the loading member and the loading tool. Another step 1208 comprises positioning a sheet of tissue on the loading member and the loading tool such that the tissue is in its resting state and a portion of the tissue is separated from the loading member and loading tool by a fluid layer disposed between the tissue and the loading member. Another step 1210 comprises adjusting the position of the tissue. Another step 1212 comprises positioning a clamping member on the loading member. Another step 1214 comprises releasably attaching the clamping member to the loading member such that the tissue is in the clamped state. Another step 1216 comprises removing the loading member and clamping member from the loading tool.

Figure 33A:
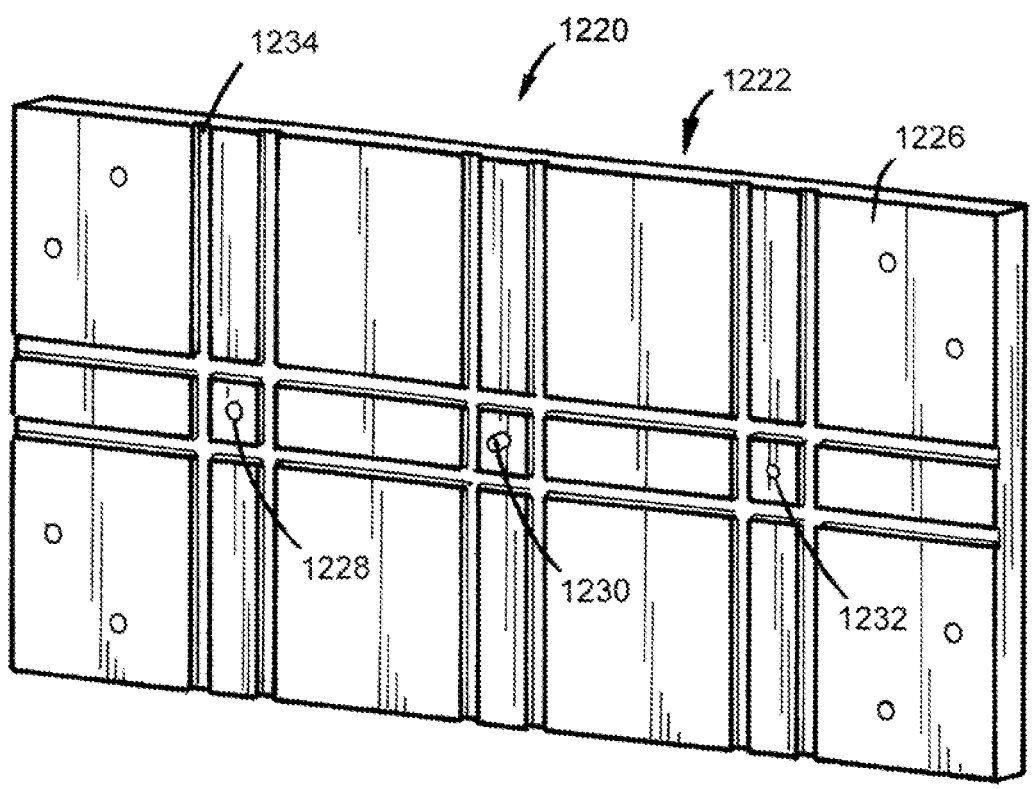
FIG. 33A is a perspective view of the base of the loading tool illustrated in FIG. 32.

Step 1202 can be accomplished using any suitable loading tool and selection of a suitable loading tool can be based on various considerations, including the material that forms a loading member intended to be positioned on the loading tool. FIGS. 32, 33, 33A, and 34 illustrate an example loading tool 1220. In FIGS. 32 and 33, loading member 260 is positioned on loading tool 1220. The loading tool 1220 includes a base 1222 and a plurality of caps 1224. The base 1222 has a main body 1226 that defines a plurality of passageways 1228, 1230, 1232 and a plurality of notches 1234. Each passageway of the plurality of passageways 1228, 1230, 1232 extends through the main body 1226. Each notch of the plurality of notches 1234 extends from a first edge of the main body 1226 to a second edge of the main body 1226. Each cap of the plurality of caps 1224 has a first end 1236, a second end 1238, and a main body 1240 that defines a support member 1242, a recess 1244, and an elongate member 1246. The support member 1242 is perforated and provides permeability across the material forming a cap such that the recess 1244 is in fluid communication with an environment exterior to the recess 1244 or with tissue when tissue is disposed on the first end of a cap. The elongate member 1246 provides a mechanism for attaching a cap 1224 to the base 1222 (e.g., using a threaded attachment). The support member 1242 defines a plurality of openings that are sized such that the fluid does not rapidly drain and the fluid remains on the support member 1242 during the loading process. A loading tool can be positioned on any suitable surface, such as the surface of a table. The outside diameter of each cap of the plurality of caps 1224 is less than the inside diameter of each passageway of the plurality of passageways defined by the loading member 260 (e.g., the outside diameters are undersized). This configuration along with the support member 1242 and the plurality of notches 1234 provide a mechanism for minimizing the vacuum that is created when that loading member 260 is removed from the loading tool 1220 and to avoid excessive tissue deformation. FIG. 32 illustrates loading tool 1220 positioned on a surface 1250 of a table 1252. As shown in FIG. 32, when the loading member 260 is positioned on the loading tool 1220, the support member 1242 is flush with the top surface of the loading member 260.

Step 1204 can be accomplished using any suitable loading member and selection of a suitable loading member can be based on various considerations, including the material that forms a loading member. Examples of loading members considered suitable to complete a method of loading tissue into a holding member include loading member 260, and any other loading member considered suitable for a particular embodiment. FIG. 32 illustrates loading member 260 positioned on the loading tool 1220 with the first guide member 290 directed away from the loading tool 1220.

Step 1206 can be accomplished using any suitable technique or method of applying any suitable fluid to a loading member and/or loading tool and a fluid can be applied to any suitable portion of a loading member and/or loading tool. Examples of techniques and methods of applying fluid to a loading member and/or loading tool considered suitable include applying a fluid layer prior to, during, and/or subsequent to, step 1202 and/or step 1204, activating a pump prior to and/or during step 1202 and/or step 1204 such that a fluid layer is positioned between tissue and a loading member and/or loading tool, applying fluid to the loading member and/or loading tool using an applicator, placing a loading member and/or loading tool within a fluid bath such that a top surface of the loading member and/or loading tool is disposed at, near, or below, the level of the fluid within the bath, and any other technique or method considered suitable for a particular embodiment. Examples of fluids considered suitable to apply to loading member and/or loading tool include lubricious coatings, saline, phosphate buffered saline, those described herein, and any other fluid considered suitable for a particular embodiment. Examples of suitable portions of a loading member and/or loading tool to apply a fluid include between a passageway and an edge defined by a loading member, on a support member of the loading member, on a perforated surface of a loading tool, and any other portion of a loading member and/or loading tool considered suitable for a particular embodiment. In embodiments in which loading tool 1220 is being utilized to complete method 1200, step 1206 can be accomplished by attaching a pump to tubular member 1246 of each cap of the plurality of caps 1224 such that the pump and each cap of the plurality of caps 1224 are in fluid communication and activating the pump such that fluid is applied to the loading tool 1220 and the loading member 260. Optionally, step 1206 can be omitted from method 1200 in embodiments in which a fluid (e.g., lubricious coating) has already been applied to a loading tool and/or loading member or in embodiments in which a loading tool and/or loading member is formed of a non-stick material.

Step 1208 can be accomplished by positioning a single sheet of tissue over each portion of a passageway defined by a loading member or by positioning separate sheets of tissue over each portion of a passageway defined by a loading member. Depending on the number of sheets of tissue being positioned on a loading member, an optional step comprises positioning multiple sheets of tissue on a loading member sequentially or concurrently with one another.

Step 1210 can be accomplished as described above with respect to step 1004 and/or step 1108. Step 1212 can be accomplished as described above with respect to step 1006. Step 1214 can be accomplished as described above with respect to step 1008. Depending on the structural arrangement of a clamping member (e.g., clamping member 262), an optional step comprises repeating step 1212 and step 1214 to accomplish attachment between each member of a clamping member and a loading member.

Step 1216 can be accomplished by applying a force on the loading member and/or clamping member away from the loading tool such that the loading member and clamping member are removed from the loading tool. It is considered advantageous to use a loading member and/or loading tool that includes a support member (e.g., perforated surface) to prevent a vacuum from being created between the surface on which tissue is disposed and the tissue.

While various steps, alternative steps, and optional steps have been described above with respect to the example method 1200, these steps, alternative steps, and optional steps can be included in, accomplished concurrently with, and/or accomplished in the alternative to, the method, steps, alternative steps, and/or optional steps described herein with respect to example method 1000, and/or example method 1100.

Figure 35:
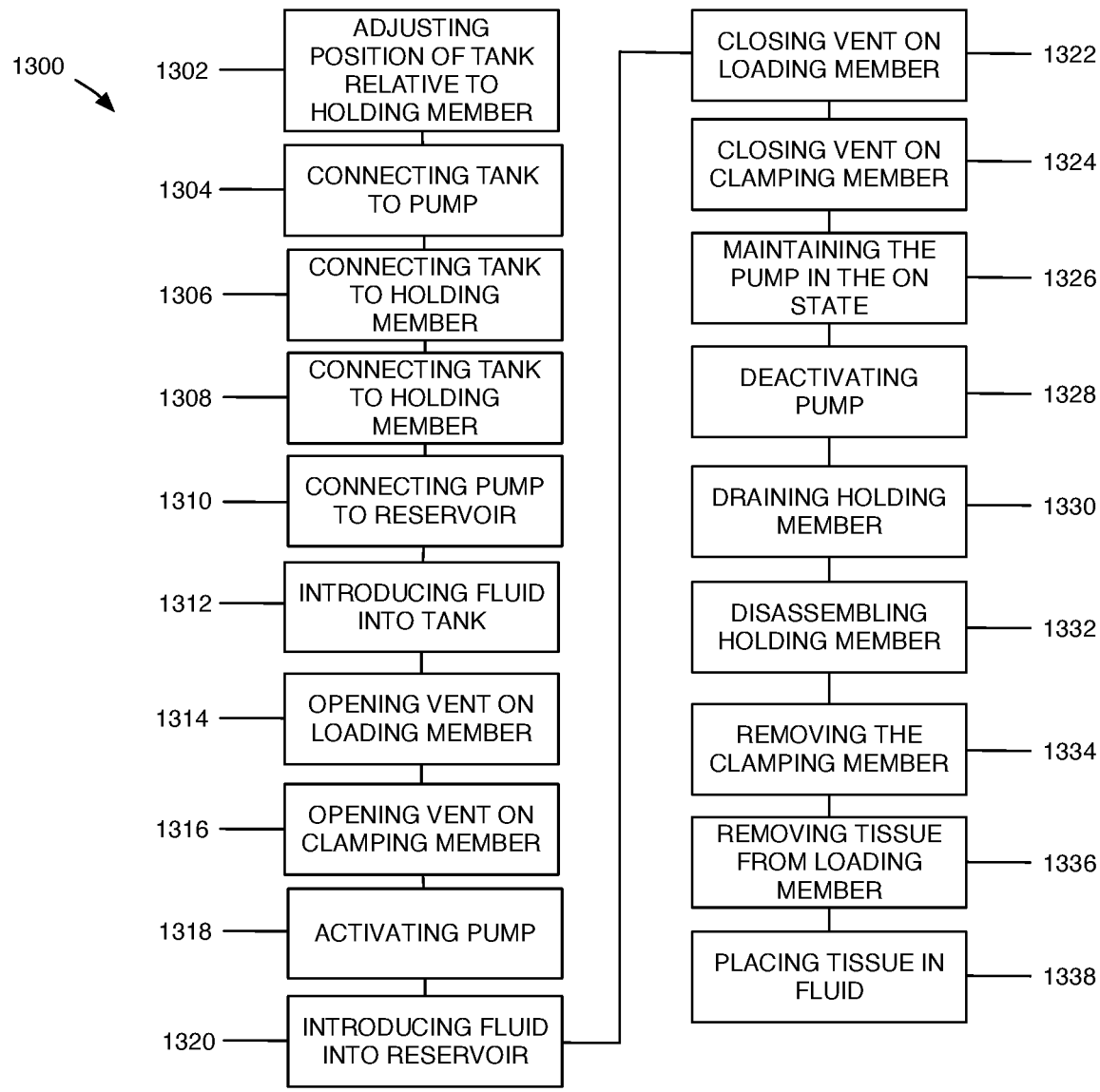
FIG. 35 is a schematic illustration of an example method of processing tissue.

FIG. 35 is a schematic illustration of an example method 1300 of processing tissue.

A step 1302 comprises adjusting the position of a tank relative to a holding member along a vertical axis. The holding member has tissue disposed between a loading member and a clamping member. Another step 1304 comprises connecting the tank to a pump such that a first portion of the tank is in fluid communication with the pump. Another step 1306 comprises connecting the tank to the holding member such that the first portion of the tank is in fluid communication with the holding member. Another step 1308 comprises connecting the tank to the holding member such that a second portion of the tank is in fluid communication with the holding member. Another step 1310 comprises connecting the pump to a reservoir such that the pump is in fluid communication with the reservoir. Another step 1312 comprises introducing a fluid into the tank. Another step 1314 comprises opening a vent on the loading member. Another step 1316 comprises opening a vent on the clamping member. Another step 1318 comprises activating the pump. Another step 1320 comprises introducing fluid into the reservoir while the pump is in an on state. Another step 1322 comprises closing the vent on the loading member. Another step 1324 comprises closing the vent on the clamping member. Another step 1326 comprises maintaining the pump in the on state for a period of time such that a differential pressure is applied to the tissue. Another step 1328 comprises deactivating the pump. Another step 1330 comprises draining the holding member. Another step 1332 comprises disassembling the holding member. Another step 1334 comprises removing the clamping member from the loading member. Another step 1336 comprises removing tissue from the loading member. Another step 1338 comprises placing the tissue in a fluid for a period of time.

Step 1302 can be accomplished by adjusting the position of any suitable tank relative to any suitable holding member. For example, the tank 12 illustrated in FIG. 1 can be adjusted relative to the holding member 14. A holding member utilized in a method of processing tissue can be pre-loaded with tissue disposed between a loading member and a clamping member. For example, tissue can be positioned within a holding member using the methods described herein, such as method 1000, method 1100, and/or method 1200.

Step 1304 can be accomplished by attaching a first elongate tubular member to the tank and the pump such that the first portion of the tank is in fluid communication with the pump.

Step 1306 can be accomplished by attaching a second elongate tubular member to the tank and the holding member such that the first portion of the tank is in fluid communication with the holding member (e.g., first holding member chamber).

Step 1308 can be accomplished by attaching a third elongate tubular member to the tank and the holding member such that the second portion of the tank is in fluid communication with the holding member (e.g., second holding member chamber).

Step 1310 can be accomplished by attaching a fourth elongate tubular member to the pump and a reservoir such that the pump is in fluid communication with the reservoir (e.g., third portion of tank). Depending on the structural arrangement of a differential pressure material processing system, in alternative embodiments steps 1304 through 1310 could be omitted from a method of processing tissue when a system is preconfigured as described with respect to steps 1302 through 1310.

Step 1312 can be accomplished by introducing any suitable type and amount of fluid into the tank. The amount of fluid introduced into a tank will vary and depend on the dimensions of the tank. Examples of amounts of fluid considered suitable to introduce into a tank include 0.5 liters, 1 liter, 1.5 liters, 2 liters, 2.5 liters, 3 liters, 4 liters, 5 liters, 6 liters, 7 liters, 8 liters, 9 liters, 10 liters, more than 4 liters, and any other amount considered suitable for a particular embodiment. Examples of suitable fluids considered suitable to introduce into a tank include chemical fixatives, such as aldehydes, e.g., formaldehyde, glutaraldehyde, and formalin, and carbodiimides, such as ethyl dimethylaminopropyl carbodiimide, dicyclohexylcarbodiimide, solutions, tanning agents, tanning agents in a buffering solution, and any other fluid considered suitable for a particular embodiment. Fluid can be introduced into any suitable portion of a tank (e.g., first portion, second portion, third portion). In the embodiment illustrated in FIG. 1, fluid can be introduced into the first portion of the tank 12 such that it spills into the second portion of the tank 12 (e.g., second recess 30) and the third portion of the tank 12 (e.g., third recess 32).

Step 1314 and step 1316 can be accomplished by applying a force on a vent to move it to an open configuration.

Step 1318 can be accomplished by moving the pump from an off state to an on state. It is considered advantageous to adjust the rate at which fluid is pumped into a tank such that it does not create turbulence within the tank. Once the pump is activated, fluid will flow from the first portion of the tank and into the second portion of the tank, from the second portion of the tank to the third portion of the tank, from the third portion of the tank to the pump inlet, from the first portion of the tank to the holding member (e.g., first holding member chamber), and from the second portion of the tank to the holding member (e.g., second holding member chamber).

Step 1320 can be accomplished by introducing additional fluid into the reservoir. For example, additional fluid could be added such that the total fluid within the system is about 4 liters. In alternative embodiments, step 1320 could be omitted from method 1300 in which additional fluid is not needed.

An optional step comprises adjusting the rate of pumping such that only a small amount of overflow from the first portion of the tank to the second portion of the tank is achieved. This optional step can be completed after the holding member fills and the tank has reached overflow capacity and a constant, or substantially constant, pressure differential is maintained within the holding member. Another optional step comprises preloading the tank with fluid. This step can be accomplished such that both the first portion and the second portion of the tank are filled at a similar rate to avoid excessive deformation of the tissue in one direction within the holding member.

The differential pressure being applied to tissue can vary during a method of processing tissue due to the permeability of the tissue, which results in fluid passing through the tissue from a first holding member chamber to a second holding member chamber. Therefore, an optional step comprises adjusting the differential pressure being applied to the tissue. This optional step can be accomplished by adjusting the rate of fluid being pumped by the pump, adjusting the height of a first wall and/or second wall defined by a tank, and/or any other technique or method considered suitable for a particular embodiment. Another optional step comprises determining the pressure differential between the first holding member chamber and second holding member chamber. This optional step allows for a determination as to whether an adjustment to the differential pressure is necessary and can be accomplished using a first pressure transducer disposed within the first holding member chamber and a second pressure transducer disposed within the second holding member chamber or a manometer in communication with the first holding member chamber and the second holding member chamber. Another optional step comprises determining the characteristics of the tissue. This optional step can be accomplished using an ultrasound transducer in communication with one, or both, of the first holding member chamber and second holding member chamber. These optional steps can be accomplished while a pump is in an on state and a differential pressure is being applied to the tissue or in an off state (e.g., fluid is disposed between a transducer and the tissue). Any suitable characteristic can be determined and selection of a suitable characteristic can be based on various considerations, including the type of tissue being processed. Examples of characteristics considered suitable to determine include deformation of tissue, deformation over time, deformation over load, deformation over applied pressure, combinations of deformation over time, deformation over load, and deformation over applied pressure, detection of local defects within a tissue, fixation status, and any other characteristic considered suitable for a particular embodiment. For example, characteristics relating to deformation over time, deformation over load, and/or deformation over applied pressure can be used to calculate a modulus of a tissue being processed. In addition, detection of local defects within a tissue can be utilized during manufacture such that defective portion of the tissue are not used in a final product.

Step 1322 and step 1324 can be accomplished by applying a force on a vent to move it to a closed configuration. Each of step 1322 and step 1324 can optionally be completed just before the holding member reaches full capacity. An optional step comprises removing air trapped within holding member (e.g., by tilting the holding member such that air bubbles migrate up the inlet tubing into the tanks).

Figure 35A:
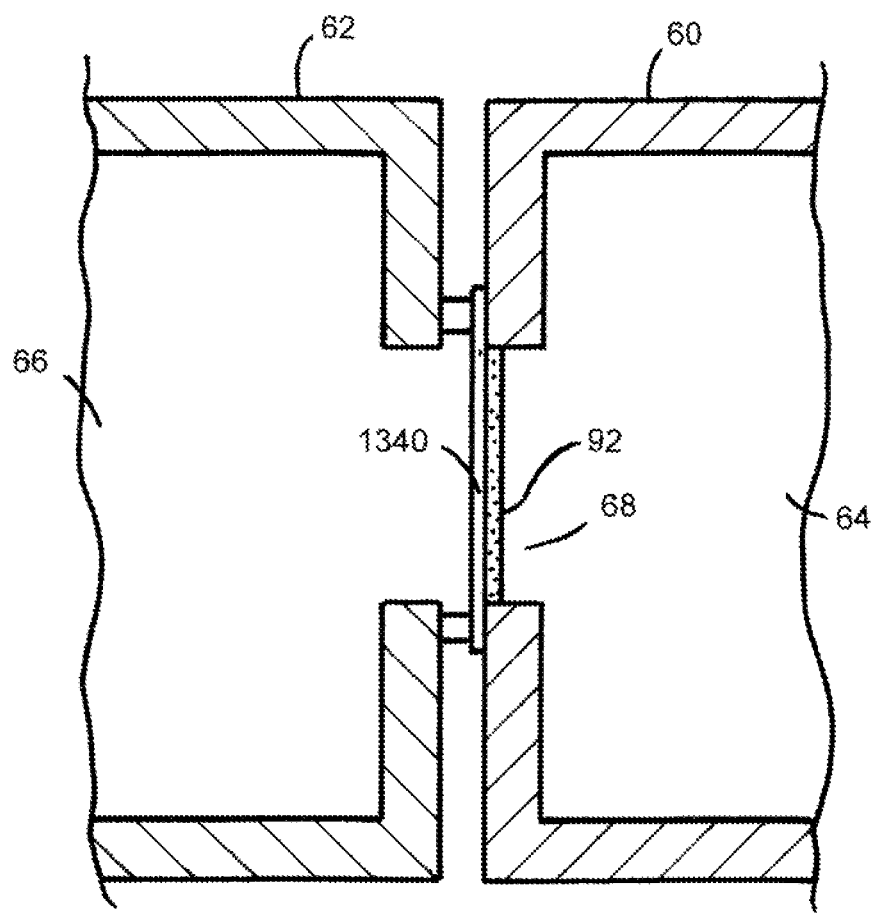
FIG. 35A is a partial sectional view of a sheet of tissue prior to the application of differential pressure.
Figure 35B:
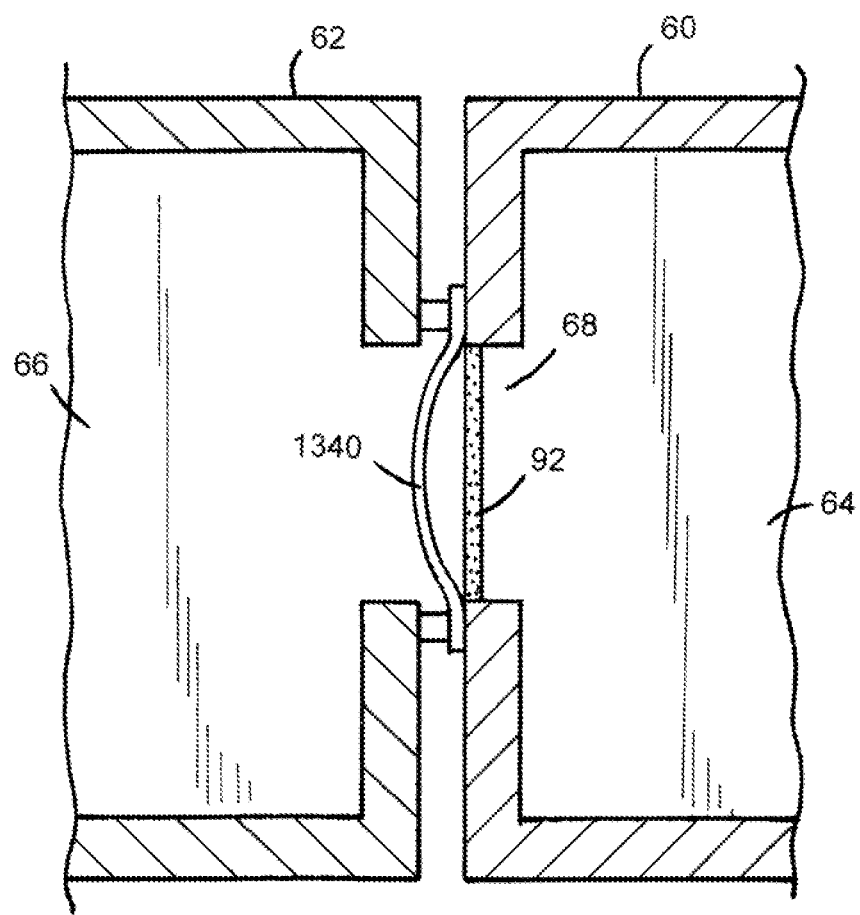
FIG. 35B is a partial sectional view of a sheet of tissue that is being processed under differential pressure.

Step 1326 can be accomplished for any period of time, such as one or more minutes, one or more hours, and/or one or more days. For example, step 1326 can be accomplished for a period of time equal to, greater than, less than, or about four hours. Any suitable differential pressure can be applied to tissue and selection of a suitable differential pressure to apply to tissue can be based on various considerations, such as the desired characteristics intended to be imparted on the tissue. Examples of suitable differential pressures considered suitable to apply to tissue being processed using the methods described herein include those that are equal to, less than, greater than, or about 0.25 millimeters of mercury, 0.5 millimeters of mercury, 1 millimeter of mercury, 1.5 millimeters of mercury, 1.75 millimeters of mercury, between about 0.25 millimeters of mercury and about 1.75 millimeters of mercury, and any other differential pressure considered suitable for a particular embodiment. FIG. 35A illustrates a sheet of tissue 1340 prior the application of differential pressure such that the tissue is in a first, undeformed configuration. As shown in FIG. 35A, the first configuration of the tissue 1340 is generally planar. However, a tissue processed under differential pressure can have any suitable first, undeformed configuration. FIG. 35B illustrates the tissue 1340 being processed under differential pressure such that the tissue is in a second, deformed configuration. As shown in FIG. 35B, the second configuration of the tissue 1340 is different than the first configuration and is domed such that the tissue 1340 distends towards the second holding member chamber 66 (e.g., low-pressure portion). The degree of distension imparted on tissue during differential pressure treatment will vary depending on the stiffness of the tissue. In some embodiments, depending on the type of tissue being processed, the application of differential pressure provides a mechanism for imparting a constant, or substantially constant, and uniform, or substantially uniform, deformation on the tissue as it is crosslinked during fixation.

Step 1328 can be accomplished by moving the pump from an on state to an off state.

Step 1330 can be accomplished using any suitable technique or method of draining a holding member. For example, the fluid within a holding member can be removed by moving one or more vents of the holding member to an open configuration and draining the fluid through the one or more vents and/or moving one or more drains of the holding member to an open configuration and draining the fluid through the one or more drains.

Step 1332 can be accomplished using any suitable technique or method of disassembling a holding member.

Step 1334 can be accomplished using any suitable technique or method of removing a clamping member from a loading member and selection of a suitable technique or method can be based on various considerations, including the structural arrangement of a clamping member and/or loading member. Examples of techniques and methods considered suitable include using the hands of an individual, using automated robotics systems, convention tools, such as hand tools, and any other technique or method considered suitable for a particular embodiment. It is considered advantageous to complete step 1334 such that the position of a loading member relative to a clamping member is maintained along an x-axis and a y-axis to reduce, or eliminate, any unintentional deformation and/or stress imparted on tissue positioned between a loading member and a clamping member.

Step 1336 can be accomplished using any suitable technique or method of removing tissue from a loading member and selection of a suitable technique or method can be based on various considerations, including the structural arrangement of a loading member. Examples of techniques and methods considered suitable include using the hands of an individual, using automated robotics systems, convention tools, such as hand tools, and any other technique or method considered suitable for a particular embodiment. In an alternative embodiment, an appropriately sized punch could be used to detach the tissue without removing a clamping member, which would complete any desired trimming while concurrently removing the tissue from a loading member.

An optional step that can be completed prior to, or subsequent to, step 1336 comprises trimming the tissue into a desired geometry (e.g., circular). For example, in some embodiments, the portion of tissue disposed between the clamping member and the loading member (e.g., adjacent an O-ring) will not have desired properties and can be discarded. Another optional step that can be completed prior to, or subsequent to, step 1336 comprises marking the orientation of the tissue.

Step 1338 can be accomplished by placing the tissue in any suitable fluid for any period of time. Examples of suitable fluids include chemical fixatives, such as aldehydes, e.g., formaldehyde, glutaraldehyde, and formalin, and carbodiimides, such as ethyl dimethylaminopropyl carbodiimide, dicyclohexylcarbodiimide, solutions, storage solutions, tanning agents, tanning agents in a buffering solution, and any other fluid considered suitable for a particular embodiment. Examples of suitable period of time include one or more minutes, hours, days, weeks, months, and any other period of time considered suitable for a particular embodiment. For example, the tissue can be placed within a fixation solution for twenty hours.

An optional step that can be completed subsequent to step 1338 comprises placing the tissue in a storage solution and storing at about 4° C. Alternative embodiments, however, could store the tissue at other temperatures, such as those equal to, greater than, less than, or about 3° C., 4° C., 5° C., and any other temperature considered suitable for a particular embodiment.

Any of the materials described herein (e.g., tissue) can be processed using the systems, apparatus, methods, steps, alternative steps, and/or optional steps described herein to produce a product, such as a tissue product, that is processed using differential pressure. For example, a sheet of tissue that is produced through the application of differential pressure using one or more of the systems and/or apparatus described herein and/or using one or more of the methods, steps, alternative steps, and/or optional steps described herein can be claimed.

In alternative embodiments, depending on the permeability of the tissue being processed, step 1304, step 1310, step 1318, step 1326, and/or step 1328 can be omitted from method 1300. For example, these steps can be omitted from a method of processing tissue in embodiments in which the tissue being processed is impermeable, or substantially impermeable, and/or a tank does not define a second passageway (e.g., second passageway 36) and a fourth passageway (e.g., fourth passageway 40).

While various steps, alternative steps, and optional steps have been described above with respect to the example method 1300, these steps, alternative steps, and optional steps can be included in, accomplished concurrently with, and/or accomplished in the alternative to, the method, steps, alternative steps, and/or optional steps described herein with respect to example method 1400, example method 1500, and/or example method 1600.

Figure 36:
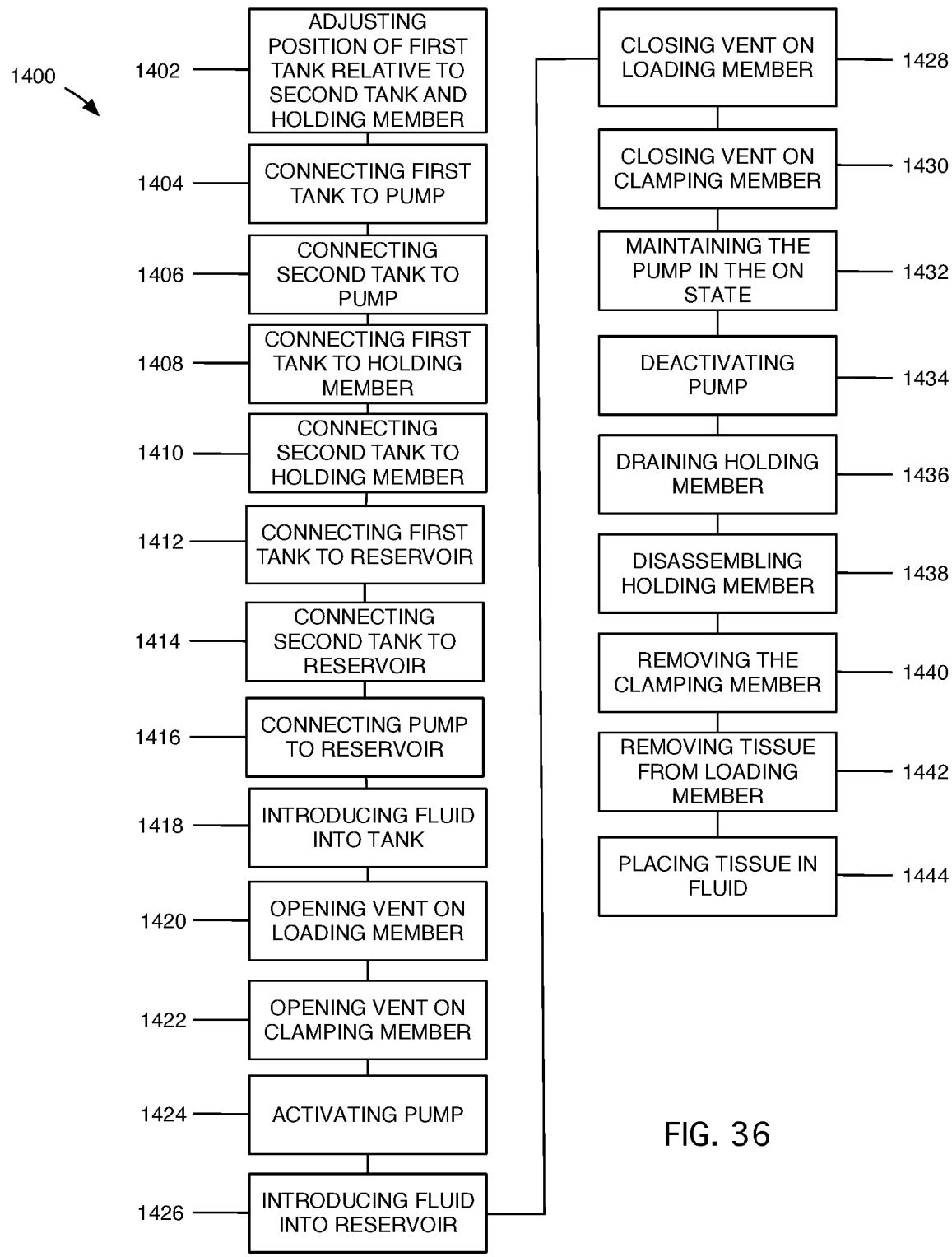
FIG. 36 is a schematic illustration of another example method of processing tissue.

FIG. 36 is a schematic illustration of another example method 1400 of processing tissue.

A step 1402 comprises adjusting the position of a first tank relative to a second tank and a holding member along a vertical axis. The holding member has tissue disposed between a loading member and a clamping member. Another step 1404 comprises connecting the first tank to a pump such that the first portion of the first tank is in fluid communication with the pump. Another step 1406 comprises connecting the second tank to the pump such that the first portion of the second tank is in fluid communication with the pump. Another step 1408 comprises connecting the first tank to a holding member such that the first portion of the first tank is in fluid communication with the holding member. Another step 1410 comprises connecting the second tank to the holding member such that the first portion of the second tank is in fluid communication with the holding member. Another step 1412 comprises connecting the first tank to a reservoir such that the first tank is in fluid communication with the reservoir. Another step 1414 comprises connecting the second tank to the reservoir such that the second tank is in fluid communication with the reservoir. Another step 1416 comprises connecting the pump to the reservoir such that the pump is in fluid communication with the reservoir. Another step 1418 comprises introducing fluid into the tank. Another step 1420 comprises opening a vent on the loading member. Another step 1422 comprises opening a vent on the clamping member. Another step 1424 comprises activating the pump. Another step 1426 comprises introducing fluid into reservoir while the pump is in an on state. Another step 1428 comprises closing the vent on the loading member. Another step 1430 comprises closing the vent on the clamping member. Another step 1432 comprises maintaining the pump in the on state for a period of time such that a differential pressure is applied to the tissue. Another step 1434 comprises deactivating the pump. Another step 1436 comprises draining the holding member. Another step 1438 comprises disassembling the holding member. Another step 1440 comprises removing the clamping member. Another step 1442 comprises removing the tissue from the loading member. Another step 1444 comprises placing the tissue in a fluid for a period of time.

Step 1402 can be accomplished by adjusting the position of any suitable first tank relative to any suitable second tank and any suitable holding member. For example, the first tank 212 illustrated in FIG. 6 can be adjusted relative to the second tank 320 and the holding member 214. An optional step comprises confirming that each of the first tank, the second tank, and/or the holding member is level.

Step 1404 can be accomplished by attaching a first elongate tubular member to the first tank and the pump such that the first portion of the first tank is in fluid communication with the pump.

Step 1406 can be accomplished by attaching a second elongate tubular member to the second tank and the pump such that the first portion of the second tank is in fluid communication with the pump.

Step 1408 can be accomplished by attaching a third elongate tubular member to the first tank and the holding member such that the first portion of the first tank is in fluid communication with the holding member (e.g., first holding member chamber).

Step 1410 can be accomplished by attaching a fourth elongate tubular member to the second tank and the holding member such that the first portion of the second tank is in fluid communication with the holding member (e.g., second holding member chamber).

Step 1412 can be accomplished by attaching a fifth elongate tubular member to the first tank and the reservoir such that the second portion (e.g., second recess) of the first tank is in fluid communication with the reservoir.

Step 1414 can be accomplished by attaching a sixth elongate tubular member to the second tank and the reservoir such that the second portion (e.g., second recess) of the second tank is in fluid communication with the reservoir.

Step 1416 can be accomplished by attaching a seventh elongate tubular member to the reservoir and the pump such that the reservoir is in fluid communication with the pump. Depending on the structural arrangement of a differential pressure material processing system, in alternative embodiments steps 1402 through 1416 could be omitted from a method of processing tissue when a system is preconfigured as described with respect to steps 1402 through 1416.

Step 1418 can be accomplished as described above with respect to step 1312 but can be accomplished with respect to both the first portion of the first tank and the first portion of the second tank. Alternatively, or in combination with introducing fluid into the first tank and the second tank, another step comprises introducing fluid to the reservoir.

Step 1420 and step 1422 can be accomplished as described above with respect to step 1314 and step 1316. Step 1424 can be accomplished as described above with respect to step 1318. Step 1426 can be accomplished as described above with respect to step 1320. Step 1428 and step 1430 can be accomplished as described above with respect to step 1322 and step 1324.

Step 1432 can be accomplished as described above with respect to step 1326. The differential pressure being applied to tissue can vary during a method of processing tissue due to the permeability of the tissue, which results in fluid passing through the tissue from a first holding member chamber to a second holding member chamber. Therefore, an optional step comprises adjusting the differential pressure being applied to the tissue. This optional step can be accomplished by adjusting the rate of fluid being pumped by the pump, adjusting the height of a first tank relative to a second tank and/or a holding member, and/or any other technique or method considered suitable for a particular embodiment. Another optional step comprises determining the pressure differential between the first holding member chamber and second holding member chamber. This optional step allows for a determination as to whether an adjustment to the differential pressure is necessary and can be accomplished using a first pressure transducer disposed within the first holding member chamber and a second pressure transducer disposed within the second holding member chamber. Another optional step comprises determining the characteristics of the tissue. This optional step can be accomplished using an ultrasound transducer in communication with one, or both, of the first holding member chamber and second holding member chamber. These optional steps can be accomplished while a pump is in an on state and a differential pressure is being applied to the tissue.

Step 1434 can be accomplished as described above with respect to step 1328. Step 1436 can be accomplished as described above with respect to step 1330. Step 1438 can be accomplished as described above with respect to step 1332. Step 1440 can be accomplished as described above with respect to step 1334. Step 1442 can be accomplished as described above with respect to step 1336. Step 1444 can be accomplished as described above with respect to step 1338.

In alternative embodiments, depending on the permeability of the tissue being processed, step 1404, step 1406, step 1412, step 1414, step 1416, step 1424, step 1432, and/or step 1434 can be omitted from method 1400. For example, these steps can be omitted from a method of processing tissue in embodiments in which the tissue being processed is impermeable, or substantially impermeable, and/or a first tank does not define a second passageway (e.g., second passageway 236) and a third passageway (e.g., third passageway 238) and a second tank does not define a second passageway (e.g., second passageway 342) and a third passageway (e.g., third passageway 344).

While various steps, alternative steps, and optional steps have been described above with respect to the example method 1400, these steps, alternative steps, and optional steps can be included in, accomplished concurrently with, and/or accomplished in the alternative to, the method, steps, alternative steps, and/or optional steps described herein with respect to example method 1300, example method 1500, and/or example method 1600.

Figure 37:
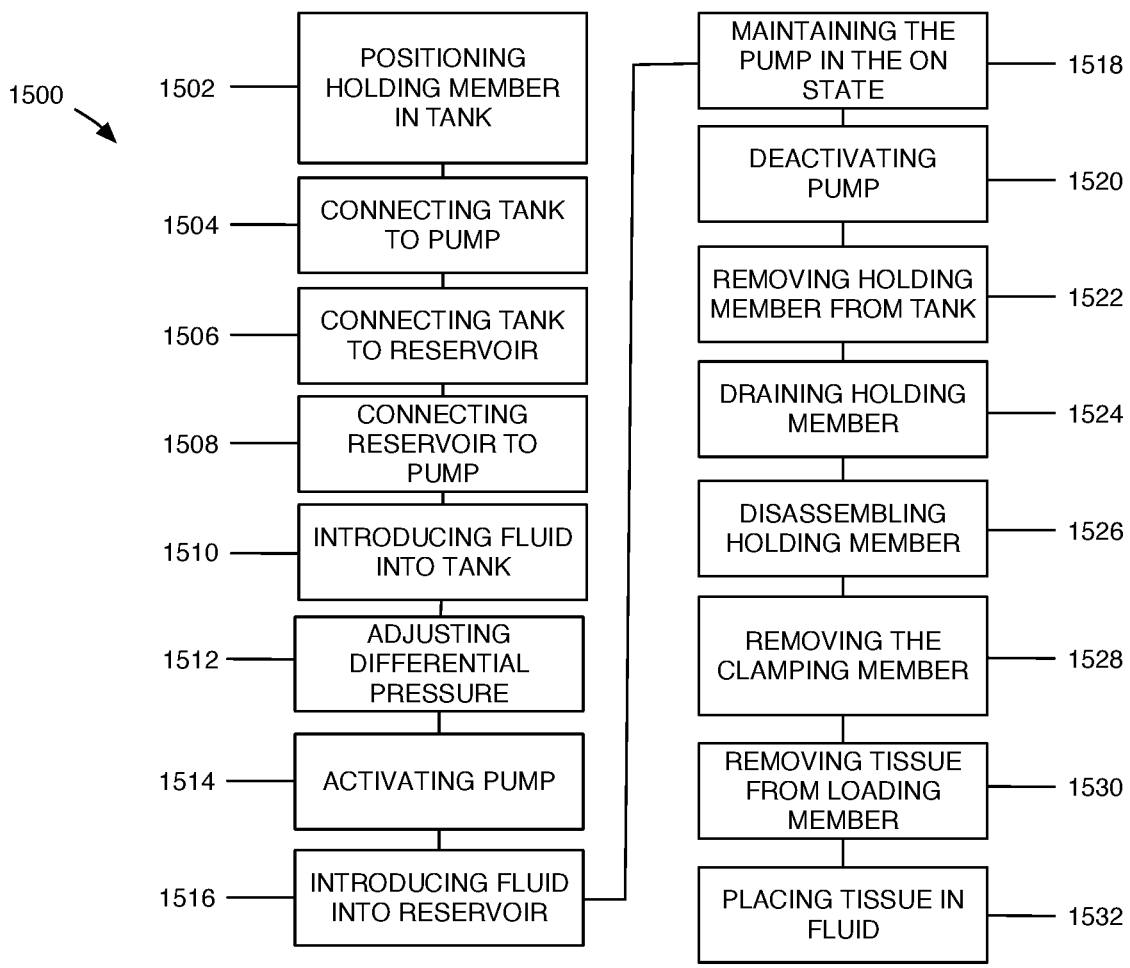
FIG. 37 is a schematic illustration of another example method of processing tissue.

FIG. 37 is a schematic illustration of another example method 1500 of processing tissue.

A step 1502 comprises positioning a holding member in a tank. The holding member has tissue disposed between a loading member and a clamping member. Another step 1504 comprises connecting the tank to a pump such that a first portion of the tank is in fluid communication with the pump. Another step 1506 comprises connecting the tank to a reservoir such that the second portion of the tank is in fluid communication with the reservoir. Another step 1508 comprises connecting the reservoir to the pump such that the reservoir is in fluid communication with the pump. Another step 1510 comprises introducing a fluid into the tank. Another step 1512 comprises adjusting the differential pressure between the first portion of the tank and the second portion of the tank. Another step 1514 comprises activating the pump. Another step 1516 comprises introducing fluid into the reservoir while the pump is in an on state. Another step 1518 comprises maintaining the pump in the on state for a period of time such that a differential pressure is applied to the tissue. Another step 1520 comprises deactivating the pump. Another step 1522 comprises removing the holding member from the tank. Another step 1524 comprises draining the holding member. Another step 1526 comprises disassembling the holding member. Another step 1528 comprises removing the clamping member from the loading member. Another step 1530 comprises removing tissue from the loading member. Another step 1532 comprises placing the tissue in a fluid for a period of time.

Step 1502 can be accomplished by positioning any suitable holding member in any suitable tank. For example, the holding member 514 illustrated in FIG. 17 can be positioned within the tank 512.

Step 1504 can be accomplished by attaching a first elongate tubular member to the tank and the pump such that the first portion of the tank is in fluid communication with the pump.

Step 1506 can be accomplished by attaching a second elongate tubular member to the tank and the reservoir such that the second portion of the tank is in fluid communication with the reservoir.

Step 1508 can be accomplished by attaching a third elongate tubular member to the reservoir and the pump such that the reservoir is in fluid communication with the pump. Depending on the structural arrangement of a differential pressure material processing system, in alternative embodiments steps 1502 through 1508 could be omitted from a method of processing tissue when a system is preconfigured as described with respect to steps 1502 through 1508.

Step 1510 can be accomplished as described above with respect to step 1312. In method 1500, however, the fluid can be introduced into one, or both, of the first portion of the tank and the second portion of the tank.

The differential pressure being applied to tissue can vary during a method of processing tissue due to the permeability of the tissue, which results in fluid passing through the tissue from a first holding member chamber to a second holding member chamber. Step 1512 can be accomplished by adjusting the rate of fluid being pumped by the pump, manipulating the position of one or more pistons of the plurality of pistons 624, manipulating the position of the second passageway 536, and/or any other technique or method considered suitable for a particular embodiment. An optional step comprises determining the pressure differential between the first holding member chamber and second holding member chamber. This optional step allows for a determination as to whether an adjustment to the differential pressure is necessary and can be accomplished using a first pressure transducer disposed within the first holding member chamber and a second pressure transducer disposed within the second holding member chamber. Another optional step comprises determining the characteristics of the tissue. This optional step can be accomplished using an ultrasound transducer in communication with one, or both, of the first holding member chamber and second holding member chamber. These optional steps can be accomplished while a pump is in an on state and a differential pressure is being applied to the tissue.

Step 1514 can be accomplished as described above with respect to step 1318. Step 1516 can be accomplished as described above with respect to step 1320. Step 1518 can be accomplished as described above with respect to step 1326. Step 1520 can be accomplished as described above with respect to step 1328.

Step 1522 can be accomplished by applying a force on the holding member away from the tank until the holding member is free of the tank.

Step 1524 can be accomplished as described above with respect to step 1330. Step 1526 can be accomplished as described above with respect to step 1332. Step 1528 can be accomplished as described above with respect to step 1334. Step 1530 can be accomplished as described above with respect to step 1336. Step 1532 can be accomplished as described above with respect to step 1338.

In alternative embodiments, depending on the permeability of the tissue being processed, step 1504, step 1506, step 1508, step 1514, step 1518, and/or step 1520 can be omitted from method 1500. For example, these steps can be omitted from a method of processing tissue in embodiments in which the tissue being processed is impermeable, or substantially impermeable, and/or a tank does not define a first passageway (e.g., first passageway 534) and a second passageway (e.g., third passageway 536).

While various steps, alternative steps, and optional steps have been described above with respect to the example method 1500, these steps, alternative steps, and optional steps can be included in, accomplished concurrently with, and/or accomplished in the alternative to, the method, steps, alternative steps, and/or optional steps described herein with respect to the example method 1300, example method 1400, and/or example method 1600.

Figure 38:
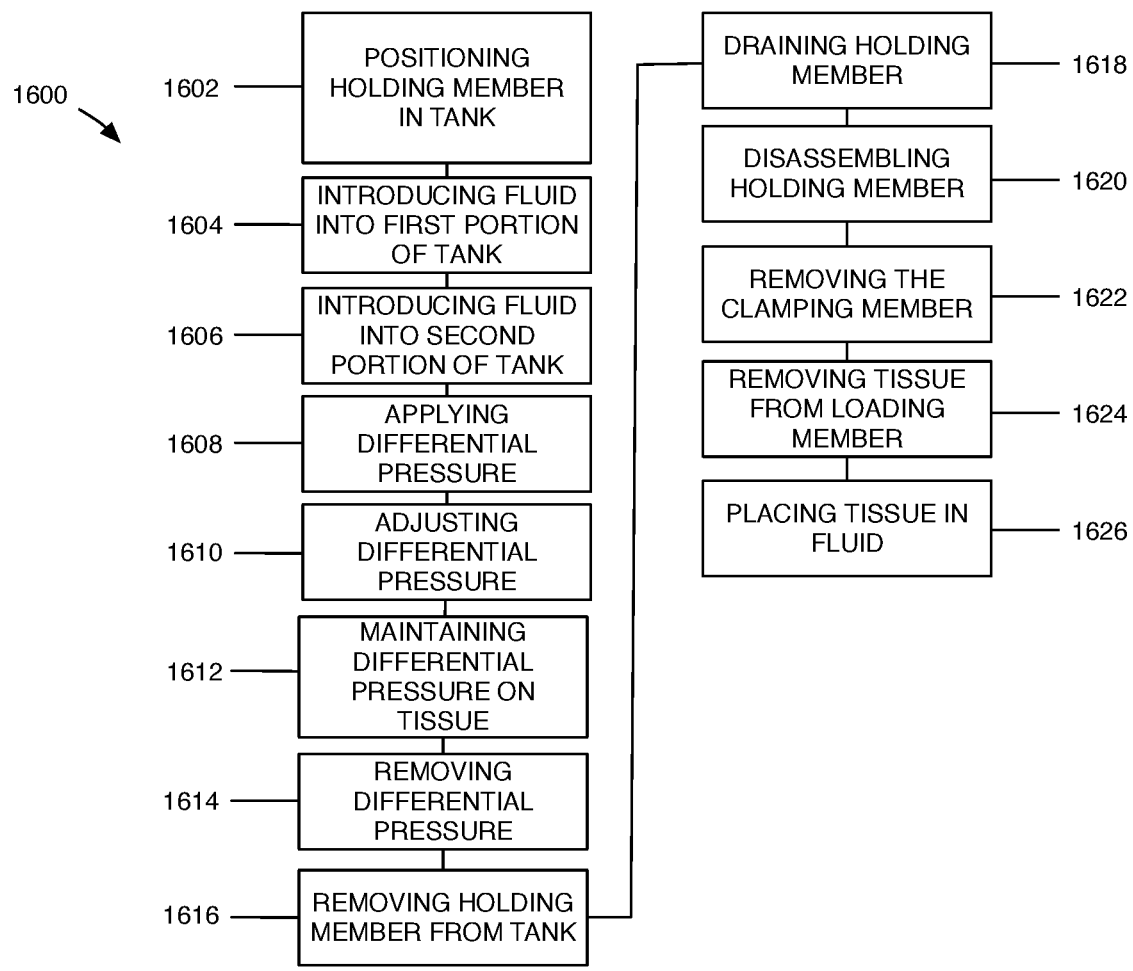
FIG. 38 is a schematic illustration of another example method of processing tissue.

FIG. 38 is a schematic illustration of another example method 1600 of processing tissue.

A step 1602 comprises positioning a holding member in a tank. The holding member has tissue disposed between a loading member and a clamping member. Another step 1604 comprises introducing a fluid into the first portion of the tank. Another step 1606 comprises introducing fluid into a second portion of the tank. Another step 1608 comprises applying differential pressure to the tissue and between the first portion of the tank and the second portion of the tank. Another step 1610 comprises adjusting the differential pressure between the first portion of the tank and the second portion of the tank. Another step 1612 comprises maintaining the differential pressure on the tissue for a period of time. Another step 1614 comprises removing the differential pressure from the tissue. Another step 1616 comprises removing the holding member from the tank. Another step 1618 comprises draining the holding member. Another step 1620 comprises disassembling the holding member. Another step 1622 comprises removing the clamping member from the loading member. Another step 1624 comprises removing tissue from the loading member. Another step 1626 comprises placing the tissue in a fluid for a period of time.

Step 1602 can be accomplished by positioning any suitable holding member in any suitable tank. For example, the holding member 814 illustrated in FIG. 19 can be positioned within the tank 812.

Step 1604 can be accomplished as described above with respect to step 1312 and relative to the first portion of the tank (e.g., first holding member chamber 864).

Step 1606 can be accomplished as described above with respect to step 1312 and relative to the second portion of the tank (e.g., second holding member chamber 866).

Step 1608 can be accomplished by applying a force (e.g., torque) on the actuator to move it to its second position.

The differential pressure being applied to tissue can vary during a method of processing tissue due to the permeability of the tissue, which results in fluid passing through the tissue from a first holding member chamber to a second holding member chamber. Step 1610 can be accomplished by adjusting the rate of fluid being pumped by the pump, adjusting the position of the actuator between its first and second positions, and/or any other technique or method considered suitable for a particular embodiment. Optionally, step 1610 can be omitted from method 1600 in embodiments in which adjustment is not required. An optional step comprises determining the pressure differential between the first holding member chamber and second holding member chamber. This optional step allows for a determination as to whether an adjustment to the differential pressure is necessary and can be accomplished using a first pressure transducer disposed within the first holding member chamber and a second pressure transducer disposed within the second holding member chamber. Another optional step comprises determining the characteristics of the tissue. This optional step can be accomplished using an ultrasound transducer in communication with one, or both, of the first holding member chamber and second holding member chamber. These optional steps can be accomplished while a pump is in an on state and a differential pressure is being applied to the tissue.

Step 1612 can be accomplished by maintaining the position of the actuator.

Step 1614 can be accomplished by applying a force (e.g., torque) on the actuator to move it to its first position or a position in which no differential pressure is applied to the tissue.

Step 1616 can be accomplished by applying a force on the holding member away from the tank until the holding member is free of the tank.

Step 1618 can be accomplished as described above with respect to step 1330. Step 1620 can be accomplished as described above with respect to step 1332. Step 1622 can be accomplished as described above with respect to step 1334. Step 1624 can be accomplished as described above with respect to step 1336. Step 1626 can be accomplished as described above with respect to step 1338.

While various steps, alternative steps, and optional steps have been described above with respect to the example method 1600, these steps, alternative steps, and optional steps can be included in, accomplished concurrently with, and/or accomplished in the alternative to, the method, steps, alternative steps, and/or optional steps described herein with respect to example method 1300, example method 1400, and/or example method 1500.

FIGS. 39, 40, 41, 42, 43, 44, 45, and 46 provide graphical representations illustrating a comparison of a load response over time in the x-axis and y-axis of tissue fixed in a fixative using currently available processing techniques and tissue fixed in a fixative using the differential pressure material processing systems, apparatus, and methods described herein. In each of the groups tested, the sample geometry, total deformation, and loading rate were the same.

As shown, the data relating to the tissue processed using the differential pressure material processing systems, apparatus, and methods described herein, both for a given fixation pressure and across fixation pressures, is tightly grouped in terms of maximum load achieved and the shape of the curves and the data relating to the tissue processed using currently available processing techniques varies greatly. The consistency in the tissue processed using the differential pressure material processing systems, apparatus, and methods described herein is considered advantageous at least because it allows for repeatable tissue fabrication and tissue function, such as when the tissue is formed as a valve or a portion of a valve. In addition, the data indicates that tissues processed using currently available processing techniques are stiffer than tissues processed using the differential pressure material processing systems, apparatus, and methods described herein. It is considered advantageous to form low stiffness tissues at least because such tissues, when formed as a valve or a portion of a valve, are responsive to small pressure differentials in vivo.

Figure 39:
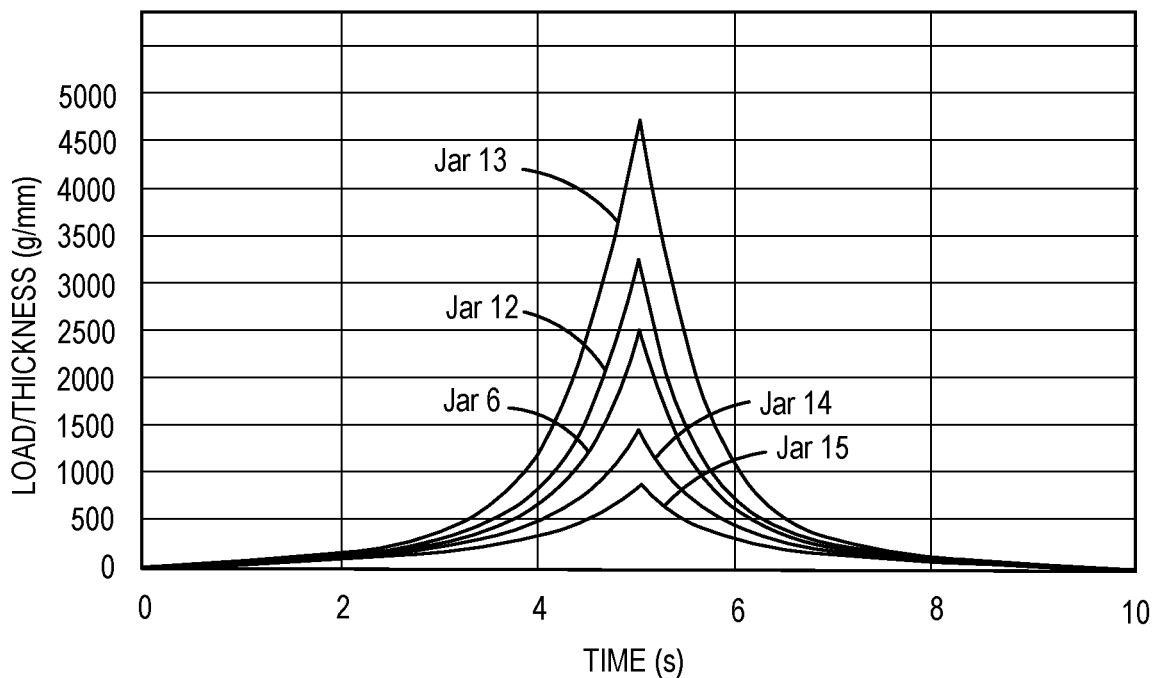
FIG. 39 is a graphical representation of a load response over time in the x-axis of tissue fixed in a fixative using current processing techniques.
Figure 40:
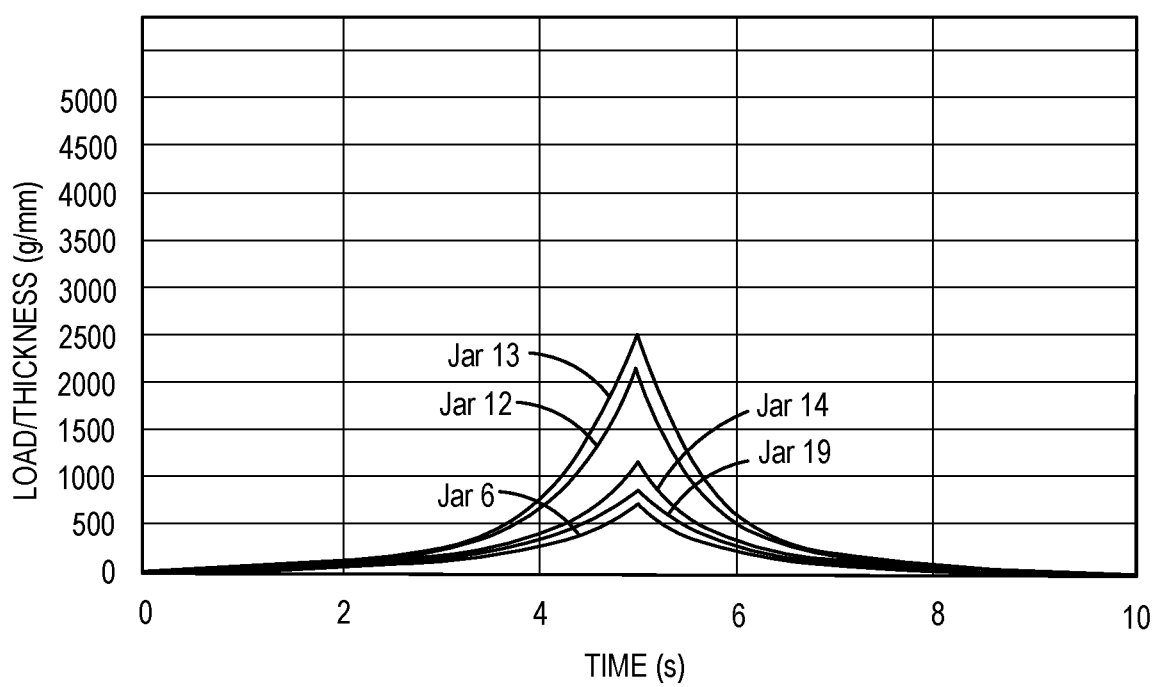
FIG. 40 is a graphical representation of a load response over time in the y-axis of tissue fixed in a fixative using currently available processing techniques.
Figure 41:
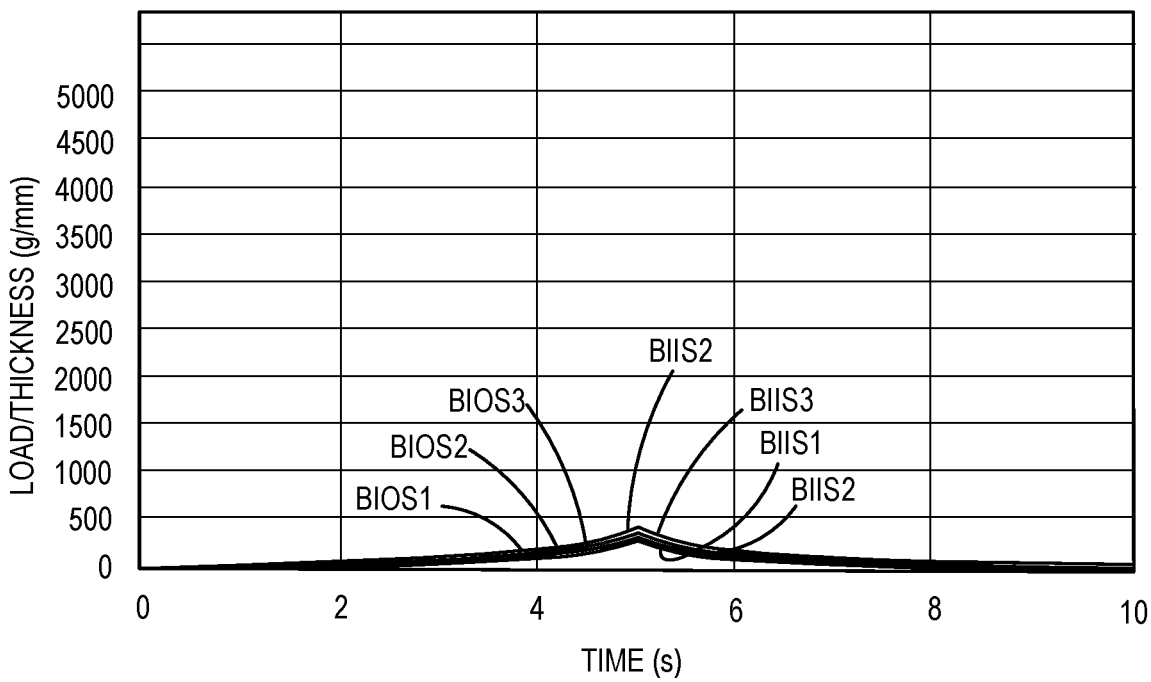
FIG. 41 is a graphical representation of a load response over time in the x-axis of tissue fixed in a fixative using the differential pressure material processing systems and methods described herein. The differential pressure applied to the tissue is 0.25 millimeters of mercury.
Figure 42:
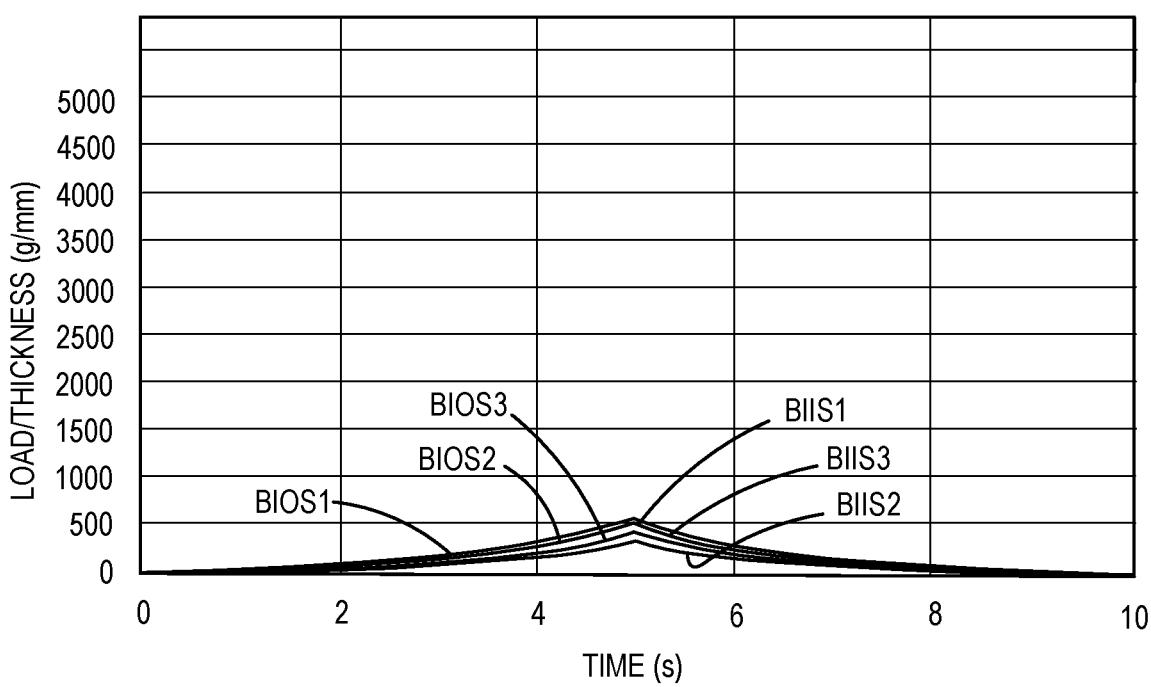
FIG. 42 is a graphical representation of a load response over time in the y-axis of tissue fixed in a fixative using the differential pressure material processing systems and methods described herein. The differential pressure applied to the tissue is 0.25 millimeters of mercury.
Figure 43:
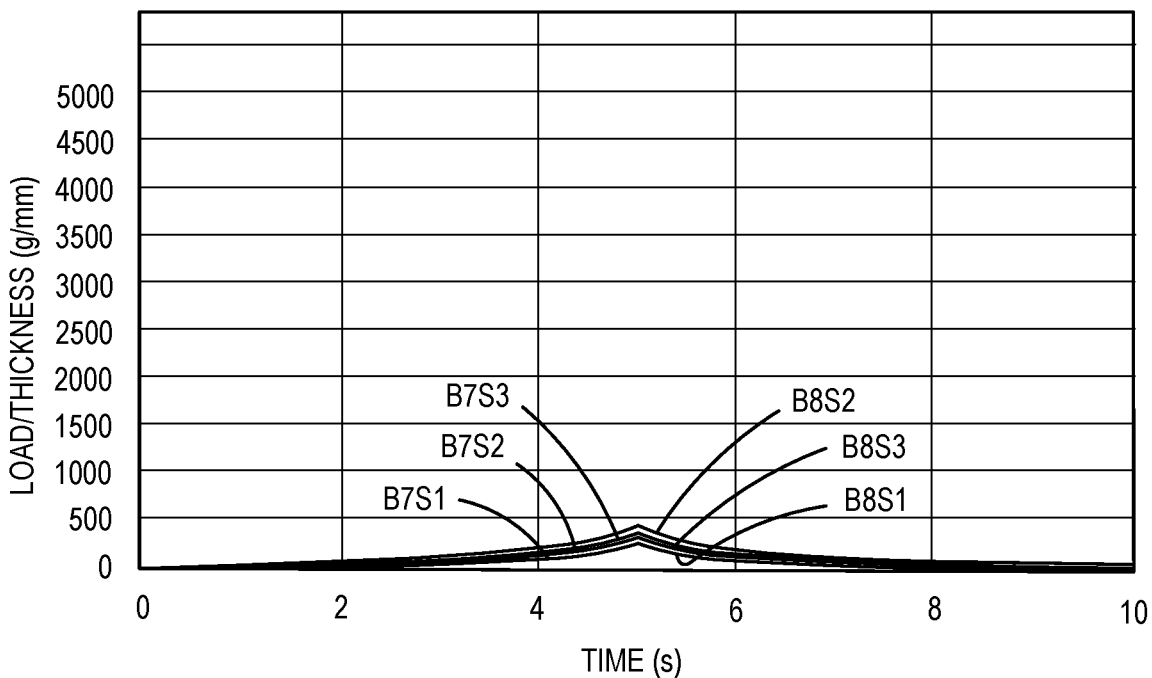
FIG. 43 is a graphical representation of a load response over time in the x-axis of tissue fixed in a fixative using the differential pressure material processing systems and methods described herein. The differential pressure applied to the tissue is 0.5 millimeters of mercury.
Figure 44:
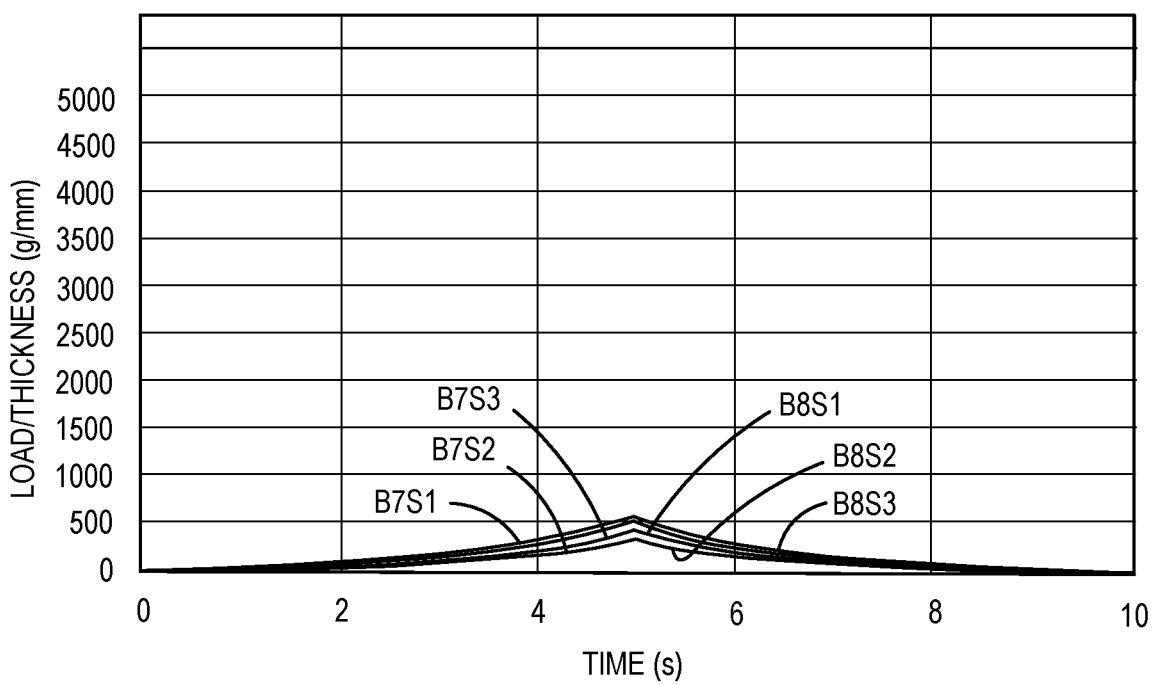
FIG. 44 is a graphical representation of a load response over time in the y-axis of tissue fixed in a fixative using the differential pressure material processing systems and methods described herein. The differential pressure applied to the tissue is 0.5 millimeters of mercury.
Figure 45:
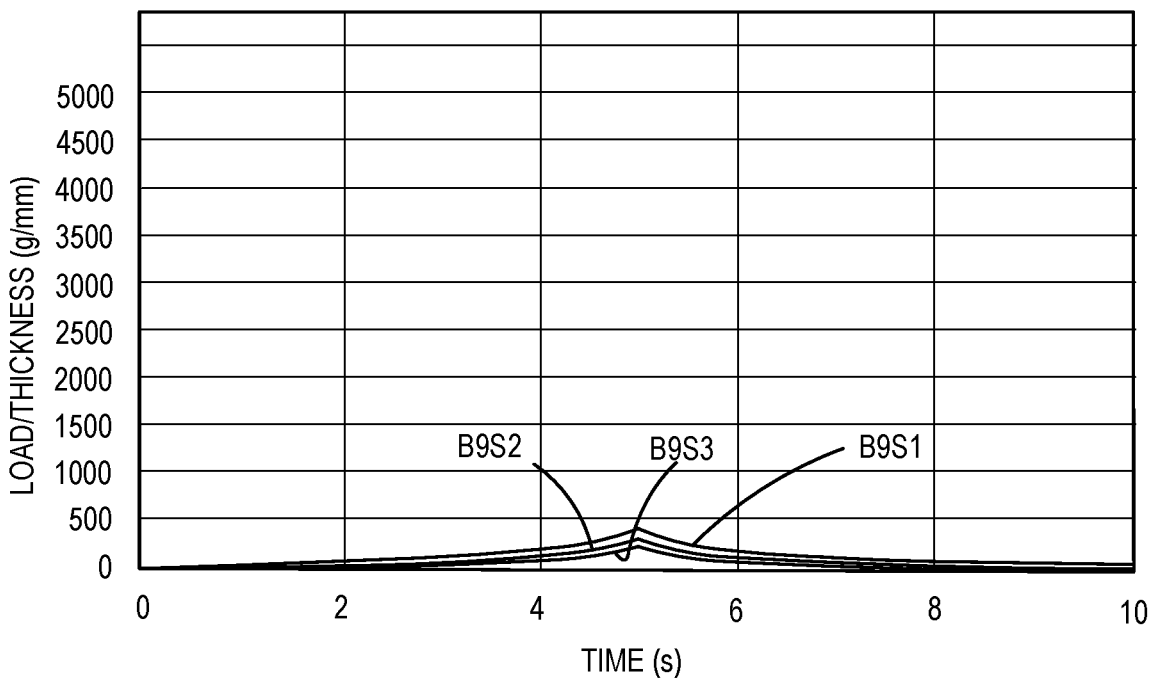
FIG. 45 is a graphical representation of a load response over time in the x-axis of tissue fixed in a fixative using the differential pressure material processing systems and methods described herein. The differential pressure applied to the tissue is 1.0 millimeter of mercury.
Figure 46:
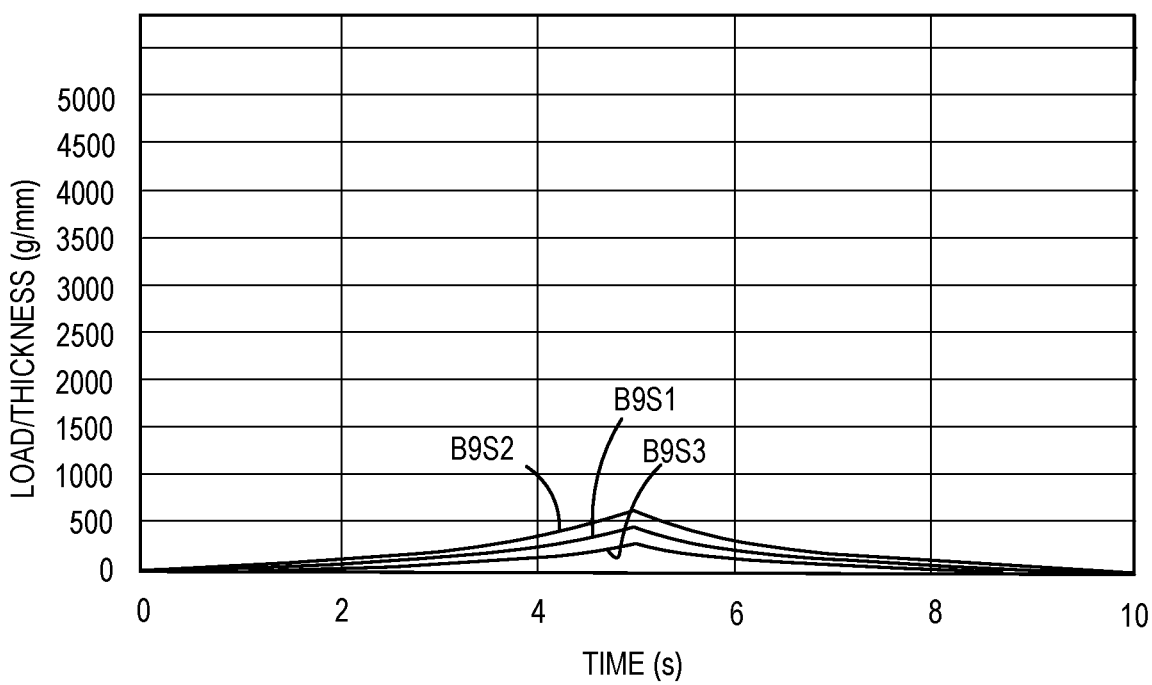
FIG. 46 is a graphical representation of a load response over time in the y-axis of tissue fixed in a fixative using the differential pressure material processing systems and methods described herein. The differential pressure applied to the tissue is 1.0 millimeter of mercury.
Figure 47:
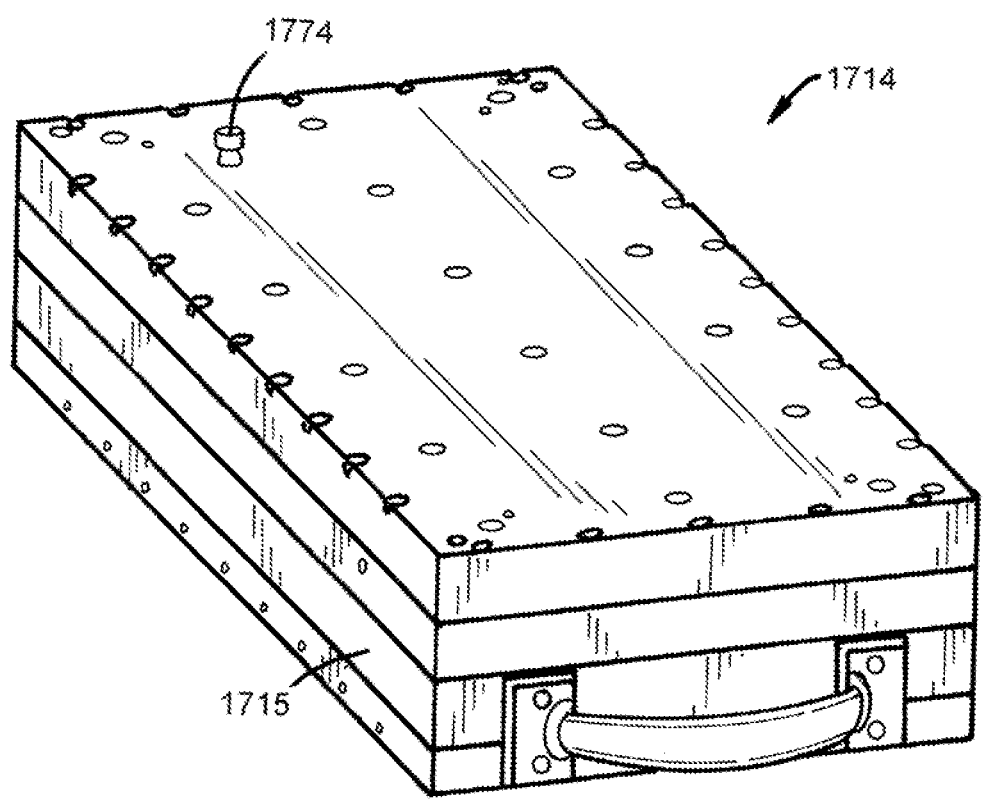
FIG. 47 is a perspective view of an alternative holding member that can used in a differential pressure material processing system.

FIG. 39 is a graphical representation of a load response over time in the x-axis under equibiaxial loading conditions of porcine visceral pleura fixed in phosphate buffered, 0.625% glutaraldehyde using current processing techniques (e.g., techniques known to those who are experts in the field). FIG. 40 is a graphical representation of a load response over time in the y-axis under equibiaxial loading conditions of porcine visceral pleura fixed in phosphate buffered, 0.625% glutaraldehyde using current processing techniques (e.g., techniques known to those who are experts in the field). FIG. 41 is a graphical representation of a load response over time in the x-axis under equibiaxial loading conditions of porcine visceral pleura fixed in phosphate buffered, 0.625% glutaraldehyde at a differential pressure of 0.25 millimeters of mercury for four hours using the differential pressure material processing systems and methods described herein. FIG. 42 is a graphical representation of a load response over time in the y-axis under equibiaxial loading conditions of porcine visceral pleura fixed in phosphate buffered, 0.625% glutaraldehyde at a differential pressure of 0.25 millimeters of mercury for four hours using the differential pressure material processing systems and methods described herein. FIG. 43 is a graphical representation of a load response over time in the x-axis under equibiaxial loading conditions of porcine visceral pleura fixed in phosphate buffered, 0.625% glutaraldehyde at a differential pressure of 0.5 millimeters of mercury for four hours using the differential pressure material processing systems and methods described herein. FIG. 44 is a graphical representation of a load response over time in the y-axis under equibiaxial loading conditions of porcine visceral pleura fixed in phosphate buffered, 0.625% glutaraldehyde at a differential pressure of 0.5 millimeters of mercury for four hours using the differential pressure material processing systems and methods described herein. FIG. 45 is a graphical representation of a load response over time in the x-axis under equibiaxial loading conditions of porcine visceral pleura fixed in phosphate buffered, 0.625% glutaraldehyde at a differential pressure of 1.0 millimeters of mercury for four hours using the differential pressure material processing systems and methods described herein. FIG. 46 is a graphical representation of a load response over time in the y-axis under equibiaxial loading conditions of porcine visceral pleura fixed in phosphate buffered, 0.625% glutaraldehyde at a differential pressure of 1.0 millimeters of mercury for four hours using the differential pressure material processing systems and methods described herein.

FIGS. 47, 48, 49, 50, 51, 52 illustrate an alternative holding member 1714 that can be used in a differential pressure material processing system, such as differential pressure material processing system 10. The holding member 1714 is similar to the holding member 14 illustrated in FIGS. 1, 4, and 5 and described above, except as detailed below. The holding member 1714 includes a loading member 1760, a clamping member 1762 releasably attached to the loading member 1760, and defines a first holding member chamber 1764, a second holding member chamber 1766, a plurality of passageways 1768 in communication with the first holding member chamber 1764 and second holding member chamber 1766, a first input port 1774, and a second input port 1776. The loading member 1760 defines a first guide member 1790, the first input port 1774, and a plurality of support members 1792 spanning each passageway of the plurality of passageways 1768 and the clamping member 1762 defines a second guide member 1798 and the second input port 1776. FIGS. 48, 49, 50, 51, and 52 illustrate a single support member 1792 and associated structure for clarity. However, the position of the remaining support members of the plurality of support members 1792 has been illustrated. For clarity, the illustrated embodiment omits the inclusion of drains and vents, such as those described herein. However, holding member 1714 can include one or more drains and/or one or more vents, such as those described herein.

Figure 48:
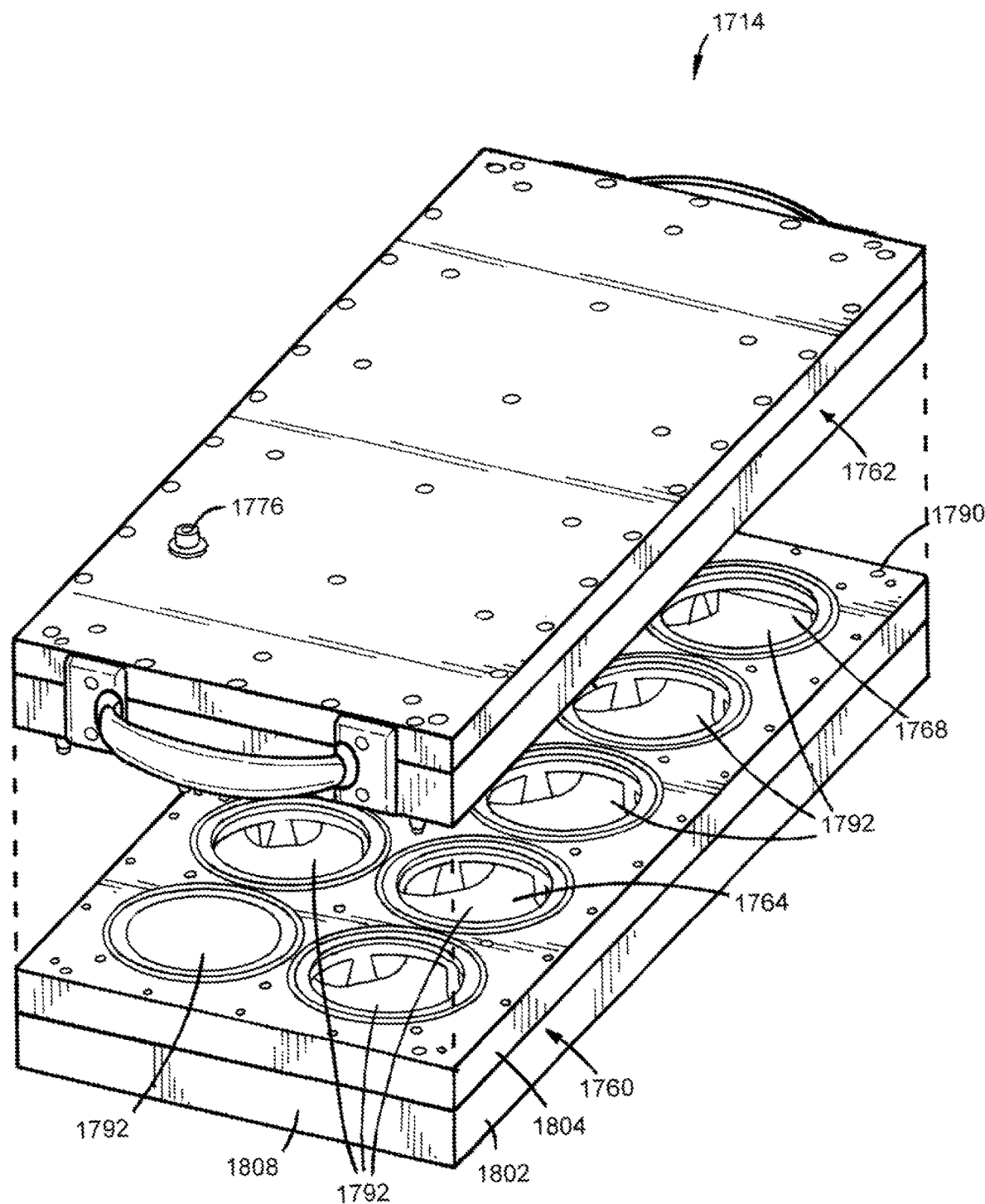
FIG. 48 is an exploded view of the holding member illustrated in FIG. 47.
Figure 49:
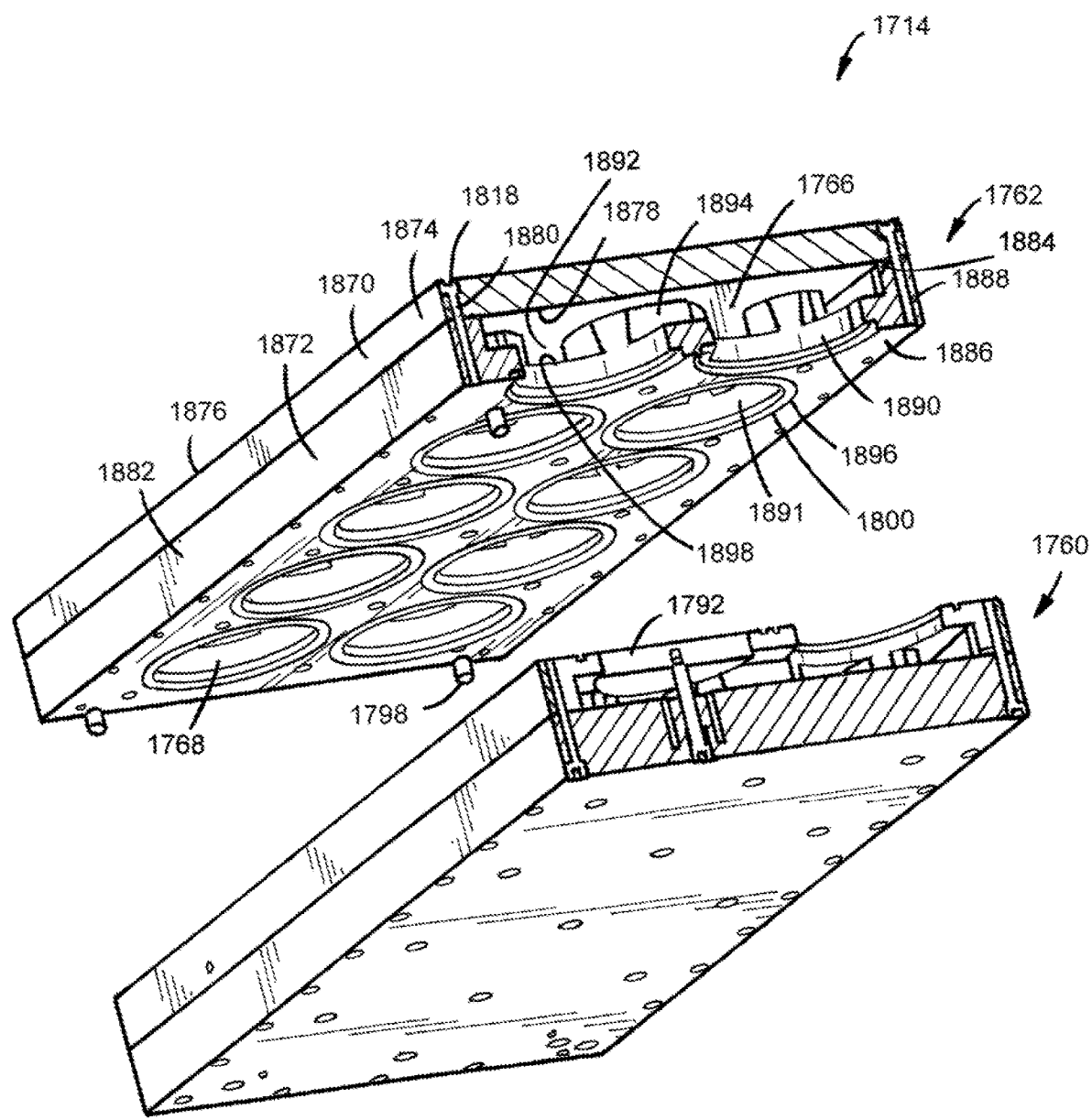
FIG. 49 is a sectional view of the holding member illustrated in FIG. 48. The support member of the loading member is in a first position.
Figure 50:
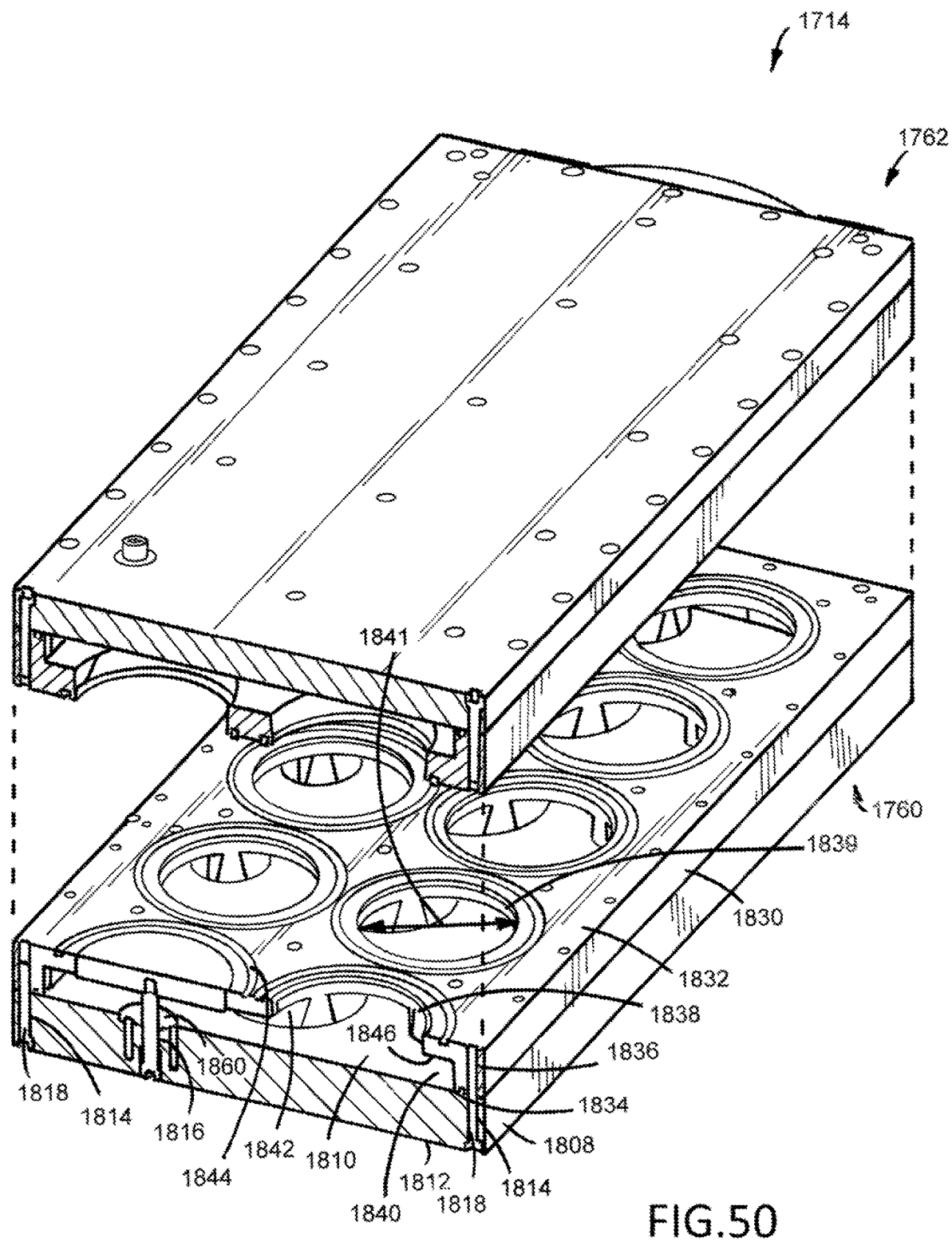
FIG. 50 is another sectional view of the holding member illustrated in FIG. 48. The support member of the loading member is in a first position.
Figure 51:
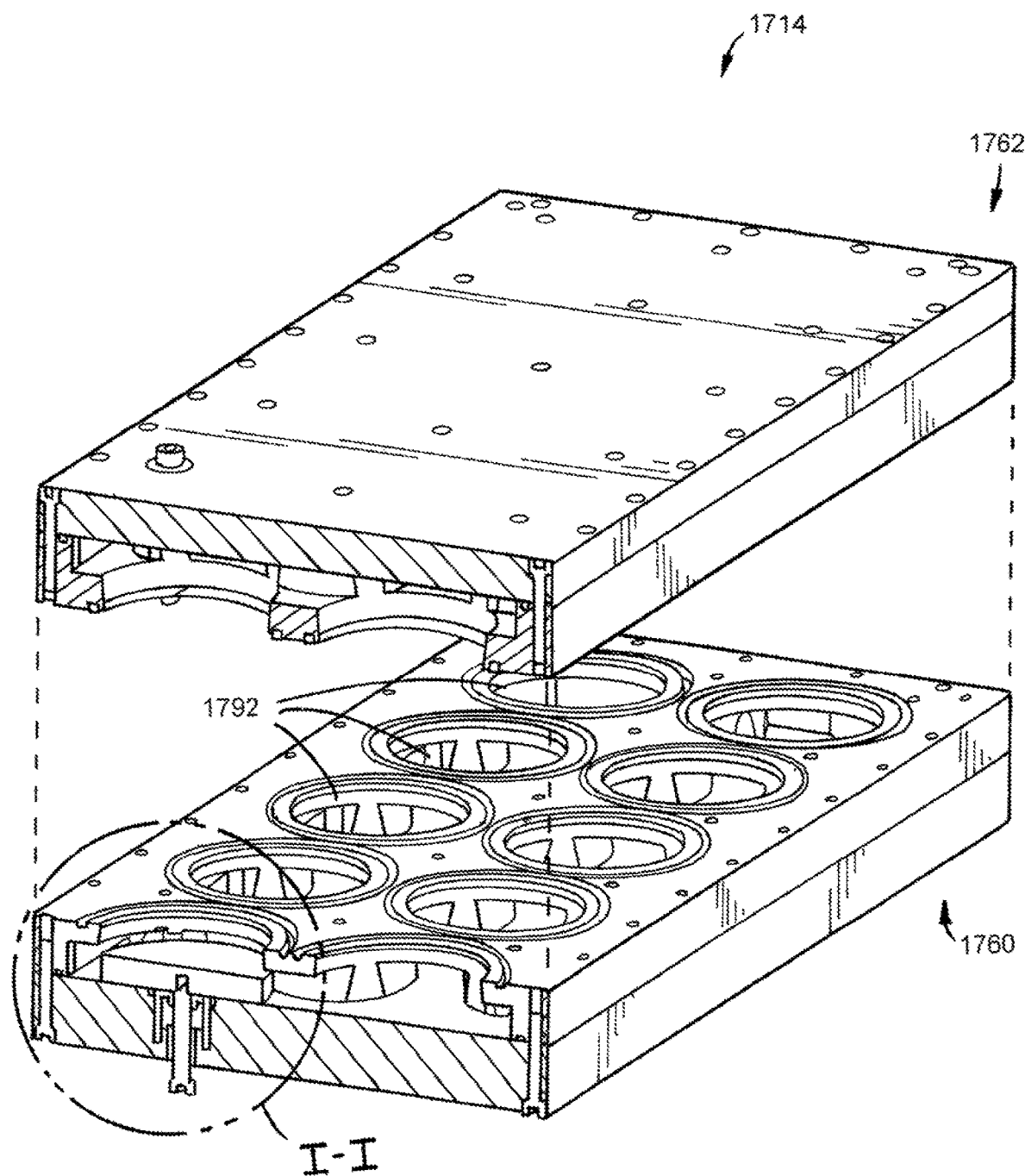
FIG. 51 is another sectional view of the holding member illustrated in FIG. 48. The support member of the loading member is in a second position.
Figure 52:
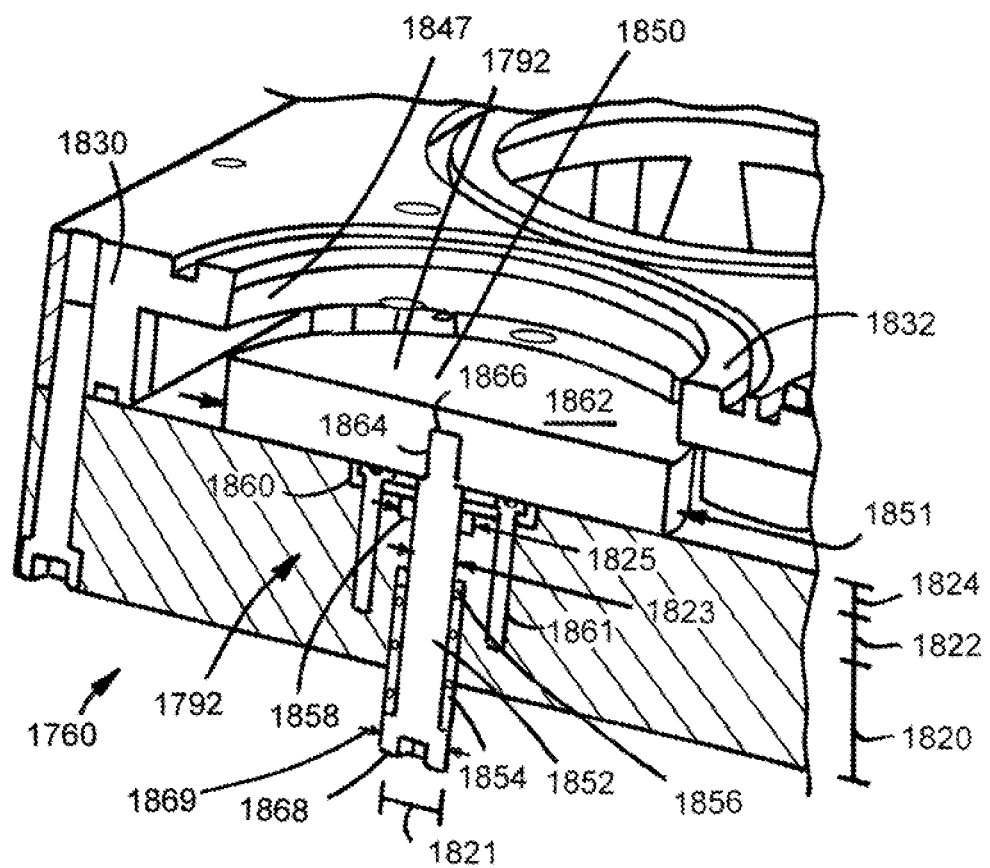
FIG. 52 is a magnified view of area I-I illustrated in FIG. 51.

In the illustrated embodiment, the loading member 1760 has a first portion 1802 and a second portion 1804 releasably attached to the first portion 1802. Each support member of the plurality of support members 1792 is movable between a first position, as shown in FIGS. 51 and 52, and a second position, as shown in FIGS. 48, 49, and 50. The first holding member chamber 1764 is cooperatively defined by the first portion 1802 and the second portion 1804.

The first portion 1802 has a main body 1808 that defines a top surface 1810, a bottom surface 1812, a first plurality of passageways 1814, and a second plurality of passageways 1816. The figures illustrate a single passageway of the second plurality of passageways 1816. However, a passageway of the plurality of second passageways 1816 will be defined for each support member of the plurality of support members 1792. Each passageway of the first plurality of passageways 1814 extends through the main body 1808 from the top surface 1810 to the bottom surface 1812 and is sized and configured to receive a portion of a fastener 1818 such that releasable attachment between the first portion 1802 and the second portion 1804 can be accomplished. Each passageway of the second plurality of passageways 1816 extends through the main body 1808 from the top surface 1810 to the bottom surface 1812 and is sized and configured to a portion of a support member of the plurality of support members 1792, as described in more detail herein. Each passageway of the second plurality of passageways 1816 has a first portion 1820, a second portion 1822, and a third portion 1824. The first portion 1820 extends from the bottom surface 1812 to the second portion 1822 and has a first inside diameter 1821. The second portion 1822 is disposed between the first portion 1820 and the third portion 1824 and has a second inside diameter 1823. The third portion 1824 extends from the second portion 1822 to the top surface 1810 and has a third inside diameter 1825. The first inside diameter 1821 is greater than the second inside diameter 1823. The second inside diameter 1823 is less than the third inside diameter 1825.

The second portion 1804 has a main body 1830 that defines a top surface 1832, a bottom surface 1834, a first plurality of passageways 1836, a second plurality of passageways 1838, a recess 1840, a plurality of support posts 1842, and a plurality of recesses 1844. Each passageway of the first plurality of passageways 1836 extends through the main body 1830 from the top surface 1832 to the bottom surface 1834 and is sized and configured to receive a portion of a fastener 1818 such that releasable attachment between the first portion 1802 and the second portion 1804 can be accomplished. Each passageway of the second plurality of passageways 1838 comprises a first portion 1839 of each passageway of the plurality of passageways 1768, as described in more detail herein, and has an inside diameter 1841. The recess 1840 extends from the bottom surface 1834 toward the top surface 1832 to a recess base 1846. Each passageway of the second plurality of passageways 1838 extends from the top surface 1832 to the recess base 1846. As shown in FIG. 52, the main body 1830 defines an angled edge 1847 from the recess base 1846 to the opening defining a passageway of the second plurality of passageways 1838, which allows for the shedding of air bubbles when the holding member 1714 is being filled with fluid. Each support post of the plurality of support posts 1842 extends from the recess base 1846 to a hypothetical plane that includes the bottom surface 1834. Each support post of the plurality of support posts 1842 is sized and configured to contact a support member and guide the support member toward the opening defining a passageway of the second plurality of passageways 1838. Each recess of the plurality of recesses 1844 surrounds a passageway of the second plurality of passageways 1838.

As shown in FIG. 52, each support member of the plurality of support members 1792 includes a plate 1850, an elongate member 1852, a spring 1854, a first O-ring 1856, a second O-ring 1858, and a locking plate 1860. The plate 1850 defines a support surface 1862 and a recess 1864. In the illustrated embodiment, the plate 1850 has an outside diameter 1851 that is less than the inside diameter 1841 of a passageway of the second plurality of passageways 1768. The support surface 1862 is not disposed on a hypothetical plane that includes the top surface 1832 of the second portion 1804 when the support member 1792 is in the first position and is disposed on a hypothetical plane that includes the top surface 1832 of the second portion 1804 when the support member 1792 is in the second position. In alternative embodiments, a plate can be perforated and/or sized such that the outside diameter is equal to, or substantially equal, the inside diameter of a of a passageway of a second plurality of passageways. The elongate member 1852 has a first end 1866 disposed within the recess 1864 and a second end 1868 disposed external to the first portion 1820 of a passageway of the second plurality of passageways 1816 when the support member 1792 is in the first position and within the first portion 1820 when in the second position. The second end 1868 has an outside diameter 1869 that is less than the first inside diameter 1821 and greater than the second inside diameter 1823. The spring 1854 is a compression spring that is disposed between the second end 1868 of the elongate member 1852 and the second portion 1822 of a passageway of the second plurality of passageways 1816. The spring 1854 biases the support member to the first position. The first O-ring 1856 is disposed within the first portion 1820 of a passageway of the second plurality of passageways 1816 between the first portion 1802 and the spring 1854. The second O-ring 1858 is disposed within the third portion 1824 of a passageway of the second plurality of passageways 1816 between the first portion 1802 and the locking plate 1860. The locking plate 1860 is disposed between the plate 1850 and the second O-ring 1858 when the support member 1792 is in the first position. The locking plate 1860 is attached to the first portion 1802 using fasteners 1861.

A loading member and/or support member can be formed of any suitable material and selection of a suitable material can be based on various considerations, including the tissue intended to be processed. Examples of materials considered suitable to form a loading member and/or a portion, or the entirety, of a support member include those described herein, low-friction materials, such as Teflon, materials that include a pre-applied lubricous coating, and any other material considered suitable for a particular embodiment.

In the illustrated embodiment, the clamping member 1762 has a first portion 1870 and a second portion 1872 releasably attached to the first portion 1870. The second holding member chamber 1766 is cooperatively defined by the first portion 1870 and the second portion 1872.

The first portion 1870 has a main body 1874 that defines a top surface 1876, a bottom surface 1878, and a first plurality of passageways 1880. Each passageway of the first plurality of passageways 1880 extends through the main body 1874 from the top surface 1876 to the bottom surface 1878 and is sized and configured to receive a portion of a fastener 1818 such that releasable attachment between the first portion 1870 and the second portion 1872 can be accomplished.

The second portion 1872 has a main body 1882 that defines a top surface 1884, a bottom surface 1886, a first plurality of passageways 1888, a second plurality of passageways 1890, a recess 1892, a plurality of support posts 1894, and a plurality of recesses 1896. Each passageway of the first plurality of passageways 1888 extends through the main body 1882 from the top surface 1884 to the bottom surface 1886 and is sized and configured to receive a portion of a fastener 1818 such that releasable attachment between the first portion 1870 and the second portion 1872 can be accomplished. Each passageway of the second plurality of passageways 1890 comprises a second portion 1891 of each passageway of the plurality of passageways 1768, as described in more detail herein. The recess 1892 extends from the top surface 1884 toward the bottom surface 1886 to a recess base 1898. Each support post of the plurality of support posts 1894 extends from the recess base 1898 toward a hypothetical plane that includes the top surface 1884. Each recess of the plurality of recesses 1896 surrounds a passageway of the second plurality of passageways 1890. A sealing member 1800 is disposed within each recess of the plurality of recesses 1896. Each sealing member 1800 contacts a portion of the loading member 1760 disposed between a recess of the plurality of recesses 1844 and a passageway of the second plurality of passageways 1838 when the clamping member 1762 is releasably attached to the loading member 1760. In the illustrated embodiment, each sealing member 1800 contacts the top surface 1832 of the second portion 1804 of the loading member 1760. This arrangement allows for excess tissue to be disposed within a recess of the plurality of recesses 1844 when the clamping member 1762 is releasably attached to the loading member 1760. In alternative embodiments, a plurality of recesses 1844 could be omitted from a second portion 1804 of a loading member 1760 and a main body of a second portion of a loading member could define a single recess that extends from a top surface defining an opening toward a bottom surface such that the openings to a plurality of passageways are defined by a plurality of projections.

In use, each support member of the plurality of support members 1792 is in the first position when the bottom surface 1812 of the first portion 1802 is free of contact from a platform (e.g., a side 1715 of the holding member 1714 is positioned on a platform or table). Each support member of the plurality of support members 1792 is in the second position when the bottom surface 1812 of the first portion 1802 is positioned on a platform and contacts the platform resulting in the springs 1854 contracting and the plates 1850 being disposed on a hypothetical plane with the top surface 1832 of the second portion 1804.

Those with ordinary skill in the art will appreciate that various modifications and alternatives for the described and illustrated embodiments can be developed in light of the overall teachings of the disclosure. Accordingly, the particular arrangements disclosed are intended to be illustrative only and not limiting as to the scope of the invention, which is to be given the full breadth of the appended claims and any and all equivalents thereof.

What is claimed is:

1. A differential pressure material processing system for processing tissue using a fluid, the system comprising:
   a tank defining a first portion and a second portion; and
   a holding member comprising a loading member and a clamping member releasably attached to the loading member, the loading member defining a first holding member chamber in fluid communication with the first portion of the tank, the clamping member defining a second holding member chamber in fluid communication with the second portion of the tank, the loading member and the clamping member cooperatively defining a passageway in fluid communication with the first holding member chamber and the second holding member chamber, said fluid having a first pressure when disposed within the first portion of the tank and the first holding member chamber, said fluid having a second pressure when disposed within the second portion of the tank and the second holding member chamber, the second pressure being different than the first pressure;
   wherein said tissue is disposed between the loading member and the clamping member such that a portion of said tissue spans an entire cross-section of the passageway to obstruct the passageway; and
   wherein the first portion of the tank and the second portion of the tank are separated by a first non-permeable wall.

2. The system of claim 1, further comprising a reservoir; and further comprising a pump having an inlet port and an outlet port, the outlet port in fluid communication with the first portion of the tank and the inlet port in fluid communication with the reservoir.

3. The system of claim 2, wherein the pump has an on state and an off state; and
   wherein the passageway is obstructed by said tissue when the pump is in the on state and the off state.

4. The system of claim 2, wherein the reservoir is defined by the tank.

5. The system of claim 1, wherein the loading member defines a perforated support member across the passageway.

6. The system of claim 1, wherein the loading member defines a support member across the passageway that is moveable between a first position and a second position.

7. The system of claim 6, wherein the support member is perforated.

8. The system of claim 1, wherein the loading member includes a first guide member and the clamping member includes a second guide member that mates with the first guide member to prevent movement of the loading member relative to the clamping member along an x-axis and a y-axis during releasable attachment of the clamping member to the loading member.

9. The system of claim 1, wherein the loading member defines a first portion of the passageway and the clamping member defines a second portion of the passageway such that the first portion of the passageway and the second portion of the passageway cooperatively define the passageway.

10. The system of claim 9, wherein the clamping member includes a sealing member that surrounds the second portion of the passageway defined by the clamping member.

11. The system of claim 1, further comprising a first pressure transducer in communication with the first holding member chamber.

12. The system of claim 1, further comprising an ultrasound transducer in communication with the first holding member chamber.

13. The system of claim 1, wherein the holding member is releasably disposed within the tank.

14. A differential pressure material processing system for processing tissue using a fluid, the system comprising:
   a tank defining a first portion and a second portion;
   a holding member comprising a loading member and a clamping member releasably attached to the loading member, the loading member defining a first holding member chamber in fluid communication with the first portion of the tank, the clamping member defining a second holding member chamber in fluid communication with the second portion of the tank, the loading member and the clamping member cooperatively defining a passageway in fluid communication with the first holding member chamber and the second holding member chamber, said fluid having a first pressure when disposed within the first portion of the tank and the first holding member chamber, said fluid having a second pressure when disposed within the second portion of the tank and the second holding member chamber, the second pressure being less than the first pressure;
   a reservoir; and
   a pump having an inlet port and an outlet port, the outlet port in fluid communication with the first portion of the tank and the inlet port in fluid communication with the reservoir;
   wherein said tissue is disposed between the loading member and the clamping member such that a portion of said tissue spans an entire cross-section of the passageway to obstruct the passageway; and wherein the first portion of the tank and the second portion of the tank are separated by a first non-permeable wall.

15. The system of claim 1, wherein the first portion of the tank and the first holding member chamber are different; and wherein the second portion of the tank and the second holding member chamber are different.

\* \* \* \* \*